US009433686B2

(12) United States Patent
Karin et al.

(10) Patent No.: US 9,433,686 B2
(45) Date of Patent: Sep. 6, 2016

(54) METHODS FOR TREATING CASTRATION RESISTANT PROSTATE CANCER AND METASTASIS BY REDUCING B-CELL NUMBER AND/OR FUNCTION

(75) Inventors: Michael Karin, La Jolla, CA (US); Massimo Ammirante, San Diego, CA (US); Ali Kuraishy, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 339 days.

(21) Appl. No.: 13/982,083

(22) PCT Filed: Jan. 31, 2012

(86) PCT No.: PCT/US2012/023383
§ 371 (c)(1),
(2), (4) Date: Aug. 26, 2013

(87) PCT Pub. No.: WO2012/106368
PCT Pub. Date: Aug. 9, 2012

(65) Prior Publication Data
US 2014/0086918 A1    Mar. 27, 2014

Related U.S. Application Data

(60) Provisional application No. 61/438,052, filed on Jan. 31, 2011.

(51) Int. Cl.
| | |
|---|---|
| *A61K 39/00* | (2006.01) |
| *A61P 37/08* | (2006.01) |
| *A61K 47/48* | (2006.01) |
| *C07K 14/52* | (2006.01) |
| *C07K 16/24* | (2006.01) |
| *C07K 16/28* | (2006.01) |
| *A61K 38/17* | (2006.01) |
| *A61K 39/395* | (2006.01) |
| *A61K 31/381* | (2006.01) |
| *A61K 31/437* | (2006.01) |
| *C12N 15/113* | (2010.01) |

(52) U.S. Cl.
CPC ....... *A61K 47/48376* (2013.01); *A61K 31/381* (2013.01); *A61K 31/437* (2013.01); *A61K 38/1709* (2013.01); *A61K 38/1793* (2013.01); *A61K 39/395* (2013.01); *C07K 14/52* (2013.01); *C07K 16/24* (2013.01); *C07K 16/2887* (2013.01); *A61K 2039/505* (2013.01); *C07K 2317/76* (2013.01); *C07K 2319/30* (2013.01); *C12N 15/113* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 5,057,313 A | 10/1991 | Shih et al. | 424/1.53 |
| 5,475,092 A | 12/1995 | Chari et al. | 530/391.7 |
| 5,585,499 A | 12/1996 | Chari et al. | 548/420 |
| 5,736,137 A | 4/1998 | Anderson et al. | 424/133.1 |
| 5,846,545 A | 12/1998 | Chari et al. | 424/195.11 |
| 6,333,410 B1 | 12/2001 | Chari et al. | 540/456 |
| 6,340,701 B1 | 1/2002 | Chari et al. | 514/449 |
| 6,372,738 B2 | 4/2002 | Chari et al. | 514/232.5 |
| 6,429,295 B1 | 8/2002 | Carr Perez et al. | 530/387.5 |
| 7,202,346 B2 | 4/2007 | Payne et al. | 530/388.1 |
| 7,662,387 B2 | 2/2010 | Law et al. | 424/178.1 |
| 7,666,425 B1 | 2/2010 | Bander | 424/181.1 |
| 8,470,889 B2 * | 6/2013 | Wu | C07C 49/252 514/683 |

OTHER PUBLICATIONS

Ammirante et al (Nature, Mar. 2010, 464:302-306).*
Gasparian et al (Journal of Cell Science, 2002, 115:141-151).*
Yemelyanov et al (Oncogene, 2006, 25:387-398).*
American Cancer Society, "Cancer Facts & Figures 2007," Atlanta: American Cancer Society, pp. 1-21:A (2007).
American Cancer Society, "Cancer Facts & Figures 2007," Atlanta: American Cancer Society, pp. 22-54:B (2007).
American Cancer Society, "Cancer Facts & Figures 2010," Atlanta: American Cancer Society, pp. 1-22:A (2010).
American Cancer Society, "Cancer Facts & Figures 2010," Atlanta: American Cancer Society, pp. 23-64:B (2010).
Ammirante, et al., "B-Cell-Derived Lymphotoxin Promotes Castration-Resistant Prostate Cancer." *Nature*, 464(7286):302-305 (2010).
Anest, et al., "A Nucleosomal Function for IKappaB Kinase-α in NF-KappaB-Dependent Gene Expression." *Nature*, 423(6940):659-663 (2003).
Audet, et al., "Distinct Role of Gp130 Activation in Promoting Self-Renewal Divisions by Mitogenically Stimulated Murine Hematopoietic Stem Cells." *Proc Natl Acad Sci USA*, 98(4):1757-1762 (2001).
Bai, et al., "Rapid Tolerization of Virus-Activated Tumor-Specific CD8+ T Cells in Prostate Tumors of Tramp Mice." *Proc Natl Acad Sci USA*, 105(35):13003-13008 (2008).
Balkwill, et al., "Smoldering and Polarized Inflammation in the Initiation and Promotion of Malignant Disease." *Cancer Cell*, 7(3):211-217 (2005).

(Continued)

*Primary Examiner* — Laura B Goddard
(74) *Attorney, Agent, or Firm* — Medlen & Carroll, LLP

(57) ABSTRACT

The invention provides methods for reducing growth and/or metastasis of androgen-independent (castration resistant) prostate cancer in a tissue in an animal. In one embodiment the method comprises administering to the animal a therapeutically effective amount of a compound that reduces the number of B cells, and/or the function of B cells, in the tissue. In yet another embodiment, the invention provides methods for reducing androgen-induced growth of prostate epithelial cells in prostate tissue in an animal. In one embodiment, the method comprises administering to the animal a therapeutically effective amount of a compound that reduces the number of B cells, and/or the function of B cells, in the tissue.

3 Claims, 36 Drawing Sheets

(56) References Cited

OTHER PUBLICATIONS

Balkwill and Mantovani, "Inflammation and Cancer: Back to Virchow?" *Lancet*, 357(9255):539-545 (2001).

Beachy, et al., "Tissue Repair and Stem Cell Renewal in Carcinogenesis." *Nature*, 432(7015):324-331 (2004).

Ben-Neriah and Karin, "Inflammation Meets Cancer, with NF-KappaB as the Matchmaker." *Nat Immunol*, 12(8):715-723 (2011).

Berezovska, et al., "Essential Role for Activation of the Polycomb Group (Pcg) Protein Chromatin Silencing Pathway in Metastatic Prostate Cancer." *Cell Cycle*, 5(16):1886-1901 (2006).

Bonizzi, et al., "Activation of IKKα Target Genes Depends on Recognition of Specific KappaB Binding Sites by Relb:P52 Dimers." *EMBO J*, 23(21):4202-4210 (2004).

Borghouts, et al., "Current Strategies for the Development of Peptide-Based Anti-Cancer Therapeutics." *Journal of Peptide Science*, 11(11):713-726 (2005).

Cao, et al., "IKKα Provides an Essential Link between Rank Signaling and Cyclin D1 Expression During Mammary Gland Development." *Cell*, 107(6):763-775 (2001).

Chang, et al., "A Novel Peptide Enhances Therapeutic Efficacy of Liposomal Anti-Cancer Drugs in Mice Models of Human Lung Cancer." *PLoS One*, 4(1):e4171 (2009).

Chen, et al., "Immunoglobulin Gene Rearrangement in B Cell Deficient Mice Generated by Targeted Deletion of the Jh Locus." *Int Immunol*, 5(6):647-656 (1993).

Chen, et al., "Interleukin 6 Activates Androgen Receptor-Mediated Gene Expression through a Signal Transducer and Activator of Transcription 3-Dependent Pathway in Lncap Prostate Cancer Cells." *Cancer Res*, 60(8):2132-2135 (2000).

Coussens and Werb, "Inflammation and Cancer." *Nature*, 420(6917):860-867 (2002).

De Santa, et al., "The Histone H3 Lysine-27 Demethylase Jmjd3 Links Inflammation to Inhibition of Polycomb-Mediated Gene Silencing." *Cell*, 130(6):1083-1094 (2007).

de Visser, et al., "De Novo Carcinogenesis Promoted by Chronic Inflammation is B Lymphocyte Dependent." *Cancer Cell*, 7(5):411-423 (2005).

DeCaprio, et al., "Sv40 Large Tumor Antigen Forms a Specific Complex with the Product of the Retinoblastoma Susceptibility Gene." *Cell*, 54(2):275-283 (1988).

DeGregori and Johnson, "Distinct and Overlapping Roles for E2F Family Members in Transcription, Proliferation and Apoptosis." *Curr Mol Med*, 6(7):739-748 (2006).

Descargues, et al., "IKKα is a Critical Coregulator of a Smad4-Independent TGFβ-Smad2/3 Signaling Pathway That Controls Keratinocyte Differentiation." *Proc Natl Acad Sci USA*, 105(7):2487-2492 (2008).

Dvorak, "Tumors: Wounds That Do Not Heal. Similarities between Tumor Stroma Generation and Wound Healing." *N Engl J Med*, 315(26):1650-1659 (1986).

Ellwood-Yen, et al., "Myc-Driven Murine Prostate Cancer Shares Molecular Features with Human Prostate Tumors." *Cancer Cell*, 4(3):223-238 (2003).

English, et al., "Response of Glandular Versus Basal Rat Ventral Prostatic Epithelial Cells to Androgen Withdrawal and Replacement." *Prostate*, 11(3):229-242 (1987).

Eriksen, et al., "Constitutive Stat3-Activation in Sezary Syndrome: Tyrphostin Ag490 Inhibits Stat3-Activation, Interleukin-2 Receptor Expression and Growth of Leukemic Sezary Cells." *Leukemia*, 15(5):787-793 (2001).

Faisal, et al., "Leptosome-Entrapped Leptospiral Antigens Conferred Significant Higher Levels of Protection Than Those Entrapped with Pc-Liposomes in a Hamster Model." *Vaccine*, 27(47):6537-6545 (2009).

Galbiati, et al., "Regulation of E2F-1 after DNA Damage by P300-Mediated Acetylation and Ubiquitination." *Cell Cycle*, 4(7):930-939 (2005).

Garabedian, et al., "A Transgenic Mouse Model of Metastatic Prostate Cancer Originating from Neuroendocrine Cells." *Proc Natl Acad Sci U S A*, 95(26):15382-15387 (1998).

Ghiringhelli, et al., "Activation of the Nlrp3 INFlammasome in Dendritic Cells Induces IL-1β-Dependent Adaptive Immunity against Tumors." *Nat Med*, 15(10):1170-1178 (2009).

Gingrich, et al., "Metastatic Prostate Cancer in a Transgenic Mouse." *Cancer Res*, 56(18):4096-4102 (1996).

Greenberg, et al., "Prostate Cancer in a Transgenic Mouse." *Proc Natl Acad Sci U S A*, 92(8):3439-3443 (1995).

Grivennikov, et al., "Immunity, INFlammation, and Cancer." *Cell*, 140(6):883-899 (2010).

Gulley, et al., "Treatment Options for Androgen-Independent Prostate Cancer." *Clin Adv Hematol Oncol*, 1(1):49-57 (2003).

Guo, et al., "Mel-18, a Polycomb Group Protein, Regulates Cell Proliferation and Senescence Via Transcriptional Repression of Bmi-1 and C-Myc Oncoproteins." *Mol Biol Cell*, 18(2):536-546 (2007).

Hamel, et al., "Suppression of Proteoglycan-Induced Arthritis by Anti-CD20 B Cell Depletion Therapy is Mediated by Reduction in Autoantibodies and CD4+ T Cell Reactivity." *J Immunol*, 180(7):4994-5003 (2008).

Hoberg, et al., "IKappaB Kinase Alpha-Mediated Derepression of Smrt Potentiates Acetylation of Rela/P65 by P300." *Mol Cell Biol*, 26(2):457-471 (2006).

Holzbeierlein, et al., "Gene Expression Analysis of Human Prostate Carcinoma During Hormonal Therapy Identifies Androgen-Responsive Genes and Mechanisms of Therapy Resistance." *Am J Pathol*, 164(1):217-227 (2004).

Hu, et al., "Abnormal Morphogenesis but Intact IKK Activation in Mice Lacking the IKKα Subunit of IKappaB Kinase." *Science*, 284(5412):316-320 (1999).

Hu, et al., "IKKα Controls Formation of the Epidermis Independently of NF-KappaB." *Nature*, 410(6829):710-714 (2001).

Huang, et al., "Phosphorylation of CBP by IKKα Promotes Cell Growth by Switching the Binding Preference of CBP from P53 to NF-KappaB." *Mol Cell*, 26(1):75-87 (2007).

Hurwitz, et al., "The Tramp Mouse as a Model for Prostate Cancer." *Curr Protoc Immunol*, Chapter 20:Unit 20.5 (2001).

Hussain and Harris, "Inflammation and Cancer: An Ancient Link with Novel Potentials." *Int J Cancer*, 121(11):2373-2380(2007).

Huwyler, et al., "Tumor Targeting Using Liposomal Antineoplastic Drugs." *Int J Nanomedicine*, 3(1):21-29 (2008).

Ianari, et al., "Specific Role for P300/Creb-Binding Protein-Associated Factor Activity in E2f1 Stabilization in Response to DNA Damage." *J Biol Chem*, 279(29):30830-30835 (2004).

Isaacs, "The Biology of Hormone Refractory Prostate Cancer. Why Does It Develop?" *Urol Clin North Am*, 26(2):263-273 (1999).

Ito, et al., "Regulation of Oxidative Stress by Atm is Required for Self-Renewal of Haematopoietic Stem Cells." *Nature*, 431(7011):997-1002 (2004).

Izmailova, et al., "Use of Molecular Imaging to Quantify Response to IKK-2 Inhibitor Treatment in Murine Arthritis." *Arthritis Rheum*, 56(1):117-128 (2007).

Jacobs, et al., "BMI-1 Collaborates with C-Myc in Tumorigenesis by Inhibiting C-Myc-Induced Apoptosis Via Ink4a/Arf." *Genes Dev*, 13(20):2678-2690 (1999).

Jin, et al., "The Nuclear Factor-KappaB Pathway Controls the Progression of Prostate Cancer to Androgen-Independent Growth." *Cancer Res*, 68(16):6762-6769 (2008).

Jones and Baylin, "The Epigenomics of Cancer." *Cell*, 128(4):683-692 (2007).

Karhadkar, et al., "Hedgehog Signalling in Prostate Regeneration, Neoplasia and Metastasis." *Nature*, 431(7009):707-712 (2004).

Karin, "Inflammation and Cancer: The Long Reach of Ras." *Nat Med*, 11(1):20-21 (2005a).

Karin and Greten, "NF-KappaB: Linking Inflammation and Immunity to Cancer Development and Progression." *Nat Rev Immunol*, 5(10):749-759 (2005b).

Karin, "Nuclear Factor-KappaB in Cancer Development and Progression." *Nature*, 441(7092):431-436 (2006).

Karin, "NF-KappaB as a Critical Link between Inflammation and Cancer." *Cold Spring Harb Perspect Biol*, 1(5):a000141 (2009).

Karin, et al., "Innate Immunity Gone Awry. Linking Microbial Infections to Chronic Inflammation and Cancer." *Cell*, 124(4):823-835 (2006).

Kim, et al., "Carcinoma-Produced Factors Activate Myeloid Cells through Tlr2 to Stimulate Metastasis." *Nature*, 457(7225):102-106 (2009).

Konuma, et al., "Role of the Polycomb Group Proteins in Hematopoietic Stem Cells." *Dev Growth Differ*, 52(6):505-516 (2010).

(56) References Cited

OTHER PUBLICATIONS

Kortylewski and Yu, "Stat3 as a Potential Target for Cancer Immunotherapy." *J Immunother*, 30(2):131-139 (2007).
Kuhn, et al., "Inducible Gene Targeting in Mice." *Science*, 269(5229):1427-1429 (1995).
Kuraishy, et al., "TORC2 Regulates Germinal Center Repression of the TCL1 Oncoprotein to Promote B Cell Development and Inhibit Transformation." *Proceedings of the National Academy of Sciences*, 104(24):10175-10180 (2007).
Lee, et al., "Recruitment and Activation of Naive T Cells in the Islets by Lymphotoxin Beta Receptor-Dependent Tertiary Lymphoid Structure." *Immunity*, 25(3):499-509 (2006).
Legler, et al., "B Cell-Attracting Chemokine 1, a Human CXC Chemokine Expressed in Lymphoid Tissues, Selectively Attracts B Lymphocytes Via BLR1/CXCR5." *J Exp Med*, 187(4):655-660 (1998).
Lehr, et al., "Application of Photoshop-Based Image Analysis to Quantification of Hormone Receptor Expression in Breast Cancer." *J Histochem Cytochem*, 45(11):1559-1565 (1997).
Liu, et al., "Nonsteroidal Anti-inflammatory Drugs and Decreased Risk of Advanced Prostate Cancer: Modification by Lymphotoxin Alpha." *Am J Epidemiol*, 164(10):984-989 (2006).
Lobo, et al., "The Biology of Cancer Stem Cells." *Annu Rev Cell Dev Biol*, 23:675-699 (2007).
Lukacs, et al., "BMI-1 is a Crucial Regulator of Prostate Stem Cell Self-Renewal and Malignant Transformation." *Cell Stem Cell*, 7(6):682-693 (2010).
Luo, et al., "Inhibition of NF-KappaB in Cancer Cells Converts Inflammation-Induced Tumor Growth Mediated by TNFα to Trail-Mediated Tumor Regression." *Cancer Cell*, 6(3):297-305 (2004).
Luo, et al., "Nuclear Cytokine-Activated IKKα Controls Prostate Cancer Metastasis by Repressing Maspin." *Nature*, 446(7136):690-694 (2007).
Maitland and Collins, "Prostate Cancer Stem Cells: A New Target for Therapy." *J Clin Oncol*, 26(17):2862-2870 (2008).
Mantovani, et al., "Cancer-Related INFlammation." *Nature*, 454(7203):436-444 (2008).
Marinari, et al., "The Tumor Suppressor Activity of IKKα in Stratified Epithelia is Exerted in Part Via the TGF-β Antiproliferative Pathway." *Proc Natl Acad Sci USA*, 105(44):17091-17096 (2008).
Nimmerjahn and Ravetch, "Fc-Receptors as Regulators of Immunity." *Adv Immunol*, 96:179-204 (2007).
Nowak, et al., "Bmi1 is a Target Gene of E2F-1 and is Strongly Expressed in Primary Neuroblastomas." *Nucleic Acids Res*, 34(6):1745-1754 (2006).
Ohtani, et al., "Regulation of the Cyclin E Gene by Transcription Factor E2F1." *Proc Natl Acad Sci U S A*, 92(26):12146-12150 (1995).
Park, et al., "NF-KappaB in Breast Cancer Cells Promotes Osteolytic Bone Metastasis by Inducing Osteoclastogenesis Via GM-CSF." *Nat Med*, 13(1):62-69 (2007).
Richardson, et al.,"CD133, a Novel Marker for Human Prostatic Epithelial Stem Cells." *J Cell Sci*, 117(Pt 16):3539-3545 (2004).
Sakurai, et al., "Hepatocyte Necrosis Induced by Oxidative Stress and IL-1α Release Mediate Carcinogen-Induced Compensatory Proliferation and Liver Tumorigenesis." *Cancer Cell*, 14(2):156-165 (2008).
Scaffidi, et al., "Release of Chromatin Protein HMGB1 by Necrotic Cells Triggers INFlammation." *Nature*, 418(6894):191-195 (2002).
Senftleben, et al., "Activation by IKKα of a Second, Evolutionary Conserved, NF-KappaB Signaling Pathway." *Science*, 293(5534):1495-1499 (2001).
Sil, et al., "IKappaB Kinase-α Acts in the Epidermis to Control Skeletal and Craniofacial Morphogenesis." *Nature*, 428(6983):660-664 (2004).
Singer and Clark, "Cutaneous Wound Healing." *N Engl J Med*, 341(10):738-746 (1999).
Singh, et al., "Serum CXCL13 Positively Correlates with Prostatic Disease, Prostate-Specific Antigen and Mediates Prostate Cancer Cell Invasion, Integrin Clustering and Cell Adhesion." *Cancer Lett*, 283(1):29-35 (2009).
Smith, et al., "Interleukin-6 and Prostate Cancer Progression." *Cytokine Growth Factor Rev*, 12(1):33-40 (2001).
Song, et al., "Peptide Ligand-Mediated Liposome Distribution and Targeting to EGFR Expressing Tumor in Vivo." *Int J Pharm*, 363(1-2):155-161 (2008).
Taplin, et al., "Mutation of the Androgen-Receptor Gene in Metastatic Androgen-Independent Prostate Cancer." *N Engl J Med*, 332(21):1393-1398 (1995).
Tran, et al., "Development of a Second-Generation Antiandrogen for Treatment of Advanced Prostate Cancer." *Science*, 324(5928):787-790 (2009).
Tran, et al., "Development of a Second-Generation Antiandrogen for Treatment of Advanced Prostate Cancer." *Science*, 324(5928):787-790 Supporting Online Material (2009).
Trouche and Kouzarides, "E2F1 and E1A(12s) Have a Homologous Activation Domain Regulated by RB and CBP." *Proc Natl Acad Sci USA*, 93(4):1439-1442 (1996).
Tu, et al., "IKKα Regulates Estrogen-Induced Cell Cycle Progression by Modulating E2F1 Expression." *J Biol Chem*, 281(10):6699-6706 (2006).
Tumanov, et al., "Dissecting the Role of Lymphotoxin in Lymphoid Organs by Conditional Targeting." *Immunol Rev*, 195:106-116 (2003).
Vakkila and Lotze, "Inflammation and Necrosis Promote Tumour Growth." *Nat Rev Immunol*, 4(8):641-648 (2004).
Varambally, et al., "The Polycomb Group Protein Ezh2 Is Involved in Progression of Prostate Cancer." *Nature*, 419(6907):624-629 (2002).
Velnar, et al., "The Wound Healing Process: An Overview of the Cellular and Molecular Mechanisms." *J Int Med Res*, 37(5):1528-1542 (2009).
Visakorpi, et al., "In Vivo Amplification of the Androgen Receptor Gene and Progression of Human Prostate Cancer." *Nat Genet*, 9(4):401-406 (1995).
Voinea and Simionescu, "Designing of 'Intelligent' Liposomes for Efficient Delivery of Drugs." *Journal of Cellular and Molecular Medicine*, 6(4):465-474 (2002).
Wang, et al., "Role of Histone H2a Ubiquitination in Polycomb Silencing." *Nature*, 431(7010):873-878 (2004).
Watson, et al., "Context-Dependent Hormone-Refractory Progression Revealed through Characterization of a Novel Murine Prostate Cancer Cell Line." *Cancer Res*, 65(24):11565-11571 (2005).
Wen, et al., "A Selective Small Molecule IKappaB Kinase Beta Inhibitor Blocks Nuclear Factor KappaB-Mediated Inflammatory Responses in Human Fibroblast-Like Synoviocytes, Chondrocytes, and Mast Cells." *J Pharmacol Exp Ther*, 317(3):989-1001 (2006).
Widera, et al., "Tumor Necrosis Factor a Triggers Proliferation of Adult Neural Stem Cells Via IKK/NF-KappaB Signaling." *BMC Neurosci*, 7:64 (2006).
Worm, et al., "CD40 Ligation and IL-4 Use Different Mechanisms of Transcriptional Activation of the Human Lymphotoxin Alpha Promoter in B Cells." *Eur J Immunol*, 28(3):901-906 (1998).
Wu, et al., "Generation of a Prostate Epithelial Cell-Specific Cre Transgenic Mouse Model for Tissue-Specific Gene Ablation." *Mech Dev*, 101(1-2):61-69 (2001).
Yamamoto, et al., "Histone H3 Phosphorylation by IKK-α is Critical for Cytokine-Induced Gene Expression." *Nature*, 423(6940):655-659 (2003).
Yu, et al., "A Polycomb Repression Signature in Metastatic Prostate Cancer Predicts Cancer Outcome." *Cancer Res*, 67(22):10657-10663 (2007).
Zheng, et al., "CXCL13 Neutralization Reduces the Severity of Collagen-Induced Arthritis." *Arthritis Rheum*, 52(2):620-626 (2005).
Zong and Thompson, "Necrotic Death as a Cell Fate." *Genes Dev*, 20(1):1-15 (2006).
PCT/US12/23383 Third Party Observation (2010).
Lou, "A B cell burden in prostrate cancer." SciBX Cover Story pp. 1-2 (2010).

* cited by examiner

Figure 16
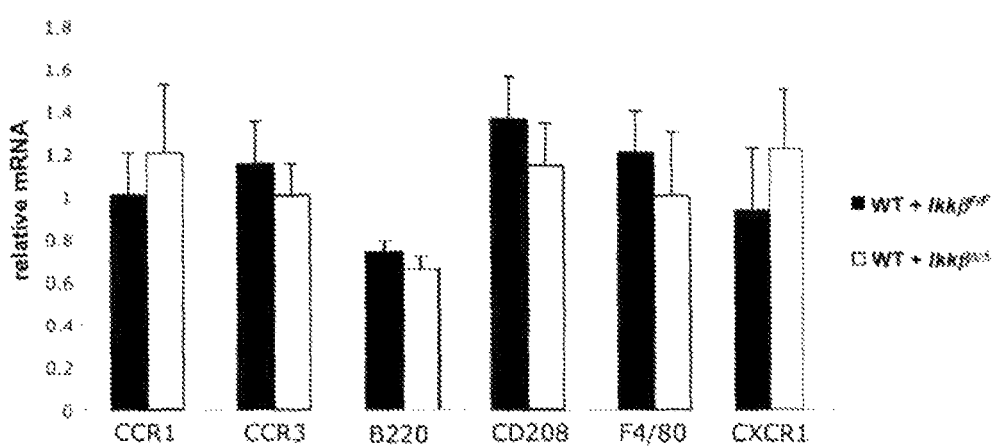
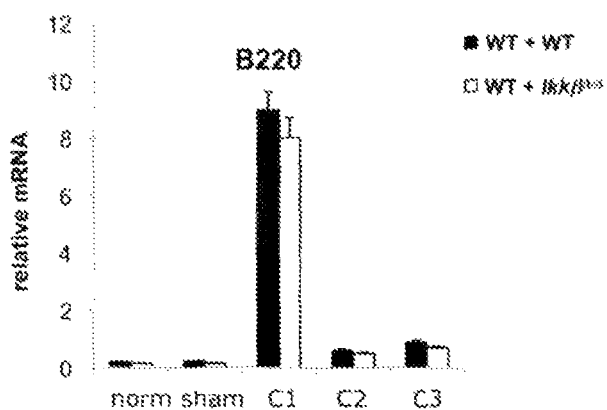

Figure 32
A.
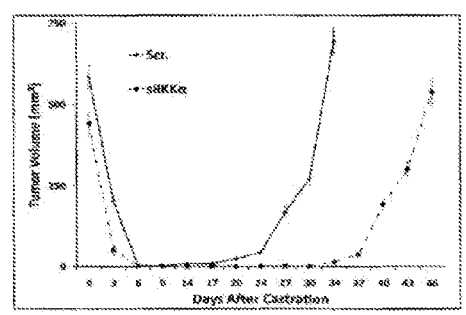
B.
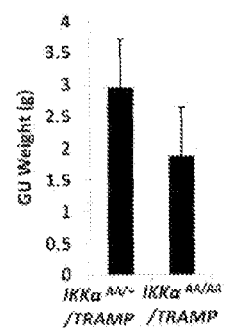
C.
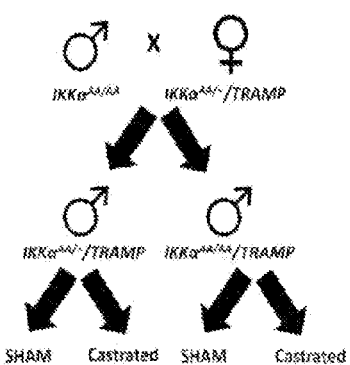
D.
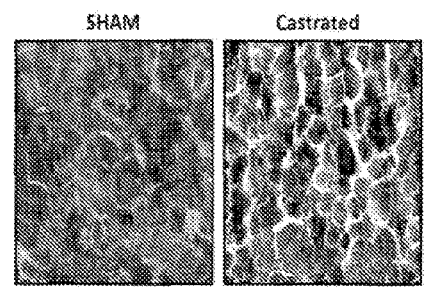
E.
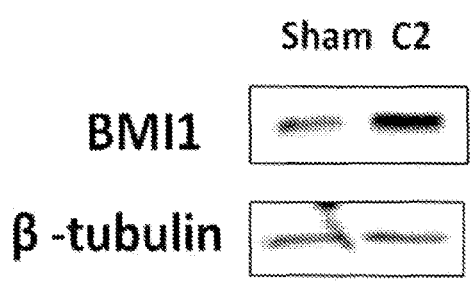
F.
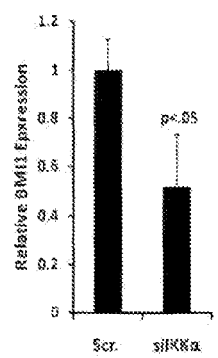

Figure 34
A.
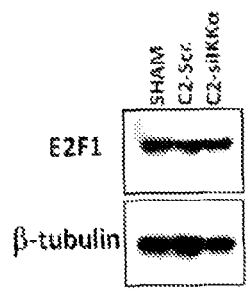
B.
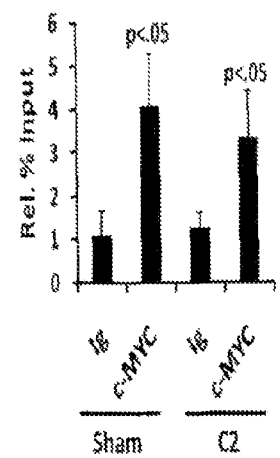
C.
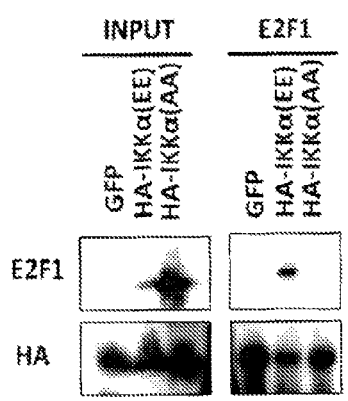
D.
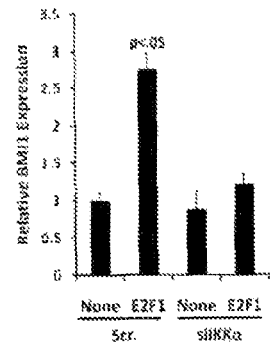
E.
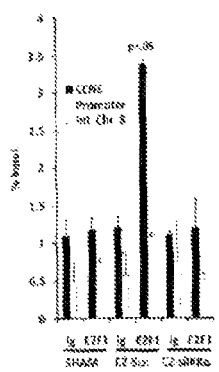
F.
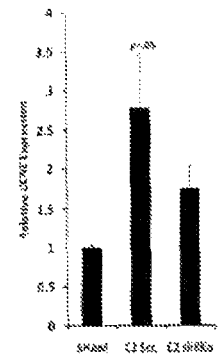

Mouse INK4a/ARF Locus

Figure 36
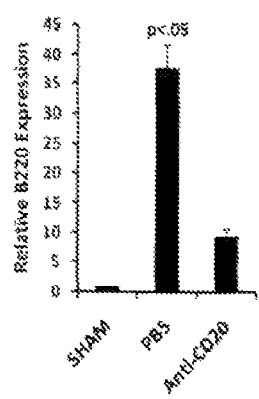
A.
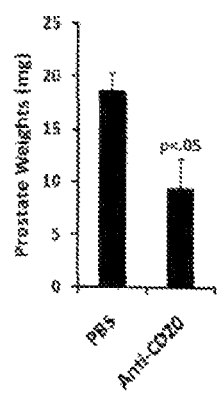
B.
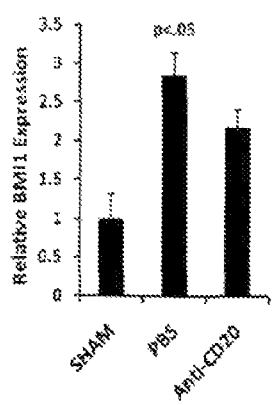
C.

METHODS FOR TREATING CASTRATION RESISTANT PROSTATE CANCER AND METASTASIS BY REDUCING B-CELL NUMBER AND/OR FUNCTION

CROSS-REFERENCE TO OTHER APPLICATIONS

This international application claims priority to U.S. provisional Application Ser. No. 61/438,052, filed Jan. 31, 2011, the contents of which are incorporated by reference in their entirety.

GOVERNMENT INTEREST

This invention was made with government support under grant No. R01 CA127923-01 awarded by National Institutes of Health. The government has certain rights in the invention.

FIELD OF THE INVENTION

The invention provides methods for reducing growth and/or metastasis of androgen-independent (castration resistant) prostate cancer in a tissue in an animal. In one embodiment the method comprises administering to the animal a therapeutically effective amount of a compound that reduces the number of B cells, and/or the function of B cells, in the tissue. In yet another embodiment, the invention provides methods for reducing androgen-induced growth of prostate epithelial cells in prostate tissue in an animal. In one embodiment, the method comprises administering to the animal a therapeutically effective amount of a compound that reduces the number of B cells, and/or the function of B cells, in the tissue.

BACKGROUND OF THE INVENTION

Prostate cancer (CaP) progresses from prostatic intraepithelial neoplasia through locally invasive adenocarcinoma to castration resistant (CR) metastatic carcinoma[1]. Although radical prostatectomy, radiation and androgen ablation are effective therapies for androgen-dependent (AD) CaP, metastatic CR-CaP is a major complication with high mortality[2]. Androgens stimulate growth and survival of prostate epithelium and early CaP. Although most patients initially respond to androgen ablation, many develop CR-CaP within 12-18 months[2]. Despite extensive studies, the mechanisms underlying CR-CaP emergence remain poorly understood and their elucidation is critical for development of improved therapies. Curiously, CR-CaP remains androgen receptor (AR) dependent and potent AR antagonists induce tumor regression in castrated mice[3]. The role of inflammation in CR-CaP has not been addressed, although it was reported that intrinsic NF-κB activation supports its growth[4]. Inflammation is a localized protective reaction to injury or infection, but it also has a pathogenic role in many diseases, including cancer[5]. Whereas acute inflammation is critical for host defense, chronic inflammation contributes to tumorigenesis and metastatic progression. The inflammation-responsive IκB kinase (IKK) β and its target NF-κB have important tumor promoting functions within malignant cells and inflammatory cells[6]. The latter, including macrophages and lymphocytes, are important elements of the tumor microenvironment[7-9], but the mechanisms underlying their recruitment remain obscure, although thought to depend on chemokine and cytokine production[10].

Currently, the common way of treating primary non-metastatic prostate cancer entails treatment with anti-androgen drugs (so called chemical castration). In addition, surgical removal or radioablation are also practiced. While these procedures are effective, a major problem is the re-emergence of androgen independent cancer a few years later. Thus, what are needed are methods to reduce (including delay and/or complete inhibition of) the re-emergence of hormone resistant cancer, and/or regeneration of normal tissue.

SUMMARY OF THE INVENTION

The invention provides a method for reducing one or more of (a) growth of castration resistant prostate cancer (CaP) cells in a tissue and (b) metastasis of castration resistant prostate cancer (CaP) cells in a tissue, in a mammalian subject in need thereof, comprising administering to the subject a therapeutically effective amount of a compound that reduces one or more of (i) the number of B cells in the tissue, and (ii) the function of B cells in the tissue. In one embodiment, the method further comprises detecting a reduction in one or more of a) growth of the castration resistant prostate cancer (CaP) cells, b) the metastasis of castration resistant prostate cancer (CaP), c) the number of the B cells in the tissue, and d) the function of the B cells in the tissue. In another embodiment, the compound reduces the number of B cells in the tissue. In a further embodiment, the compound inhibits specific binding of lymphotoxin (LT) to lymphotoxin (LT) receptor. In an alternative embodiment, the compound comprises antibody that specifically binds to lymphotoxin-β. In a further embodiment, the compound comprises LTβR-Ig. In an alternative embodiment, the compound reduces the level of expression of lymphotoxin-β. In one embodiment, compound comprises ML120B and/or IKK2 VI inhibitor. In yet another embodiment, the compound comprises an antibody that specifically binds to a B cell chemoattractant, exemplified by antibody that specifically binds to CXCL13. In a further embodiment, the compound comprises antibody that specifically binds to CD20 and/or CD19. In an alternative embodiment, the compound reduces one or more function of B cells, as exemplified by an IKKβ inhibitor, such as ML120B and/or IKK2 VI inhibitor and/or PS-1145 dihydrochloride and/or BMS-345541 and/or LC-1. In a further embodiment, the method further comprises administering to the subject STAT and/or an IKKα inhibitor. In a preferred embodiment, the subject is human. In one embodiment, prior to and/or after the step of administering, the tissue in the subject has received one or more treatment selected from the group consisting of surgery, radioablation, and treatment with an anti-androgen compound. In another embodiment, the step of administering is prior to and/or after detecting a symptom of one or more of (a) the growth of castration resistant prostate cancer (CaP) cells in the tissue, and (b) the metastasis of castration resistant prostate cancer (CaP) cells in a tissue.

The invention also provides a method for reducing androgen-induced growth of prostate epithelial cells in a mammalian subject in need thereof, comprising administering to the subject a therapeutically effective amount of a compound that reduces one or more of (i) the number of B cells in the tissue, and (ii) the function of B cells in the tissue. In one embodiment, the method further comprises detecting a reduction in one or more of a) androgen-induced growth of the prostate epithelial cells, b) the number of B cells in the tissue, and c) the function of B cells in the tissue. In another embodiment, the compound reduces the number of B cells in the tissue. In a further embodiment, the compound inhibits specific binding of lymphotoxin (LT) to lymphotoxin (LT) receptor. In an alternative embodiment, the compound comprises antibody that specifically binds to lymphotoxin-β. In a further embodiment, the compound comprises LTβR-Ig. In an alternative embodiment, the compound reduces the level of expression of lymphotoxin-β. In one embodiment, compound comprises ML120B and/or IKK2 VI inhibitor. In yet another embodiment, the compound comprises an antibody that specifically binds to a B cell chemoattractant, exemplified by antibody that specifically binds to CXCL13. In a further embodiment, the compound comprises antibody that specifically binds to CD20 and/or CD19. In an alternative embodiment, the compound reduces one or more function of B cells, as exemplified by an IKKβ inhibitor, such as ML120B and/or IKK2 VI inhibitor and/or PS-1145 dihydrochloride and/or BMS-345541 and/or LC-1. In a further embodiment, the method further comprises administering to the subject STAT and/or an IKKα inhibitor. In a preferred embodiment, the subject is human. In one embodiment, prior to and/or after the step of administering, the tissue in the subject has received one or more treatment selected from the group consisting of surgery, radioablation, and treatment with an anti-androgen compound. In another embodiment, the step of administering is prior to and/or after detecting a symptom of one or more of (a) the growth of castration resistant prostate cancer (CaP) cells in the tissue, and (b) the metastasis of castration resistant prostate cancer (CaP) cells in a tissue.

DEFINITIONS

The terms "reduce" and "inhibit" when in reference to the level of any molecule, and/or phenomenon (e.g., cancer, metastasis, disease symptoms, cell growth, cell death, cell apoptosis, cell viability, cell survival, cell number, B cell immune function, level of expression, level of activation of an enzyme such as IKKα and IKKβ, specific binding of an antigen to its receptor, etc.) in a first sample relative to a second sample, mean that the quantity of molecule and/or phenomenon in the first sample is lower than in the second sample by any amount that is statistically significant using any art-accepted statistical method of analysis. "Reducing" a phenomenon (e.g., cancer, metastasis, disease symptoms, cell growth, cell death, cell apoptosis, cell viability, cell survival, cell number, B cell immune function, level of expression, level of activation of an enzyme such as IKKα and IKKβ, specific binding of an antigen to its receptor, etc.) also, or in the alternative, refers to delaying, palliating, ameliorating, stabilizing, preventing and/or reversing the phenomenon and/or one or more symptoms associated with the phenomenon. In one embodiment, the reduction may be determined subjectively, for example when a patient refers to their subjective perception of disease symptoms, such as pain, nausea, tiredness, etc. In another embodiment, the quantity of molecule, cell, and/or phenomenon in the first sample (or in the first subject) is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in the second sample (or in the second subject). In one embodiment, the first sample (or the first subject) is exemplified by, but not limited to, a sample (or subject) that has been manipulated using the invention's compositions and/or methods. In a further embodiment, the second sample (or the second subject) is exemplified by, but not limited to, a sample (or subject) that has not been manipulated using the invention's compositions and/or methods. In an alternative embodiment, the second sample (or the second subject) is exemplified by, but not limited to, a sample (or subject) that has been manipulated, using the invention's compositions and/or methods, at a different dosage and/or for a different duration and/or via a different route of administration compared to the first subject. In one embodiment, the first and second samples (or subjects) may be the same, such as where the effect of different regimens (e.g., of dosages, duration, route of administration, etc.) of the invention's compositions and/or methods is sought to be determined on one sample (or subject). In another embodiment, the first and second samples (or subjects) may be different, such as when comparing the effect of the invention's compositions and/or methods on one sample (subject), for example a patient participating in a clinical trial and another individual in a hospital. As used herein the terms "therapeutically effective amount" and "protective amount" of a composition with respect to prostate cancer refer to, in one embodiment, an amount of the composition that delays, reduces, palliates, ameliorates, stabilizes, prevents and/or reverses one or more symptoms of prostate cancer compared to in the absence of the composition of interest. Examples include, without limitation, primary and/or metastatic tumor size, primary and/or metastatic tumor number, pain, nausea, weight loss, etc. Specific dosages can be readily determined by clinical trials and depend, for example, on the route of administration, patient weight (e.g. milligrams of drug per kg body weight). Moreover, the dosage range for anti-B cell compounds, such as rituximab, ocrelizumab and ofatumumab antibodies (for which there is ample clinical trial information) provides a good working dose, from which one of skill in the art may increase or decrease the dose based on effectiveness. The term "delaying" symptoms refers to increasing the time period between exposure to the compound and the onset of one or more symptoms of the disease. The term "eliminating" symptoms refers to 100% reduction of one or more symptoms of the disease.

The term "administering" a compound to an animal includes introducing the compound prophylactically (i.e., before the observation of one or more disease symptoms) and/or therapeutically (i.e., after the observation of one or more disease symptoms). Administration also may be concomitant with (i.e., at the same time as, or during) manifestation of one or more disease symptoms. Also, the invention's compounds may be administered before, concomitantly with, and/or after administration of another type of drug or therapeutic procedure (e.g., surgery such as castration, chemotherapy, radiotherapy, etc.). Methods of administering the invention's compounds include, without limitation, administration in parenteral, oral, intraperitoneal, intranasal, topical (e.g., rectal), and sublingual forms. Parenteral routes of administration include, for example, subcutaneous, intravenous, intramuscular, intrastemal injection, and infusion routes.

An "anti-B cell" compound is a compound that reduces the number of B cells, the recruitment of B cells, and/or the immune function of B cells.

"Mammalian subject" and "mammalian animal" interchangeably refer to any mammal (e.g., humans, non-human primates, murines, ovines, bovines, ruminants, lagomorphs, porcines, caprines, equines, canines, felines, ayes, guinea pig, hamster, ferret, chinchilla, mouse, cotton rat, etc.).

"Castration resistant prostate cancer," "CaP," "androgen-receptor dependent prostate cancer," "androgen-independent prostate cancer," are used interchangeably to refer to prostate cancer in which prostate cancer cells "grow" (i.e., increase in number) in the absence of androgens and/or in the absence of expression of androgen receptors on the cancer cells.

"Metastasis" refers to the processes by which a cancer cell is translocated from a primary cancer site (i.e., a location where the cancer cell initially formed from a normal, hyperplastic or dysplastic cell) to a site other than the primary site, where the translocated cell lodges and proliferates. "metastasis" also refers to the cancer that is located at a site other than the primary cancer site.

"B cell function" refers to the level of expression of lymphotoxin on the cell surface of B cells. Thus, reducing the function of B cells refers to reducing the level of expression of lymphotoxin on the cell surface of B cells.

"B cell chemoattractant" refers to a compound that directs the movement of B cells in the direction of the compound, and is exemplified by CXCL13.

"CXCL13" refers to "C—X—C motif chemokine 13" also known as B lymphocyte chemoattractant (BLC), and is a small cytokine that in humans is encoded by the CXCL13 gene. CXCL13 belongs to the CXC chemokine family, and is selectively chemotactic for B cells belonging to both the B-1 and B-2 subsets, and elicits its effects by interacting with chemokine receptor CXCR5.

"Specifically binds" and "specific binding" when made in reference to the binding of antibody to a molecule (e.g., peptide) or binding of a cell (e.g., T-cell) to a peptide, refer to an interaction of the antibody or cell with one or more epitopes on the molecule where the interaction is dependent upon the presence of a particular structure on the molecule. For example, if an antibody is specific for epitope "A" on the molecule, then the presence of a protein containing epitope A (or free, unlabeled A) in a reaction containing labeled "A" and the antibody will reduce the amount of labeled A bound to the antibody. In one embodiment, the level of binding of an antibody to a molecule is determined using the "IC50" i.e., "half maximal inhibitory concentration" that refer to the concentration of a substance (e.g., inhibitor, antagonist, etc.) that produces a 50% inhibition of a given biological process, or a component of a process (e.g., an enzyme, antibody, cell, cell receptor, microorganism, etc.). It is commonly used as a measure of an antagonist substance's potency.

"Lymphotoxin" ("LT"), also called tumor necrosis factor-β (TNF-β) is a lymphokine released by antigen-stimulated lymphocytes, particularly cytotoxic T lymphocytes.

"Lymphotoxin receptor," "LT receptor" and "LTβR" interchangeably refer to a receptor that is expressed on the surface of most cell types, including cells of epithelial and myeloid lineages, but not on T and B lymphocytes. LT receptor specifically binds the lymphotoxin membrane form (a complex of lymphotoxin-alpha and lymphtoxin-beta).

"LTβR-Ig" is a fusion protein containing lymphotoxin receptor (LTβR) that is known to bind to the ligands LTα/β heterotrimer and LIGHT (homologous to lymphotoxins.

"STAT" and "signal transducer and activator of transcription 3" is also known as "(acute-phase response factor," "APRF," "APRF Transcription Factor," "DNA-binding protein APRF," "IL6-Response Factor," and "LIF (leukemia inhibitory factor)-Response Factor." STAT is a transcription factor encoded by a family of genes known as the STAT genes.

"ML120B" refers to N-(6-chloro-7-methoxy-9H-β-carbolin-8-yl)-2-methylnicotinamide (ML120B), a β-carboline derivative.

"IKK2 VI inhibitor" refers to (5-Phenyl-2-ureido)thiophene-3-carboxamide.

"PS-1145 dihydrochloride" refers to N-(6-Chloro-9H-pyrido[3,4-b]indol-8-yl)-3-pyridinecarboxamide dihydrochloride, and is commercially available (Sigma-Aldrich).

"BMS-345541" refers to N-(1,8-Dimethylimidazo[1,2-a]quinoxalin-4-yl)-1,2-Ethanediamine monohydrochloride, and is commercially available (Sigma-Aldrich).

"IKKβ" is also known as inhibitor of nuclear factor kappa-B kinase subunit beta ("NFκB"). IKKβ is a kinase of the IKK family. It phosphorylates inhibitors of NFκB, leading to the dissociation of the inhibitor/NFκB complex and ultimately the degradation of the inhibitor. It is preferentially found as a heterodimer with IKKα but also as a homodimer. IKKβ is an enzyme that serves as a protein subunit of IκB kinase, which is a component of the cytokine-activated intracellular signaling pathway involved in triggering immune responses. IKKβ is found on the internal side of the plasma membrane, in the cytoplasm, as part of IκB kinase complex, and in the nucleus. IKKβ functions include protein serine/threonine kinase activity, protein binding activity, IκB kinase activity, nucleotide binding activity, ATP binding activity, and protein kinase activity. IKKβ protein in humans is encoded by the IKBKB (inhibitor of kappa light polypeptide gene enhancer in B-cells, kinase beta) gene.

"IKKβ inhibitor" refers to a compound that reduces one or more IKKβ function (e.g., protein serine/threonine kinase activity, protein binding activity, IκB kinase activity, nucleotide binding activity, ATP binding activity, and protein kinase activity.

"Activation of IKKβ" refers to phosphorylation, e.g., by a kinase, of one or more IKKβ serine residues within the IKKβ activation loop.

"IKKα" is a kinase of the IKK family. It phosphorylates inhibitors of NFκB, leading to their dissociation from NFκB and ultimately to their degradation. It is located on the internal side of plasma membrane, on intracellular membrane-bound organdies, in the cytoplasm, nucleolus, and as part of IκB kinase complex. IKKα functions in protein binding, has IκB kinase activity, nucleotide binding activity, ATP binding activity, and protein kinase activity. IKKα is encoded by the CHUK gene.

"IKKα inhibitor" refers to a compound that reduces one or more IKKα function (e.g., protein binding, IκB kinase activity, nucleotide binding activity, ATP binding activity, and protein kinase activity.

"Activation of IKKα" refers to phosphorylation, e.g., by a kinase, of one or more IKKα serine residues within the IKKα activation loop.

"CD20" and "B-lymphocyte antigen CD20" interchangeably refer to an activated-glycosylated phosphoprotein expressed on the surface of B-cells beginning at the pro-B phase (CD45R+, CD117+) and progressively increasing in concentration until maturity. In humans CD20 is encoded by the MS4A1 gene.

"Anti-androgen," "antiandrogen" and "androgen antagonist" interchangeably refer to compounds that prevent androgens from expressing their biological effects on responsive tissues, by blocking the appropriate receptors, competing for binding sites on the cell's surface, and/or affecting androgen production. Antiandrogens are prescribed to treat an array of diseases, such as prostate cancer, and are exemplified by the drugs flutamide (brand name Eulexin™), nilutamide (brand names Anandron™ and Nilandron™), bicalutamide (brand name Casodex™), finasteride (brand names Proscar™ and Propecia™), dutasteride (brand name Avodart™), bexlosteride, izonsteride, turosteride, and episteride.

"Radioablation" is a medical procedure where part of the electrical conduction system of a tissue (e.g., tumor, heart, or other dysfunctional tissue) is ablated using the heat generated from the low frequency AC, pulses of DC, or high frequency alternating current to treat a medical disorder. Radio frequency ablation (RFA) uses high frequency alternating current and has the advantage over previously used low frequency AC or pulses of DC in that it does not directly stimulate nerves or heart muscle and can therefore often be used without the need for general anesthetic.

DESCRIPTION OF THE DRAWINGS

FIG. 16. Deletion of IKKβ in bone marrow derivatives has no effect on infiltration of leukocytes into androgen-deprived tumors. Myc-CaP tumors were established in lethally irradiated FVB males that were reconstituted with Ikkβ$^{F/F}$ or Ikkβ$^{Δ/Δ}$ BM. Ikkβ$^{F/F}$ and Ikkβ$^{Δ/Δ}$ chimeras were injected with poly(IC) as described above prior to castration. A. One week after castration, tumor samples were collected and total RNA was isolated and expression of indicated cell marker and chemokine receptor mRNAs was quantitated by Q-PCR and normalized to that of cyclophilin A mRNA. Results are averages±s.d. (n=6). B. Tumor samples were collected as above from non-operated (norm), sham operated and castrated mice and expression of B220 mRNA was quantitated as above. Results are averages±s.d. (n=5).

FIG. 32: Role of IKKα in castration resistance and BMI1 expression. A) myc-CaP tumors were generated by s.c. transplantation of mock (Scr.) or IKKα-silenced cells into wild-type mice. When tumors reached 500 mm$^3$ in size, the mice were castrated. Tumor volume was then measured at the indicated time points. B) GU weights of 24 weeks old sham operated Ikkα$^{AA/+}$/TRAMP and Ikkα$^{AA/AA}$/TRAMP mice. C) Experimental design of producing CR-PCa in TRAMP mice. All castrations were performed at 12 weeks of age and the prostates were analyzed at 24 weeks. D) Paraffin sections of prostates collected 12 weeks after sham operation or castration from Ikkα$^{AA/+}$/TRAMP mice were analyzed by immunohistochemistry for IKKα expression. E) Lysates of s.c. myc-CaP tumors collected 2 weeks after castration or sham operation were analyzed for Bmi1 expression by immunoblotting. F) s.c. myc-CaP tumors formed from mock (Scr.) or IKKα-silenced cells 2 weeks after castration were enriched for epithelial cells. RNA was then collected and analyzed for Bmi1 expression. In panels B and F, the values represent means±SD (n=3).

FIG. 34: IKKα activity is required for E2F1 recruitment to the Bmi1 and Gene promoters. A) Protein extracts from mock-(Scr.) or IKKα-silenced tumors were analyzed by immunoblotting for E2F1 expression 2 weeks after castration or sham operation. B) myc-CaP tumors collected 2 weeks after sham operation or castration were subjected to ChIP analysis using c-myc antibody or control IgG and primers to the Bmi1 promoter. C) 293T cells were transfected with GFP, IKKα(EE) or IKKα(AA) vectors. After 48 hrs, the cells were lysed and E2F1 was immunoprecipitated. After gel separation, immunoblotting was performed with the indicated antibodies. D) Mock- or IKKα-silenced myc-CaP cells were transduced with either an E2F1 or an empty expression vector. After 48 hrs, RNA was collected and Bmi1 expression was analyzed. E) myc-CaP tumors generated by s.c. transplantation of mock- or IKKα-silenced cells were collected 2 weeks after sham operation or castration and subjected to ChIP analysis with either E2F1 antibody or control IgG and CCNE promoter primers. F) myc-CaP tumors formed by mock (Scr.)- or IKKα-silenced cells were collected 2 weeks after castration or sham operation. RNAs were extracted and analyzed for CCNE1 expression. In panels B and D-F, the values represent means±SD (n=3).

FIG. 36: B cell depletion with anti-CD20 attenuates androgen-induced regrowth of the normal prostate. A) RNA collected from prostates 17 days after castration and subsequent androgen replacement of mice injected with 250 ug of anti-CD20 or PBS control every 4 days following castration were analyzed for B220 expression. B) Prostate weights of the mice described above. C) RNAs described above were analyzed for Bmi1 expression. All values represent means s±SD (n=3).

BRIEF DESCRIPTION OF THE INVENTION

Figure 1:
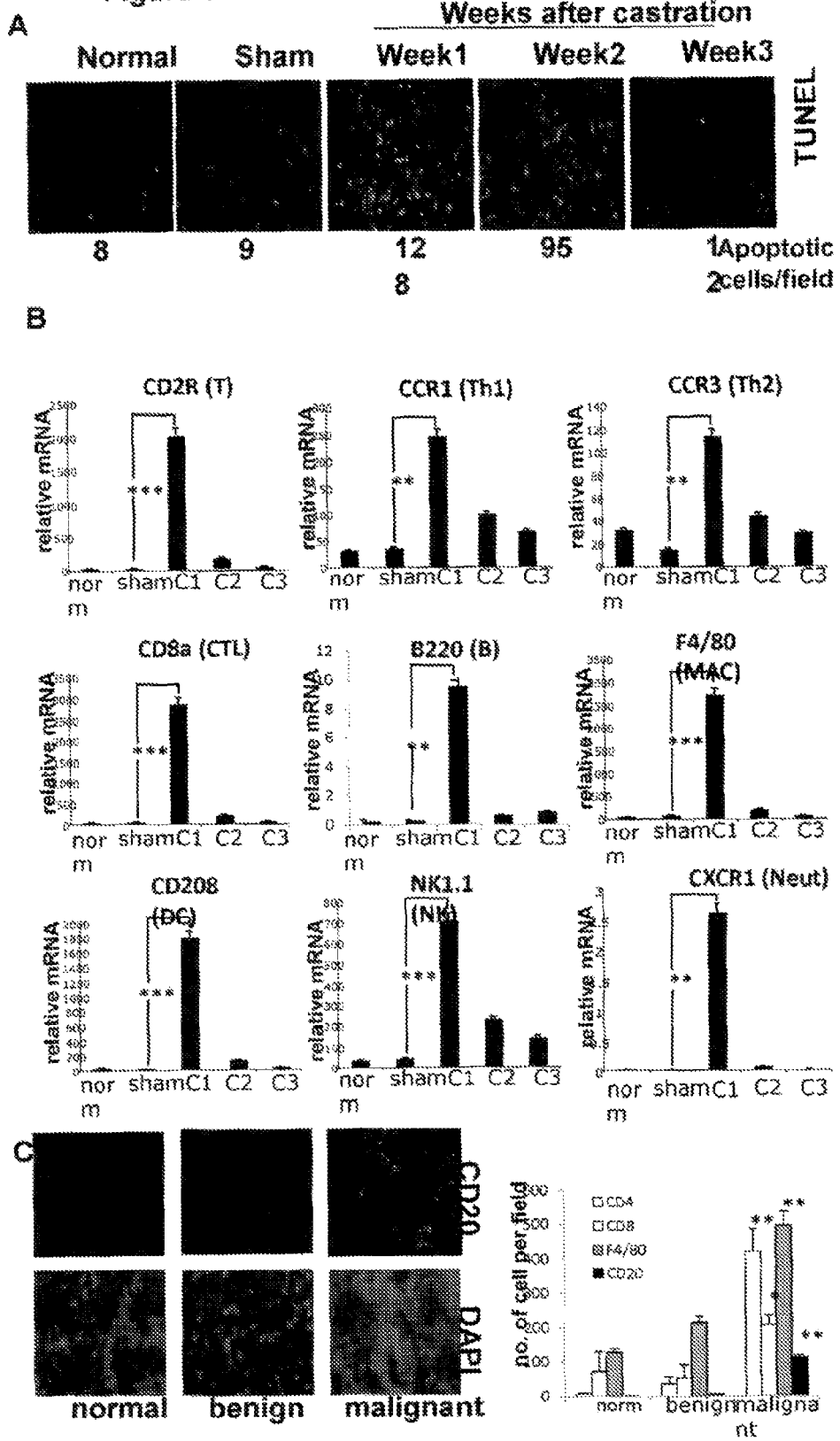
FIG. 1. Androgen ablation induces tumor inflammatory infiltration. Six week old FVB males (n=10) were inoculated with myc-CaP cells. When tumors reached 1000 mm$^3$, mice were left untreated, castrated or sham operated. Tumors were collected when indicated for analysis. A. Paraffin-embedded tumor sections were TUNEL stained to determine apoptotic cell frequency (results are averages, n=3). B. Total RNA was isolated from tumor samples and expression of indicated cell marker mRNAs was quantitated and normalized to that of cyclophilin A (norm=normal, C1,2,3=mice analyzed 1,2,3 weeks after castration, sham=sham-operated). Results are averages±s.d. (n=10). C. Frozen human prostate sections (normal tissue (n=3), prostatic hyperplasia (n=3), and malignant CaP with Gleason scores 6-8 (n=10)) were stained with CD4, CD8 and CD20 antibodies and DAN and analyzed by immunofluorescent microscopy. The histogram denotes average frequencies of indicated cell types (n=3 per sample). P values were determined and are depicted as insignificant (ns), significant (*), very significant () or highly significant (*).

The invention provides methods for reducing growth and/or metastasis of androgen-independent (castration resistant) prostate cancer in a tissue in an animal. In one embodiment the method comprises administering to the animal a therapeutically effective amount of a compound that reduces the number of B cells, and/or the function of B cells, in the tissue. In yet another embodiment, the invention provides methods for reducing androgen-induced growth of prostate epithelial cells in prostate tissue in an animal. In one embodiment, the method comprises administering to the animal a therapeutically effective amount of a compound that reduces the number of B cells, and/or the function of B cells, in the tissue.

The invention provides the unexpected discovery that B cells are needed for the regrowth of castration resistant prostate cancer and for androgen-induced regeneration of normal prostate cells. Data herein demonstrate that interventions that block B cell recruitment into the tumors and/or cause B cell ablation and/or loss of B cell function can inhibit growth of castration resistant cancer. For example, data herein demonstrate that genetic ablation of B cells, B cell ablation with anti-CD20 antibody, and inhibition of B cell recruitment into tumors, inhibit the growth of castration resistant cancer and prevent androgen-induced regeneration of the prostate. Thus, the invention provides a new B cell-targeted approach to the prevention and/or treatment of castration resistant prostate cancer, the second leading cause of cancer deaths in American men.

The invention prevents or significantly delays the re-emergence of androgen-resistant prostate cancer after treatment with anti-androgens or surgical removal or radioablation of primary prostate cancer.

Currently, the common way of treating primary non-metastatic prostate cancer entails treatment with anti-androgen drugs (so called chemical castration). In addition, surgical removal or radioablation are also practiced. While these procedures are effective, a major problem is the re-emergence of androgen independent cancer a few years later. The invention delays the re-emergence of hormone resistant cancer. Several anti-B cells drugs that have been approved for clinical use may be used in the invention's methods. As prostate cancer is normally found in old men, even delay of several years in disease re-emergence is significant.

The invention is further described under (A) Reducing growth and/or metastasis of castration resistant prostate cancer (CaP), and (B) Regeneration of normal prostate tissue.

A. Reducing Growth and/or Metastasis of Castration Resistant Prostate Cancer (CaP)

CR-CaP is a major complication that limits the success of androgen ablation therapy and is responsible for most prostate cancer mortality[2]. Data herein in Examples 1-8 show that CaP progression is associated with inflammatory infiltration and activation of IKKα, which stimulates metastasis by an NF-κB-independent, cell autonomous, mechanism[11]. Data herein in Examples 1-8 also show that androgen ablation causes infiltration of regressing AD tumors with leukocytes, including B cells, in which IKKβ activation results in production of cytokines that activate IKKα and STAT3 in CaP cells to enhance hormone-free survival.

Thus, in one embodiment, the invention provides a method for reducing one or more of (a) growth of castration resistant prostate cancer (CaP) cells in a tissue and (b) metastasis of castration resistant prostate cancer (CaP) cells in a tissue, in a mammalian subject in need thereof, comprising administering to the subject a therapeutically effective amount of a compound that reduces one or more of (i) the number of B cells in the tissue, and (ii) the function of B cells in the tissue (Examples 1-8). In one embodiment, the method further comprising detecting a reduction in one or more of a) growth of the castration resistant prostate cancer (CaP) cells, b) the metastasis of castration resistant prostate cancer (CaP), c) the number of the B cells in the tissue, and d) the function of the B cells in the tissue.

In one embodiment, the compound reduces the number of B cells in the tissue, such as by B cell ablation. In a particular embodiment, the compound inhibits specific binding of lymphotoxin (LT) to lymphotoxin (LT) receptor. Preferably, the compound comprises antibody that specifically binds to lymphotoxin-P. In one embodiment, the compound comprises LTβR-Ig.

In a further embodiment, compound that reduces the number of B cells in the tissue, functions in reducing the level of expression of lymphotoxin-β. In a further embodiment, the compound that reduces the number of B cells in the tissue comprises an antibody that specifically binds to a B cell chemoattractant, exemplified by antibody that specifically binds to CXCL13.

In a further embodiment, the compound that reduces the number of B cells in the tissue comprises and antibody. Antibodies that are useful in the invention, such as antibodies that specifically bind to CD20 and/or specifically bind to lymphotoxin-β, and/or specifically bind to a B cell chemoattractant (such as CXCL13), include polyclonal antibodies, monoclonal antibodies, chimeric antibodies, recombinant antibodies, humanized antibodies, and antibodies displayed upon the surface of a phage. Also contemplated are antibody fragments that contain the idiotype ("antigen-binding fragment") of the antibody molecule. Examples of such fragments include, but are not limited to, the Fab region, F(ab')2 fragment, Fc' fragment, and Fab' fragments.

In a particular embodiment, the antibody specifically binds to CD20, as exemplified by rituximab antibody (sold under the trade names Rituxan™ and MabThera™ and is a chimeric monoclonal anti-CD20 antibody, that is found primarily on the surface of B cells), ocrelizumab antibody (which is a humanized anti-CD20 monoclonal antibody), and Ofatumumab (also known as (HuMax-CD20) and is a fully human anti-CD20 antibody).

Antibody treatment of human beings with cancer is known in the art, for example in U.S. Pat. Nos. 5,736,137; 6,333,410; 5,475,092; 5,585,499; 5,846,545; 7,202,346; 6,340,701; 6,372,738; 7,202,346; 5,846,545; 5,585,499; 5,475,092; 7,202,346; 7,662,387; 7,662,387; 6,429,295; 7,666,425; 5,057,313. antibodies may be administered with pharmaceutically acceptable carriers, diluents, and/or excipients. Examples of suitable carriers, diluents and/or excipients include Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose.

In one embodiment, the invention's compositions comprise a lipid for delivery as liposomes. Methods for generating such compositions are known in the art (Borghouts et al. (2005). J Pept Sci 11, 713-726; Chang et al. (2009) PLoS One 4, e4171; Faisal et al. (2009) Vaccine 27, 6537-6545; Huwyler et al. (2008) Int J Nanomedicine 3, 21-29; Song et al. (2008) Int J Pharm 363, 155-161; Voinea et al. J Cell Mol Med 6, 465-474).

The invention's compositions are administered in a "therapeutic amount." The terms "therapeutic amount," "pharmaceutically effective amount," "therapeutically effective amount," "biologically effective amount," and "protective amount" are used interchangeably herein to refer to an amount that is sufficient to achieve a desired result, whether quantitative and/or qualitative. In particular, a therapeutic amount is that amount that delays, reduces, palliates, ameliorates, stabilizes, prevents and/or reverses one or more symptoms of the disease (e.g., prostate cancer, prostate cancer metastasis, etc.) compared to in the absence of the composition of interest. Examples include, without limitation, tumor size and/or tumor number in cancer disease, biochemical tissue function tests, etc.

Specific "dosages" of a "therapeutic amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to achieve optimal efficacy but will depend on such factors as weight, diet, concurrent medication and other factors, which those skilled in the art will recognize. The dosage amount and frequency are selected to create an effective level of the compound without substantially harmful effects.

For example, in therapeutic antibody applications, when present in an aqueous dosage form, rather than being lyophilized, the antibody typically will be formulated at a concentration of about 0.1 mg/ml to 100 mg/ml. Depending on the type and severity of the disease, about 0.015 to 15 mg of antibody/kg of patient weight is an initial candidate dosage for administration to the patient, whether, for example, by one or more separate administrations, or by continuous infusion. For repeated administrations over several days or longer, depending on the condition, the treatment is repeated until a desired suppression of disease symptoms occurs.

In one embodiment, the compound reduces one or more function of B cells, as exemplified by IKKβ inhibitors ML120B and IKK2 VI inhibitor, as well as by non-steroidal anti-inflammatory drugs (nSAIDs) or TNF inhibitors such as curcumin or cannabis.

In some embodiments, the invetnion's methods further comprise administering STAT3 and/or an IKKα inhibitor to the mammal.

In some embodiments, prior to and/or after administering to the subject a compound that reduces the number of B cells in the tissue, and/or the function of B cells in the tissue, it may be desirable to for the subject to receive one or more treatment such as surgery, radioablation, and treatment with an anti-androgen compound.

In some embodiments, the subject is treated with the compound that reduces the number of B cells in the tissue and/or the function of B cells, prior to and/or after detecting a symptom of growth of castration resistant prostate cancer (CaP) cells in the tissue, and/or detecting metastasis of castration resistant prostate cancer (CaP) cells in a tissue.

The invention's compositions and methods are also useful for a subject "in need of reducing one or more symptoms of" a disease includes a subject that exhibits and/or is at risk of exhibiting one or more symptoms of the disease. For Example, subjects may be at risk based on family history, genetic factors, environmental factors, etc. This term includes animal models of the disease. Thus, administering a composition (which reduces a disease and/or which reduces one or more symptoms of a disease) to a subject in need of reducing the disease and/or of reducing one or more symptoms of the disease includes prophylactic administration of the composition (i.e., before the disease and/or one or more symptoms of the disease are detectable) and/or therapeutic administration of the composition (i.e., after the disease and/or one or more symptoms of the disease are detectable). The invention's compositions and methods are also useful for a subject "at risk" for disease refers to a subject that is predisposed to contracting and/or expressing one or more symptoms of the disease. This predisposition may be genetic (e.g., a particular genetic tendency to expressing one or more symptoms of the disease, such as heritable disorders, etc.), or due to other factors (e.g., environmental conditions, exposures to detrimental compounds, including carcinogens, present in the environment, etc.). The term subject "at risk" includes subjects "suffering from disease," i.e., a subject that is experiencing one or more symptoms of the disease. It is not intended that the present invention be limited to any particular signs or symptoms. Thus, it is intended that the present invention encompass subjects that are experiencing any range of disease, from sub-clinical symptoms to full-blown disease, wherein the subject exhibits at least one of the indicia (e.g., signs and symptoms) associated with the disease.

The invention also provides a method for reducing growth and/or metastasis of castration resistant prostate cancer (CaP) cells in a tissue in a mammalian subject in need thereof, comprising administering to the subject a therapeutically effective amount of a compound that reduces the level of activation of IKKα.

B. Regeneration of Normal Prostate Tissue

Inflammation triggered by tissue injury may cause epigenetic changes that promote regeneration or tumor development, but mechanistic links between these processes are missing from the prior art.

A link between inflammation and cancer was proposed (Balkwill and Mantovani, 2001). In the past decade, studies using mouse models of human cancer have illustrated several key mechanisms that link inflammation to tumor development and progression (Grivennikov et al., 2011). Quite frequently, inflammatory signals, mainly cytokines, produced by immune cells within the tumor microenvironment lead to paracrine activation of transcription factors, such as NF-κB and STAT3, within pre-malignant cells, thereby enhancing survival and proliferation of cancer progenitors. Usually, this crosstalk does not involve irreversible genetic changes, although oncogenic mutations can result in upregulation of chemokine gene expression in malignant cells, thus promoting establishment of a pro-tumorigenic inflammatory microenvironment (Karin, 2005). Nonetheless, chronic inflammation may also enhance tumor initiation and/or malignant progression through induction of oncogenic mutations, chromosomal instability and epigenetic changes (Hussain and Harris, 2007). The mechanisms and pathways through which inflammation elicits epigenetic changes that contribute to tumor development and progression are unknown. Inflammation is also of importance in wound repair and tissue regeneration and it has been pointed out that tumors are analogous to wounds that do not heal (Dvorak, 1986). Furthermore, signaling pathways that play a major role in tissue regeneration and stem cell renewal, namely the Wnt and Hedgehog pathways, are also key players in tumorigenesis (Beachy et al., 2004). However, it is unknown whether and how Wnt and Hedgehog signaling are activated in response to inflammatory signals generated by tissue injury. It is also not clear how tissue injury leads to stem cell activation.

Another signaling pathway involved in inflammation, tissue repair and cancer is the NF-κB pathway (Ben-Neriah and Karin, 2011). To study roles of NF-κB transcription factors in cancer, we have focused our studies on components of the IκB kinase (IKK) complex, namely the IKKα and IKKβ catalytic subunits (Karin, 2009). While both kinases can activate NF-κB-mediated transcription, IKKα also has NF-κB-independent functions in development (Descargues et al., 2008; Hu et al., 1999; Hu et al., 2001) and tumorigenesis (Ammirante et al., 2010; Luo et al., 2007; Marinari et al., 2008). NF-κB-independent activities of IKKα are particularly evident in prostate cancer (PCa), the most common non-skin cancer in men. Currently, PCa results in over 30,000 deaths each year in the US—making it the second leading cause of cancer deaths in men (American Cancer Society, 2010). This is due to the fact that while androgen ablation or chemical castration therapy, the standard of care for PCa, is effective in the short term, the cancer will inevitably switch to a more aggressive, metastatic and eventually fatal form termed castration-resistant (CR) PCa (Gulley et al., 2003). The genesis of CR-PCa depends on emergence of PCa stem-like cells that either do not require androgen signaling for growth and survival or are highly sensitive to castrate levels of androgens (Maitland and Collins, 2008). Data herein in Examples 1-8 show that androgen ablation results in an inflammatory response, characterized by lymphocyte infiltration and production of cytokines that activate IKKα in surviving PCa cells, which accelerates the emergence of CR-PCa (Ammirante et al., 2010).

While not intending to limit the invention to a particular mechanism, in one embodiment, this castration-induced inflammatory response may be triggered by the death of androgen-deprived PCa cells, which causes the release of signals that induce expression of inflammatory chemokines by components of the tumor stroma. This leads to recruitment of a heterogeneous collection of immune cells, of which B lymphocytes are particularly important as they serve as the main source of lymphotoxin (LT), a heterodimeric member of the TNF family that activates IKKα (Ammirante et al., 2010). Data herein (Example 3) shows that ablation of B cells or inhibition of their recruitment into the regressing tumors by neutralization of the B cell chemoattractant CXCL13 prevents IKKα activation and delays CR-PCa regrowth. LT signaling leads to nuclear accumulation of IKKα, previously found to occur in human and mouse PCa, where it is required for metastatic spread but not for primary tumor growth (Luo et al., 2007). However, the molecular mechanisms by which nuclear IKKα enhances the survival and proliferation of progenitor cells that give rise to metastases and CR-PCa are not clear, although it was found that nuclear IKKα promotes metastasis through repression of the SBP5 gene, which codes for the metastasis inhibitor maspin (Luo et al., 2007). Previous studies suggested that nuclear IKKα acts as a histone H3 kinase (Anest et al., 2003; Yamamoto et al., 2003), whereas other reports have described an interaction between IKKα and the histone acetylase (HAT) CBP/p300 that results in phosphorylation of the latter (Huang et al., 2007). IKKα was also reported to regulate expression and activity of transcription factor E2F1 (Tu et al., 2006) and counteract SMRT repressor activity leading to acetylation of p65/RelA by p300 (Hoberg et al., 2006).

Data herein in Examples 9-16 demonstrate that IKKα, which accumulates in nuclei of mouse and human prostate cancer (PCa) cells, associates with E2F1 in response to inflammatory signals generated upon androgen ablation to induce transcription of the Polycomb-group gene Bmi1. Increased BMI1 expression results in histone 2A ubiquitination and repression of $p16^{Ink4a}$ and $p19^{Arf}$, leading to enhanced proliferation of PCa progenitors responsible for development of castration resistance, a severe complication of failed androgen ablation therapy. Furthermore, IKKα activation by B lymphocyte inflammatory signals is required for androgen-induced normal prostate regeneration. These findings chart a pathway that links inflammation caused by tissue injury to epigenetic changes that are critical for activation of cancer and adult tissue stem cells. Interference with this pathway augments the outcome of androgen ablation and blocks tissue regeneration.

Data herein provides the discovery of the control of CR-PCa genesis by IKKα. Specifically, in an NF-κB-independent manner, IKKα activates E2F1-driven transcription of the Bmi1 gene, coding for the polycomb group protein BMI1 which possesses histone 2A (H2A) ubiquitin ligase activity when part of Polycomb repressive complex 1 (PRC1) (Wang et al., 2004). BMI1, in turn, drives CR-PCa emergence by silencing the tumor suppressor genes p16$^{Ink4a}$ and p19$^{Arf}$ to stimulate self-renewal of putative PCa progenitors/stem cells. Recent studies highlight a role for BMI1 in proliferation of normal prostate stem cells (Lukacs et al., 2010). Data herein also identified a critical requirement for IKKα in androgen-induced regeneration of the normal prostate, which we demonstrate to be highly dependent on an injury-triggered inflammatory response similar to the one that drives CR-PCa. These results indicate that IKKα is a critical link between inflammation and PRC1-dependent epigenetic mechanisms that control the proliferation of both cancer and normal tissue stem cells. Data herein also shows a strong correlation between nuclear IKKα, BMI1 expression and presence of ubiquitinated (ubi-) H2A in human PCa specimens. These findings suggest that interference with IKKα activation would be an adjuvant to androgen ablation therapy.

Thus in one embodiment, the invention provides a method for reducing androgen-induced growth of prostate epithelial cells (including non-cancerous, normal cells) in a mammalian subject in need thereof, comprising administering to the subject a therapeutically effective amount of a compound that reduces one or more of (a) the number of B cells in the tissue, (b) the function of B cells in the tissue, and (c) the level of activation of IKKα. In some embodiments, the method further comprises detecting a reduction in one or more of a) androgen-induced growth of the prostate epithelial cells, b) the number of B cells in the tissue, c) the function of B cells in the tissue, and d) the level of activation of IKKα.

EXPERIMENTAL

The following serve to illustrate certain preferred embodiments and aspects of the present invention and are not to be construed as limiting the scope thereof.

Example 1

Methods Used in Examples 2-7

Mice were handled according to institutional and NIH guidelines. Tumors were grown in FVB mice. Where indicated, lethally irradiated FVB mice were reconstituted with BM from different strains that were backcrossed into the FVB background for at least two generations. Ltβ knockout strains were, however, in the BL6 background which does not elicit a graft vs. host response in FVB mice. Human material was obtained from the Cooperative Human Tissue Network (CHTN) along with pathology reports. Histology, gene expression and cell signaling were analyzed as described[11,25].

Mice and Cell Culture

Ikkβ$^{F/F}$ (BL6) mice were crossed to TRAMP (BL6×129) mice[31] and PB-Cre4 (BL6)[32] or Mx1-Cre (BL6) mice[33] to generate TRAMP$^{+/-}$/Ikkβ$^{+/F}$/PB-Cre4$^{+/-}$ and TRAMP$^{+/-}$/Ikkβ$^{+/F}$/PB-Cre4$^{+/+}$ or TRAMP$^{+/-}$/Ikkβ$^{+/F}$/Mx1-Cre$^{+/-}$ and TRAMP$^{+/-}$/Ikkβ$^{+/F}$/Mx1-Cre$^{+/+}$ progeny that were intercrossed with TRAMP mice for six generations. After that, TRAMP$^{+/-}$/Ikkβ$^{+/F}$/PB-Cre4$^{+/-}$ and TRAMP$^{+/-}$/Ikkβ$^{+/F}$/PB-Cre4$^{+/+}$ or TRAMP$^{+/-}$/Ikkβ$^{+/F}$/Mx1-Cre$^{+/-}$ and TRAMP$^{+/-}$/Ikkβ$^{+/F}$/Mx1-Cre$^{+/+}$ mice were intercrossed to generate TRAMP$^{+/-}$/Ikkβ$^{F/F}$/PB-Cre4$^{+/-}$, TRAMP$^{+/-}$/Ikkβ$^{F/F}$/PB-Cre4$^{+/+}$, TRAMP$^{+/-}$/Ikkβ$^{F/F}$/Mx1-Cre$^{+/-}$ and TRAMP$^{+/-}$/Ikkβ$^{F/F}$/Mx1Cre$^{+/+}$ mice. Only male littermates were used. FVB, Tcrβ$^{-/-}$δ$^{-/-}$ (BL6), Mx1-Cre and Rag1$^{-/-}$ (BL6×129) mice were from the Jackson Laboratory. J$_H$$^{-/-}$ mice (FVB) were kindly provided by L. Coussens (Cancer Research Institute and Anatomic Pathology, UCSF, San Francisco, Calif.). Bone marrow from B-Ltβ$^{-/-}$ or T-Ltβ$^{-/-}$ mice[21] was kindly provided by C.F. Ware (La Jolla Institute for Allergy and Immunology, La Jolla, Calif.). PB-Cre4 and TRAMP mice were from MMHCC (Mouse Models of Human Cancer Consortium). Mice were maintained under specific pathogen-free conditions, and experimental protocols were approved by the UCSD Animal Care Program, following NIH guidelines. Radiation chimeras were generated as described[34]. In general, irradiated FVB mice were reconstituted with bone marrow from different strains that have been backcrossed to the FVB background for at least 2 generations. However, in the case of B-Ltβ$^{-/-}$ and T-Ltβ$^{-/-}$ mice, bone marrow donors were of the BL6 background, whose bone marrow did not lead to a graft vs. host response in irradiated FVB mice. Myc-CaP cells derived from the FVB background were provided by C. Sawyers (UCLA and Memorial Sloan Kettering Cancer Center)[35] and were cultured under standard conditions and confirmed to be mycoplasma free. Myc-CaP cells were injected subcutaneously into the flank of male FVB mice as described[35]. Tumor growth was measured with a caliper. Surgical procedures were as described[35].

Human Specimens

Anonymous human prostate, benign prostatic hyperplasia and prostate cancer frozen sections were provided by the Cooperative Human Tissue Network (CHTN). Pathology reports were provided by CHTN for each sample.

CXCL13 and B Cell Depletion and LT Inhibition

CXCL13 neutralizing antibody was purchased from R&D and administered i.p. at 200 mg/mouse as described[36]. Anti-CD20 was kindly provided by Genentech (Oceanside, Calif.) and was administered i.p. at 250 µg/mouse. LTβR-Ig fusion protein was a kind gift from Yang-Xin Fu (University of Chicago, Chicago, Ill.) and was administered as described[22]. hIgG and mouse IgG2a were purchased from Sigma-Aldrich and were used as controls.

IKKβ Inhibitors

ML120 was provided by Millenium Inc. and administered orally as described[37]. IKKβ Inhibitor IV was purchased from Calbiochem and was tail vein injected as described[14].

Histological Procedures

Mouse prostate and CaP tissues and dissected metastatic tumors were immersed in 10% neutral buffered formalin before sectioning and paraffin embedding. Sections were stained and processed as described[11], using H&E stain, TUNEL assay kit or antibodies for IKKα. (Imgenex), phospho-STAT3 (Cell Signaling) and CD19 (eBioscience) as described[38]. Frozen sections of human and mouse origins were fixed in acetone and processed as described[11], using antibodies for AR (Santa Cruz), B220 (BD), CD20 (BD), CD4 (BD) and CD8 (BD).

Analysis of RNA and Protein Expression

Total tissue RNA was prepared using RNAeasy (Qiagen). Quantitative PCR was performed as described[38]. Cells and tumors were lysed and analyzed by SDS-polyacrylamide gel electrophoresis and immunoblotting[38] with antibodies to histone H3, α-tubulin, STAT3 (Santa Cruz Biotechnology), ERK, phospho-ERK, AKT, phospho-AKT, phospho-STAT3 (Cell Signaling). Nuclear extracts were prepared and analyzed for NF-κB DNA-binding as described[39].

Lentiviral and Retroviral Transduction siRNAs to mouse IKKα, IKKβ and LTβR mRNAs were cloned into pLSLPw, provided by I. Verma (The Salk Institute), and lentivirus stocks were prepared as described[11]. Virus-containing supernatants were added to myc-CaP cells for 2 days with polybrene, and transduced cells were selected in 5 μg ml$^{-1}$ puromycin (Invitrogen).

Leukocytes Purification and Flow Cytometry

Peripheral blood mononuclear cells (PBMCs) were isolated by centrifugation on a double-layered Histopaque-Ficoll (GE Lifescience) gradient. Splenic B and T lymphocytes were isolated by magnetic cell sorting (MACS) with CD4, CD8 or CD19 antibodies conjugated to magnetic beads. Tumor infiltrating leukocytes were stained with CD45, B220, LTβR-Ig, TCRβ, Gr1, CD4 and CD8 fluorescent antibodies, as well as Aqua LIVE/DEAD dye (Molecular Probes) and analyzed on a flow cytometer (Accuri C6 or Becton Dickinson LSR II).

Statistical Analyses

Results are expressed as means±s.e.m. or s.d. Data were analyzed by Student's t-test and Kaplan-Meier survival analysis using GraphPad Prism statistical program. Error bars depict s.e.m. or s.d. P values >0.05 were considered insignificant (ns), 0.01 to 0.05 were considered significant (*), 0.001 to 0.01 were considered very significant () and <0.001 were considered as highly significant (*).

REFERENCES IN EXAMPLE 1

[1] Greenberg, N. M. et al. Prostate cancer in a transgenic mouse. *Proceedings of the National Academy of Sciences of the United States of America* 92, 3439-3443, (1995).

[2] Wu, X. et al. Generation of a prostate epithelial cell-specific Cre transgenic mouse model for tissue-specific gene ablation. *Mechanisms of development* 101, 61-69, (2001).

[3] Kuhn, R. Schwenk, F. Aguet, M. & Rajewsky, K. Inducible gene targeting in mice. *Science* 269, 1427-1429, (1995).

[4] Tumanov, A. V. et al. Dissecting the role of lymphotoxin in lymphoid organs by conditional targeting. *Immunol Rev* 195, 106-116, (2003).

[5] Kim, S. et al. Carcinoma-produced factors activate myeloid cells through TLR2 to stimulate metastasis. *Nature* 457, 102-106, (2009).

[6] Watson, P. A. et al. Context-dependent hormone-refractory progression revealed through characterization of a novel murine prostate cancer cell line. *Cancer research* 65, 11565-11571, (2005).

[7] Zheng, B. et al. CXCL13 neutralization reduces the severity of collagen-induced arthritis. *Arthritis and rheumatism* 52, 620-626, (2005).

[8] Lee, Y. et al. Recruitment and activation of naive T cells in the islets by lymphotoxin beta receptor-dependent tertiary lymphoid structure. *Immunity* 25, 499-509, (2006).

[9] Izmailova, E. S. et al. Use of molecular imaging to quantify response to IKK-2 inhibitor treatment in murine arthritis. *Arthritis and rheumatism* 56, 117-128, (2007).

[10] Park, B. K. et al. NF-kappaB in breast cancer cells promotes osteolytic bone metastasis by inducing osteoclastogenesis via GM-CSF. *Nature medicine* 13, 62-69, (2007).

[11] Luo, J. L. et al. Nuclear cytokine activated IKKα controls prostate cancer metastasis by repressing maspin. *Nature* 446, 690-694, (2007).

[12] Luo, J. L., Maeda, S., Hsu, L. C., Yagita, H. & Karin, M Inhibition of NF-κB in cancer cells converts inflammation-induced tumor growth mediated by TNFα to TRAIL-mediated tumor regression. *Cancer cell* 6, 297-305, (2004).

[13] Senftleben, U. et al. Activation by IKKα of a second, evolutionary conserved, NF-κB signaling pathway. *Science* 293, 1495-1499, (2001).

14. Park, B. K. et al. NF-kappaB in breast cancer cells promotes osteolytic bone metastasis by inducing osteoclastogenesis via GM-CSF. *Nature Med* 13, 62-69 (2007).

21. Tumanov, A. V. et al. Dissecting the role of lymphotoxin in lymphoid organs by conditional targeting. *Immunol Rev* 195, 106-116 (2003).

22. Lee, Y. et al. Recruitment and activation of naive T cells in the islets by lymphotoxin beta receptor-dependent tertiary lymphoid structure. *Immunity* 25, 499-509 (2006).

31. Greenberg, N. M. et al. Prostate cancer in a transgenic mouse. *Proc Natl Acad Sci USA* 92, 3439-3443 (1995).

32. Wu, X. et al. Generation of a prostate epithelial cell-specific Cre transgenic mouse model for tissue-specific gene ablation. *Mech Dev* 101, 61-69 (2001).

33. Kuhn, R., Schwenk, F., Aguet, M. & Rajewsky, K. Inducible gene targeting in mice. *Science* 269, 1427-1429 (1995).

34. Kim, S. et al. Carcinoma-produced factors activate myeloid cells through TLR2 to stimulate metastasis. *Nature* 457, 102-106 (2009).

35. Watson, P. A. et al. Context-dependent hormone-refractory progression revealed through characterization of a novel murine prostate cancer cell line. *Cancer Res* 65, 11565-11571 (2005).

36. Zheng, B. et al. CXCL13 neutralization reduces the severity of collagen-induced arthritis. *Arthritis Rheum* 52, 620-626 (2005).

37. Izmailova, E. S. et al. Use of molecular imaging to quantify response to IKK-2 inhibitor treatment in murine arthritis. *Arthritis Rheum* 56, 117-128 (2007).

38. Luo, J. L., Maeda, S., Hsu, L. C., Yagita, H. & Karin, M. Inhibition of NF-κB in cancer cells converts inflammation-induced tumor growth mediated by TNFα to TRAIL-mediated tumor regression. *Cancer Cell* 6, 297-305 (2004).

39. Senftleben, U. et al. Activation by IKKα of a second, evolutionary conserved, NF-κB signaling pathway. *Science* 293, 1495-1499 (2001).

Example 2

Figure 5:
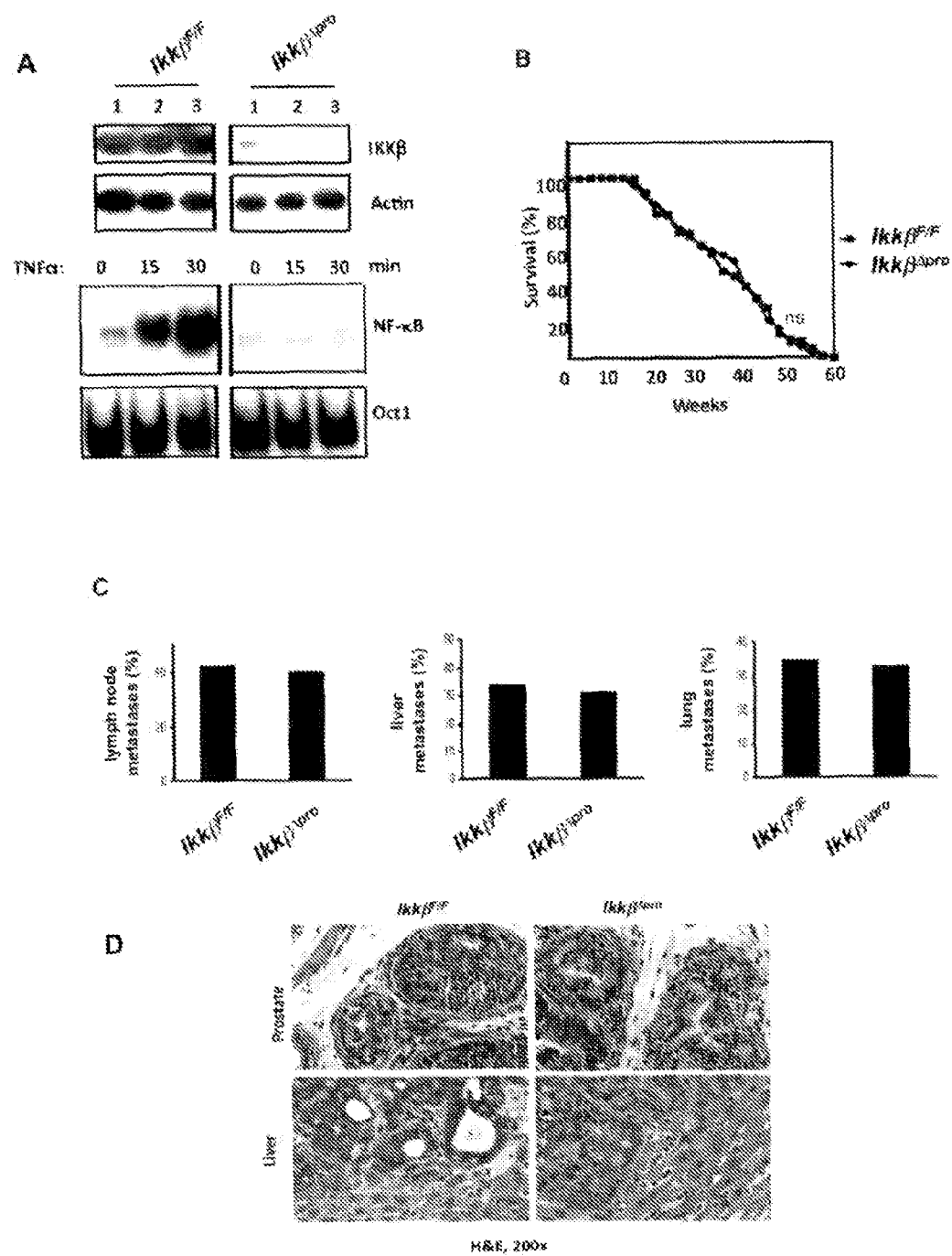
FIG. 5. IKKβ in prostate epithelial cells has no effect on CaP progression and metastasis. A. The deletion efficiency of IKKβ in Ikkγ$^{F/F}$/TRAMP and Ikkβ$^{F/F}$/TRAMP/PB-Cre4 (Ikkβ$^{\Delta pro}$) mice was analyzed. Primary prostate epithelial cells were isolated, cultured and stimulated with TNF-α (10 ng/ml). After 0, 15 and 30 min, cytoplasmic and nuclear extracts were prepared and analyzed for IKKβ expression (1,2,3 refer to different mice) or NF-κB and Oct-1 DNA binding activities. B. Survival of ikkβ$^{F/F}$/TRAMP (n=21) and Ikkβ$^{\Delta pro}$/TRAMP (n=16) mice were compared by Kaplan-Meier analysis. P values were determined and are depicted as insignificant (ns), significant (*), very significant () or highly significant (*). C. Incidence of lymph node, liver and lung metastases in Ikkβ$^{F/F}$/TRAMP and Ikkβ$^{\Delta m}$/TRAMP mice at time of death. D. Histological analysis of primary CaP and liver metastasis in Ikkβ$^{F/F}$/TRAMP and Ikkβ$^{\Delta pro}$/TRAMP mice.
Figure 6:
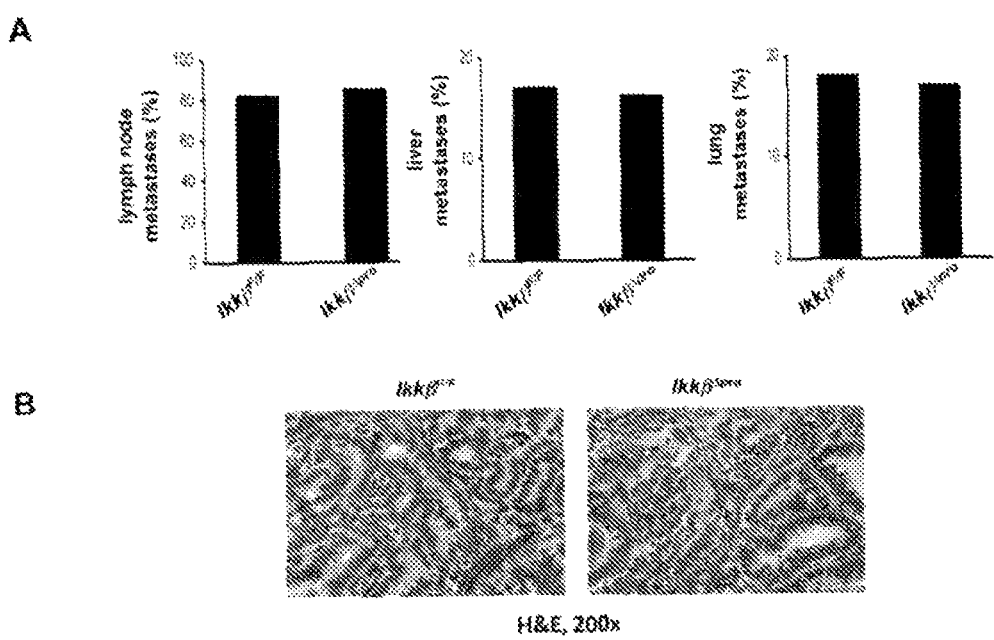
FIG. 6. IKKβ in prostate epithelial cells has no effect on emergence of CR-CaP. A. Twenty-week old Ikkβ$^{\Delta pro}$/TRAMP (n=12) and Ikkβ$^{F/F}$/TRAMP (n=13) males were castrated. After 5 months, mice were sacrificed and incidence of lymph node, lung and liver metastases was determined. B. Histological analysis of primary prostate tumors from castrated Ikkβ$^{\Delta pro}$/TRAMP and Ikkβ$^{F/F}$/TRAMP mice.
Figure 7:
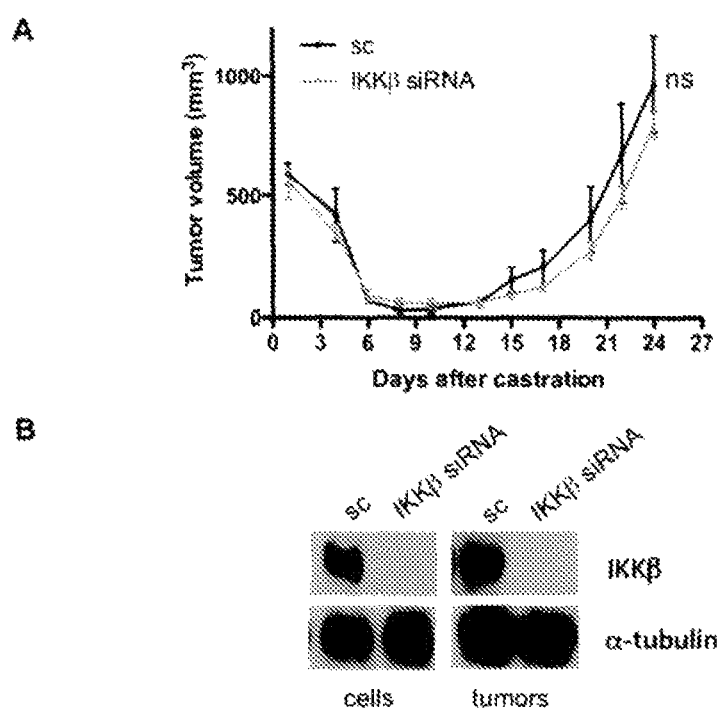
FIG. 7. Silencing of IKKβ in CaP cells has no effect on emergence of CR-CaP. Male FVB mice were injected with myc-CaP cells, previously infected with lentiviruses expressing control (scrambled, sc) or IKKβ specific siRNAs. When tumors reached 900 mm$^3$, mice (n=10 per group) were castrated. A. Tumor size was measured every 2-3 days. Results are averages±s.e.m. P value was determined and depicted as above. B. Myc-CaP cells were used for inoculation and the resulting tumors, collected at the end of the experiment, were analyzed for IKKβ expression.

To determine whether IKKβ-driven NF-κB participates in development of CR-CaP, we conditionally deleted the Ikkβ gene in prostate epithelial cells of TRAMP mice, in which CaP is induced by prostate specific expression of SV40 T antigen[12]. Counter to previous expectations[4], IKKβ ablation in prostate epithelial cells had no effect on genesis and progression of AD-CaP (FIG. 5) or development of CR-CaP after castration (FIG. 6). To facilitate mechanistic analysis of CR-CaP development we used subcutaneous (SC) allografts of the mouse AD-CaP cell line myc-CaP, which is derived from the FVB genetic background[13]. Silencing of IKKβ in myc-CaP cells did not affect primary tumor growth or CR-CaP re-growth in castrated FVB mice (FIG. 7).

Figure 8:
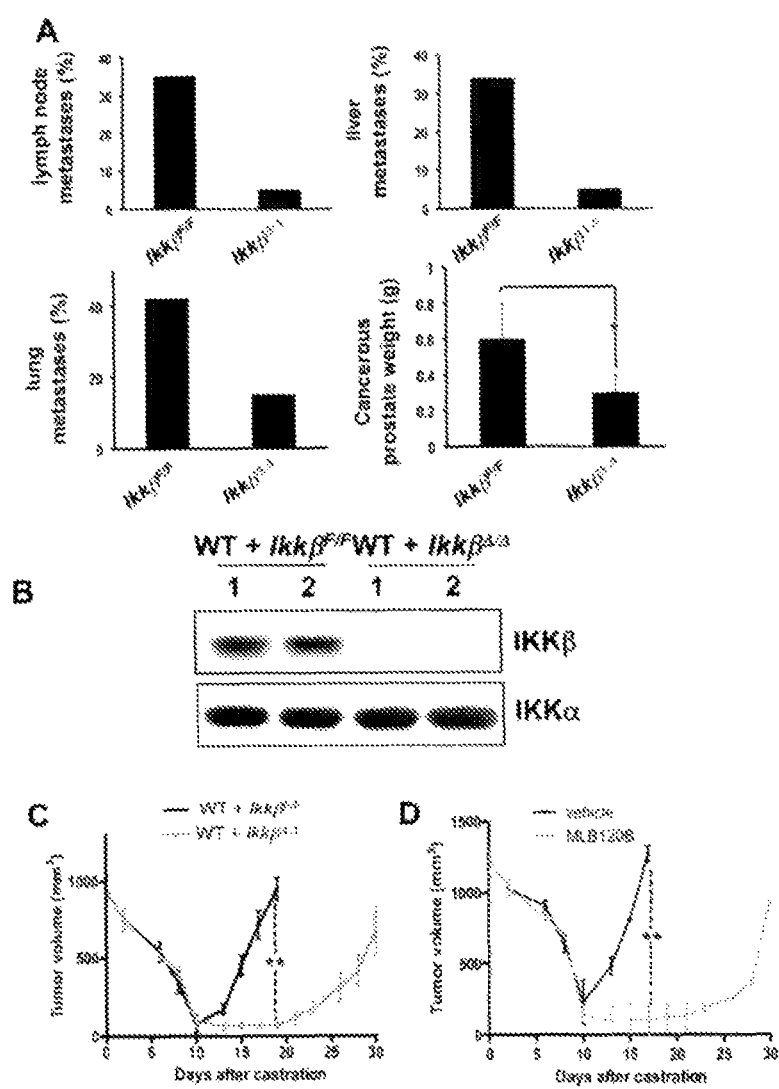
FIG. 8. IKKβ deletion in BMDC retards CR-CaP appearance and metastasis. A. Twenty week old Ikkβ$^{F/F}$/TRAMP/Mx1-Cre (Ikkβ$^{Δ/Δ}$TRAMP) and Ikkβ$^{F/F}$/TRAMP males (n=15-17) were injected three times with poly(IC) and castrated 3 days after last injection. Five months later, mice were sacrificed and prostate tumor weight and incidence of lymph node, lung and liver metastases were determined. B. Six week old FVB males were lethally irradiated and transplanted with BM of male Ikkβ$^{F/F}$ or Ikkβ$^{F/F}$/Mx-1Cre mice (n=10 each group). After 8 weeks, mice received 2×10$^6$ myc-CaP cells subcutaneously. When tumors reached 900 mm$^3$, mice were thrice injected with poly(IC) to delete IKKβ in BMDC and castrated 3 days later. IKKβ deletion was examined by immunoblot analysis of peripheral leukocytes. C. Tumor volume in above mice was measured every 2-3 days. Results are averages±s.e.m. (n=10). D. Six week old FVB mice (n=6 each group) were inoculated with myc-CaP cells and when tumors reached 1000 mm$^3$, were castrated and injected twice daily with vehicle or IKKβ inhibitor, ML120B. Tumor volume was measured as above. Results are averages±s.e.m. P values were determined and depicted as above.

By contrast, deletion of IKKβ in interferon-responsive cells upon induction of Mx1-Cre expression prevented castration-induced metastatic spread in TRAMP/Ikkβ$^{F/F}$/Mx1-Cre mice (FIG. 8A). To narrow down the role of IKKβ to bone marrow (BM)-derived cells (BMDCs), we reconstituted irradiated FVB mice with BM from Ikkβ$^{F/F}$ and Ikkβ$^{Δ/Δ}$ mice (Ikkβ$^{F/F}$/Mx1-Cre mice injected with poly(IC) to induce Mx1-Cre) and inoculated the resulting chimeras (FIG. 8B) with myc-CaP cells. Absence of IKKβ in BMDC had no impact on primary tumor growth, but delayed CR-CaP emergence after castration (FIG. 8C). A similar delay in CR-CaP growth was seen in castrated tumor-bearing mice treated with specific IKKβ inhibitors[14, 15] (FIG. 8D and data not shown).

Example 3

Figure 9:
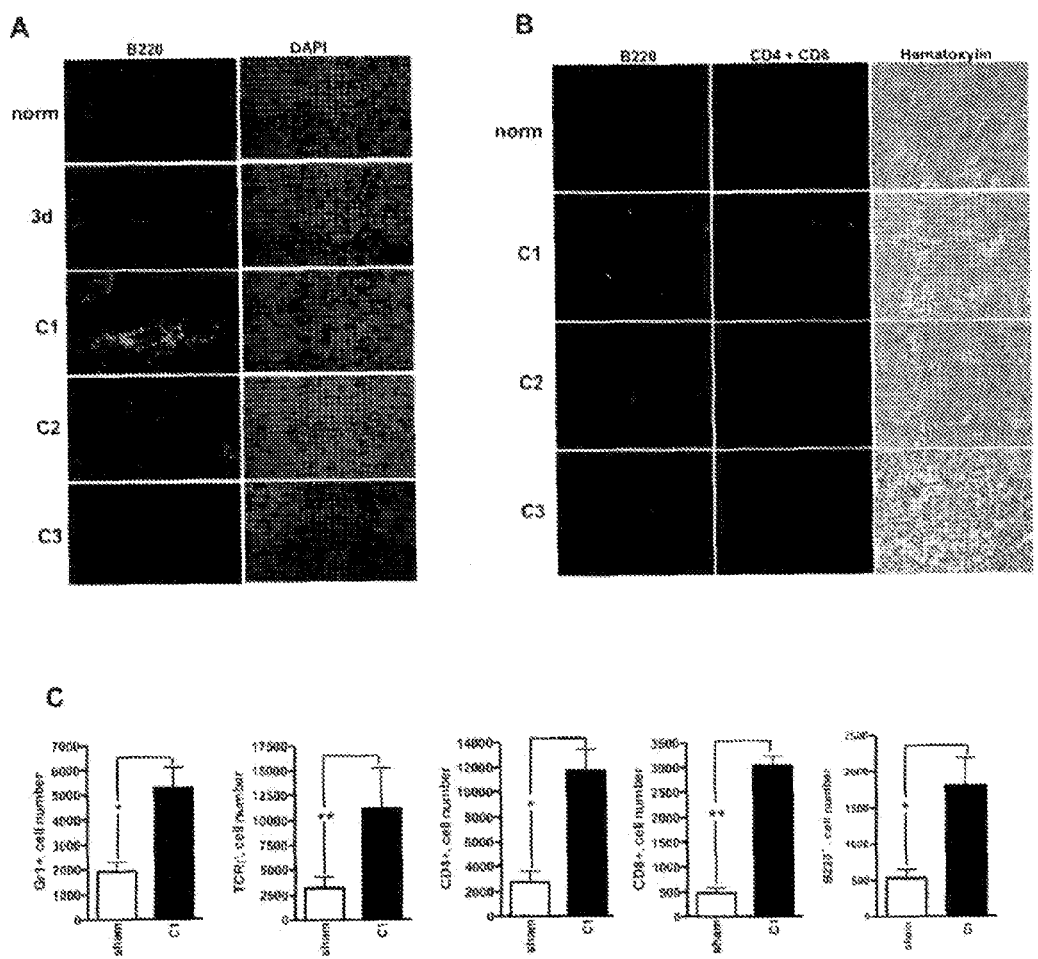
FIG. 9. Distribution of B cells in tumors. Myc-CaP tumors were established in 6 weeks old FVB mice. When tumors reached 1000 mm$^3$, mice were left untreated (normal) or castrated. A,B. tumors were collected either 3 days or 1, 2 or 3 weeks later. Frozen sections were stained with anti-B220 antibody or a combination of anti-CD4 and anti-CD8 antibodies, counterstained with DAPI or hematoxylin and analyzed by immunofluorescent microscopy. C. Myc-CaP tumors were established as above. When tumors reached 1000 mm$^3$, mice were sham operated or castrated. Tumor samples were collected, digested with collagenase, stained with the indicated cell marker antibodies and analyzed by flow cytometry.
Figure 10:
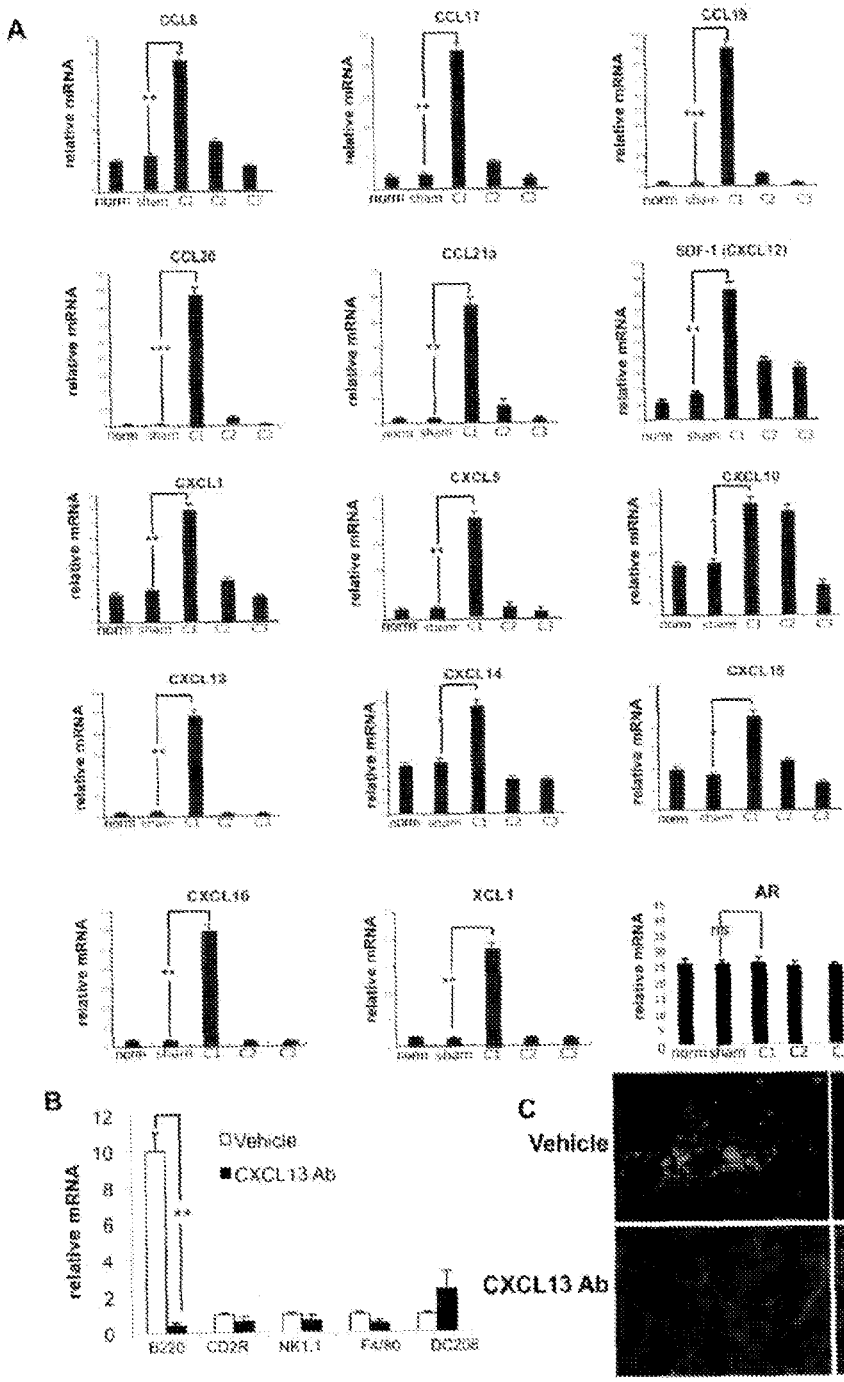
FIG. 10. Castration-induced regression of CaP results in induction of inflammatory chemokines in tumor remnants. A. Myc-CaP tumors were established in 6 week old FVB mice (n=10). When tumors reached 1000 mm$^3$, mice were left untreated (normal), sham operated or castrated and tumors were collected 1, 2 or 3 weeks later. Total RNA was isolated and expression of the indicated chemokine and AR mRNAs was quantitated by Q-PCR and normalized to the amount of cyclophilin A mRNA. Results are averages±s.d. (n=3). P values for the difference in mRNA amounts between sham operated and castrated mice at week 1 were determined and depicted as above. B. Myc-CaP tumors were established as described above. Three days before castration mice were injected i.p. with 200 μg of CXCL13 neutralizing antibody or vehicle (PBS). Tumor samples were collected one week after castration. Total RNA was isolated and expression of the indicated cellular marker mRNAs was quantitated by Q-PCR and normalized to the amount of cyclophilin A mRNA. Results are averages±s.d. P values were determined and depicted as above. C. Frozen sections of SC tumors were stained with anti-B220, counterstained with DAPI and analyzed by immunofluorescent microscopy.
Figure 11:
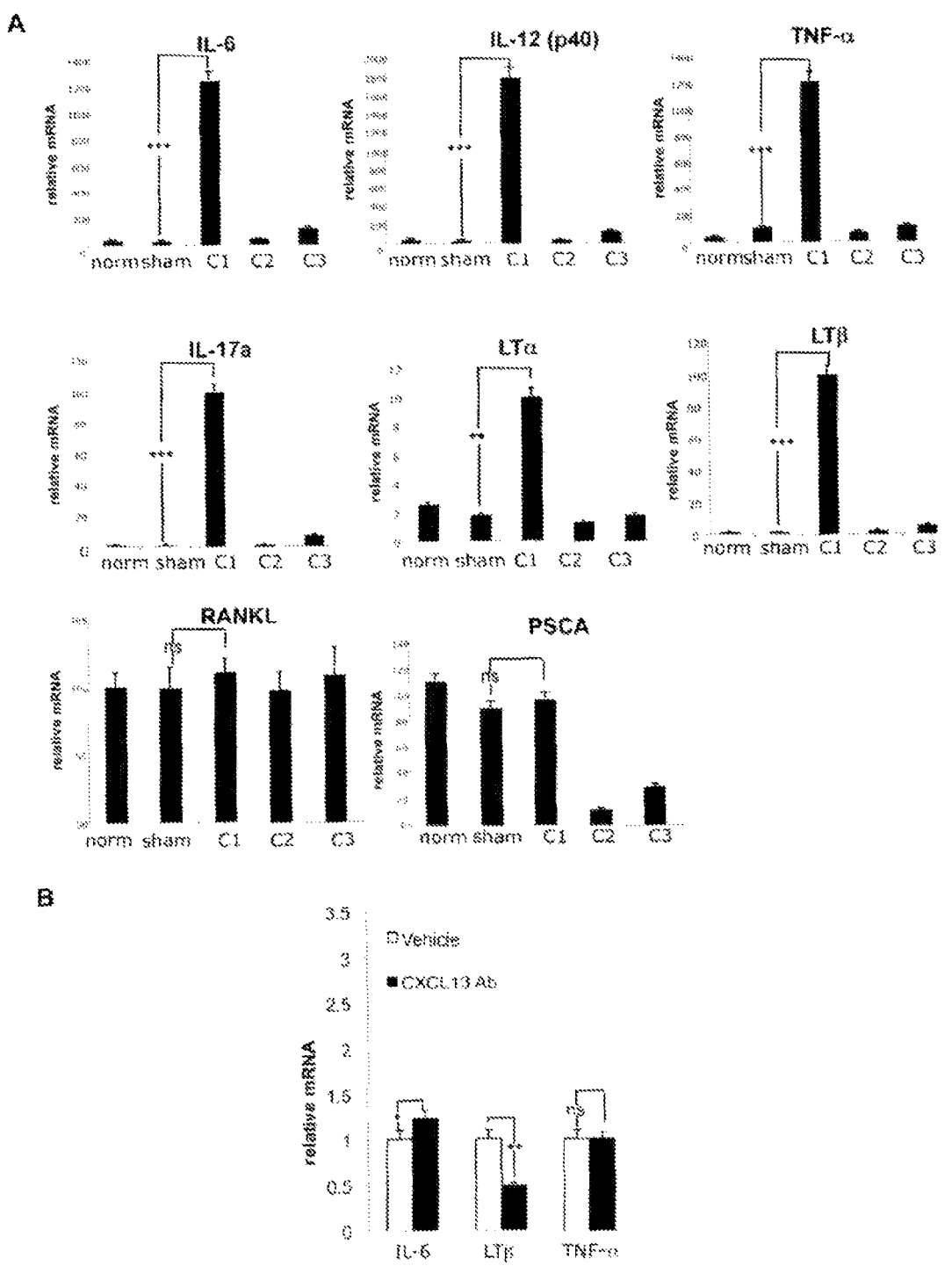
FIG. 11. Castration-induced regression of CaP results in induction of inflammatory cytokines in tumor remnants. A. Total RNA was isolated from tumor samples starting 1 week after castration of the mice described above (FIG. 10) and analyzed for expression of the indicated cytokines or prostate stem cell antigen (PSCA) mRNAs as above. B. Total RNA was isolated from the samples described in FIG. 9B and analyzed for expression of the indicated cytokine mRNAs (n=3). P values were determined and depicted as above.
Figure 12:
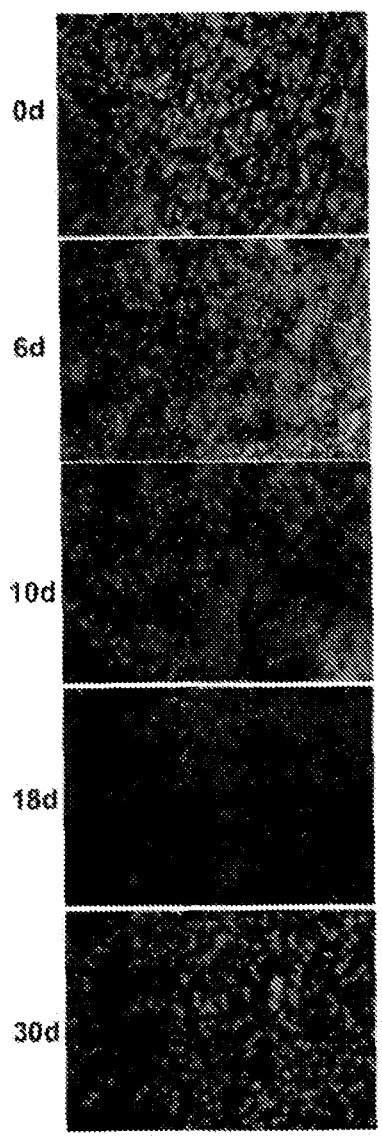
FIG. 12. AR localization during the emergence of CR-CaP. Myc-Cap tumors were established in FVB male mice. Tumor samples were collected at the indicated time points after castration and analyzed for AR localization by immunofluorescent microscopy. Nuclear AR is seen in tumors from non-castrated mice (0 d) and 30 days after castration.

Dependence of CR-CaP emergence on IKKβ in BMDC, suggested that androgen deprivation elicits a tumor-associated inflammatory response. Castration of mice bearing myc-CaP tumors resulted in CaP cell death, peaking within one week (FIG. 1A). Concurrently, the regressing tumors were infiltrated with T and B lymphocytes, NK cells and myeloid cell types (FIG. 1B; FIG. 9). Infiltration was transient, declining by 2 weeks after castration. B and T lymphocyte infiltration was also detected in 100% of human CaP samples (untreated patients with Gleason scores of 6-8), but B cells were undetectable in normal prostate or benign prostatic hyperplasia (FIG. 1C). The mRNAs for many inflammatory chemokines were also upregulated in the myc-CaP allografts, but no changes in AR mRNA expression were found (FIG. 10A). These chemokines may recruit lymphoid and myeloid cells into the regressing tumor. Indeed, antibody mediated inhibition of CXCL13, a B cell chemoattractant[16], prevented castration-induced B cell recruitment (FIG. 10B,C). Inflammatory cytokine mRNAs, including IL-6, IL-12, TNF-α and lymphotoxin (LT), were also upregulated in the regressing myc-CaP allograft, but only LT expression was reduced upon CXCL13 inhibition (FIG. 11). Castration resulted in nuclear export of AR, but after 3 weeks AR was nuclear again (FIG. 12), suggesting it is activated at late phases of CR-CaP growth despite androgen depletion.

Example 4

Figure 13:
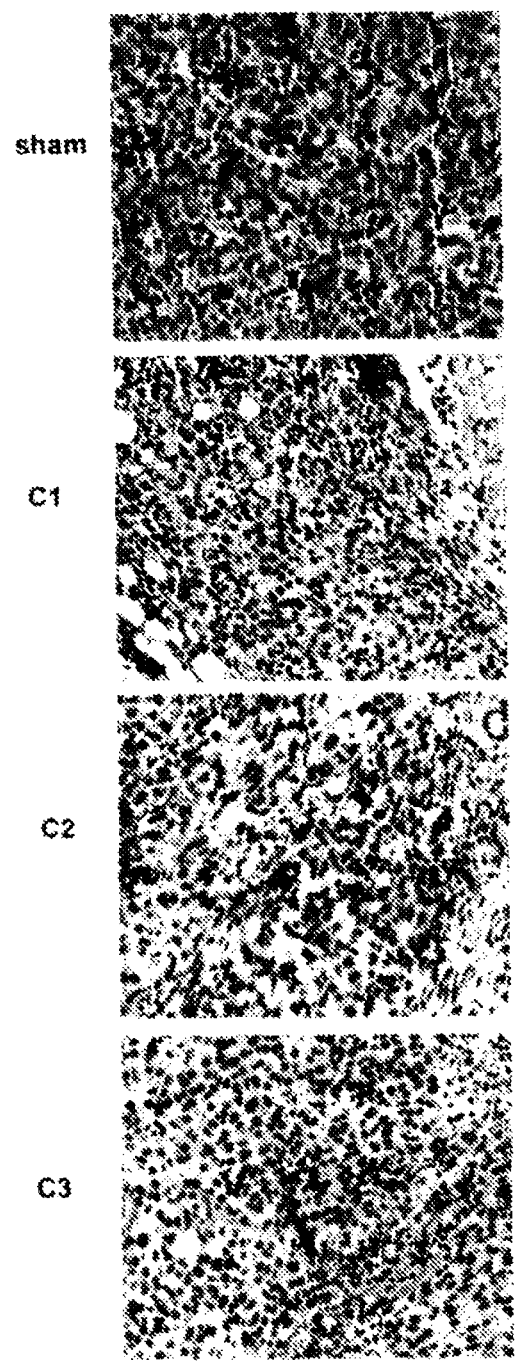
FIG. 13. STAT3 is phosphorylated after castration. Myc-CaP tumors were established as described above. Tumor samples were collected at the indicated time points after castration or sham operation. Paraffin-embedded sections were analyzed for STAT3 phosphorylation by staining with phospho-STAT3 antibody.
Figure 14:
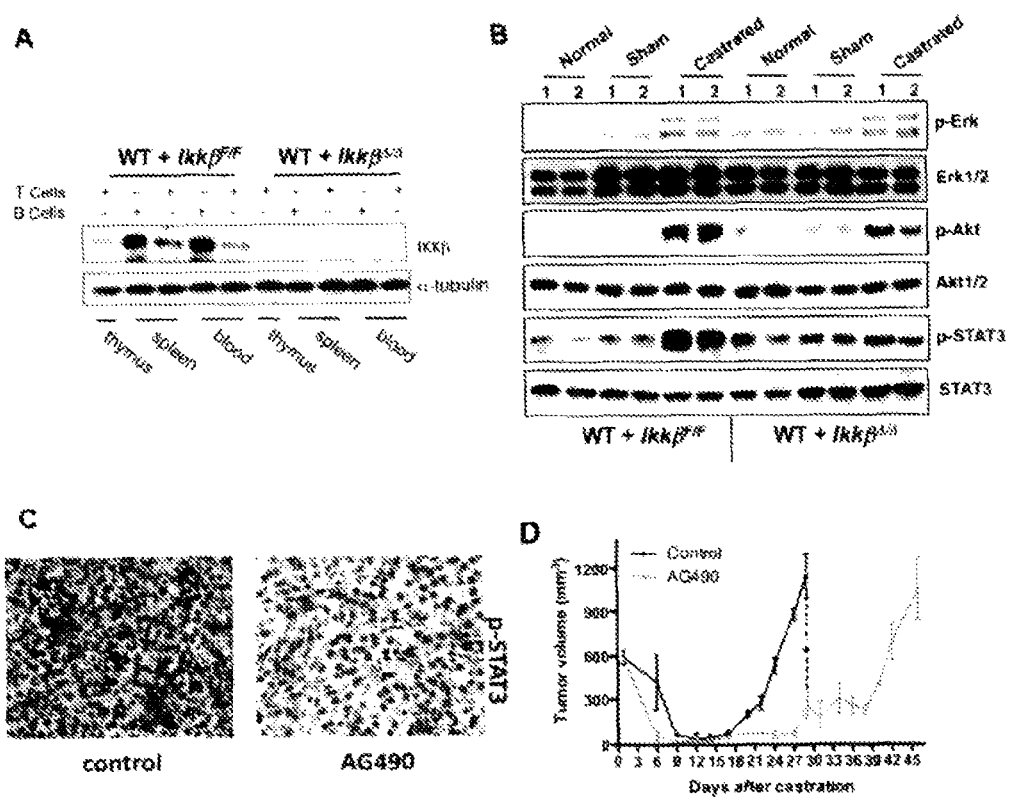
FIG. 14. STAT3 activation and its role in CR-CaP emergence. A,B WT+Ikkβ$^{F/F}$ and WT+Ikkβ$^{Δ/Δ}$ radiation chimeras (n=10 each group) bearing myc-CaP allografts were established as above and injected with poly(IC) to delete IKKβ☐ in BMDC before castration or sham operation. After one month, mice were sacrificed for analysis. A. Lymphocytes were isolated from indicated tissues and analyzed for IKKβ expression. B. Tumor samples were immunoblotted to determine expression and phosphorylation of indicated signaling proteins. C,D FVB mice bearing myc-CaP tumors were castrated. Starting one day before castration, the mice (n=10 per group) were injected twice daily with vehicle or AG490, an inhibitor of STAT3 phosphorylation. C. One week after castration, tumors were collected, paraffin-embedded, sectioned and stained with phospho-STAT3 antibody. D. Tumor volume was measured every 2-3 days as above. Results are averages±s.e.m. P values were determined and are indicated as above.
Figure 15:
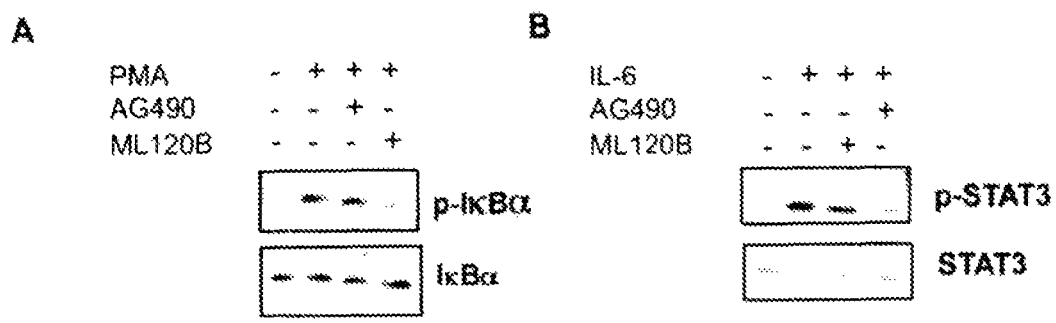
FIG. 15. Selectivity of IKKβ and STAT3 phosphorylation inhibitors. A. Myc-CaP cells were cultured to 60% confluency and pre-treated for 1 hr with AG490 (100 μM) or ML120B (20 μM), followed by stimulation with PMA (10 ng/ml) for 10 min. Cells were collected and IκBα phosphorylation was analyzed. B. Myc-CaP cells were pre-treated with AG490 or ML120B and after 1 hr, were stimulated with IL-6 (20 ng/ml) for 30 min. Cells were collected and STAT3 phosphorylation was analyzed by immunoblotting.

STAT3 was proposed to promote activation of unliganded AR[17]. Indeed, STAT3 was activated during CR-CaP emergence, faster than AR was (FIG. 13). Mx1-Cre-mediated IKKβ deletion, which was nearly complete in mature B and T lymphocytes (FIG. 14A), prevented STAT3 activation in regressing tumors, but did not affect ERK and AKT activation (FIG. 14B). Immunohistochemical analysis confirmed STAT3 activation in CaP cells, inhibitable by A490 (FIG. 14C), an inhibitor of STAT3 phosphorylation[18] that delayed appearance of CR-CaP (FIG. 14D) but did not inhibit IKK activation (FIG. 15A). Conversely, ML120B did not inhibit STAT3 activation (FIG. 15B).

Example 5

Figure 2:
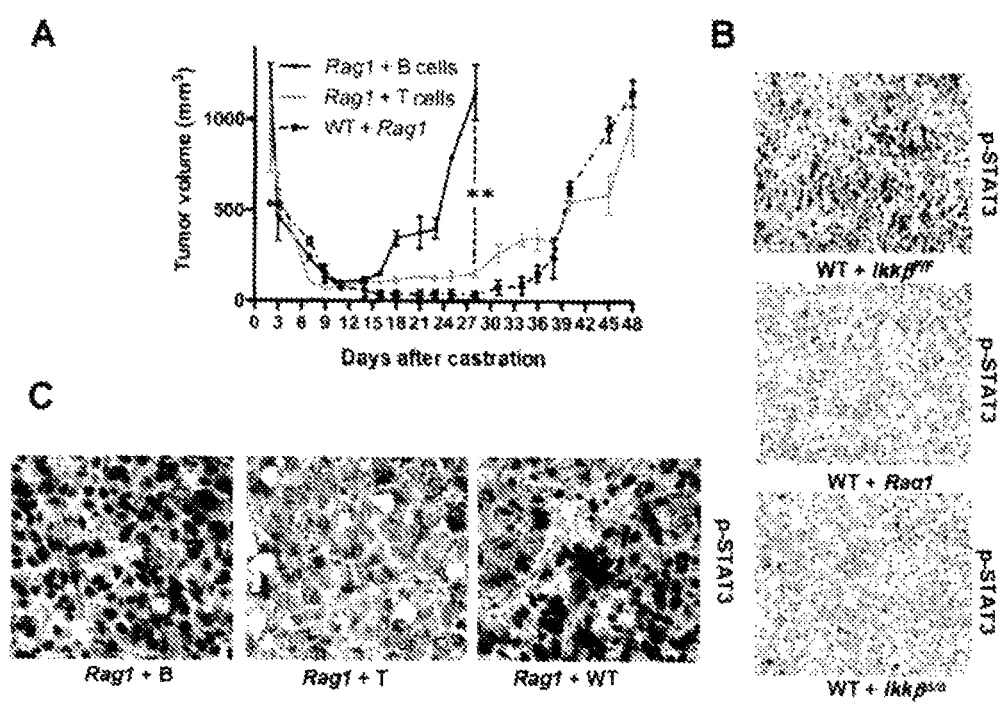
FIG. 2. Role of B cells and IKKβ in STAT3 activation and CR-CaP emergence. A. Myc-CaP tumors were established in WT mice reconstituted with BM from Rag1$^{-/-}$ males (n=10) or in Rag1$^{-/-}$ males. When tumors reached 1000 mm$^3$, mice were castrated. Three days before castration, Rag1$^{-/-}$ mice (n=10 per group) received via the tail vein purified splenic B or T cells. Tumor volume was measured. Results are averages±s.e.m. P values were determined and are indicated as above. B. Tumors were removed from radiation chimeras reconstituted with Ikkβ$^{F/F}$, Ikkβ$^{\Delta/\Delta}$, or Rag1$^{-/-}$ BM, one week after castration. STAT3 phosphorylation was analyzed by immunohistochemistry. C. Tumor-bearing Rag1$^{-/-}$ males were injected with WT splenocytes (Rag1+WT), or purified splenic B (Rag1+B) or T (Rag1+T) lymphocytes. One day later, mice were castrated and after one week, tumors were removed and analyzed for STAT3 phosphorylation.
Figure 17:
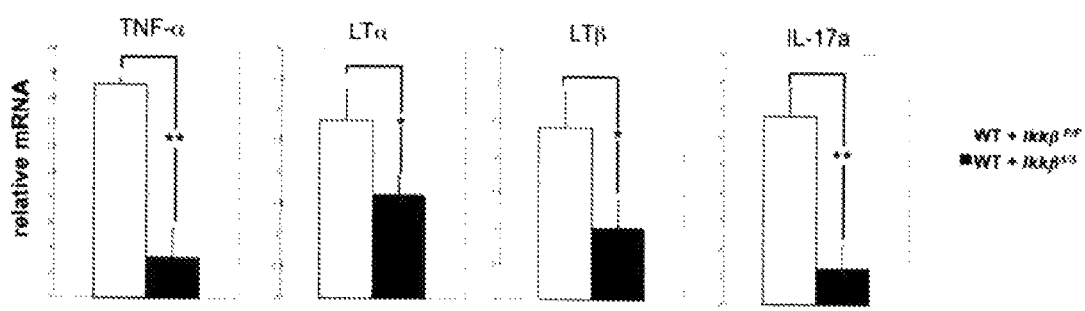
FIG. 17. Castration-induced regression of AD-CaP induces expression of cytokines in an IKKβ-dependent manner. Myc-CaP tumors were established in WT+Ikkβ$^{F/F}$ and WT+Ikkβ$^{Δ/Δ}$ radiation chimeras. When tumors reached 1000 mm$^3$, mice were castrated and one week later, tumor samples were collected. Expression of the indicated cytokine mRNAs was analyzed by Q-PCR and normalized to cyclophilin A mRNA. Results are averages±s.d. (n=5). P values were determined and depicted as above.
Figure 18:
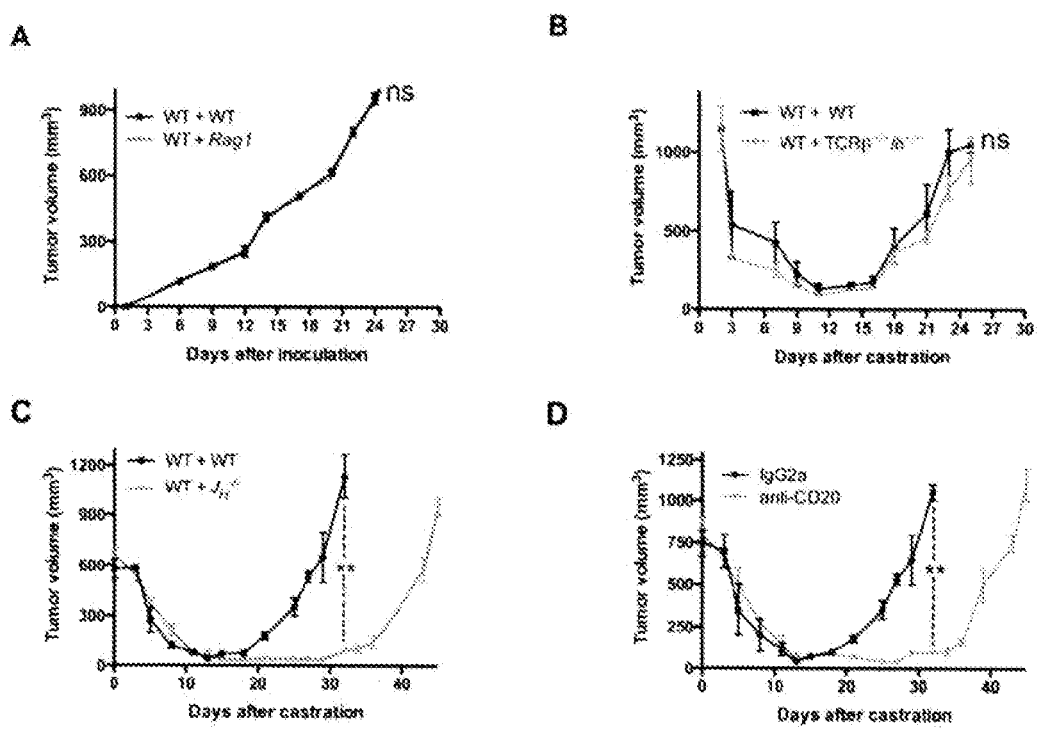
FIG. 18. Lymphocytes are not required for primary CaP growth but B cells rather than T cells accelerate appearance of CR-CaP. A. Lethally irradiated FVB male mice (n=10 per group) were reconstituted with WT or Rag1$^{-/-}$ BM. After 8 weeks, myc-CaP cells were implanted and their growth monitored. B. Lethally irradiated FVB male mice (n=10 per group) were reconstituted with BM of WT (WT+WT) or T cell deficient Tcrβ$^{-/-}$/δ$^{-/-}$ mice (WT+Tcrβ$^{-/-}$δ$^{-/-}$). After 8 weeks, myc-CaP tumors were established and the mice were castrated when tumors reached 1000 mm$^3$. Tumor volume was measured as above. C. Lethally irradiated FVB male mice (n=10 per group) were reconstituted with BM of WT (WT+WT) or B cell deficient J$_H$$^{-/-}$ (WT+J$_H$$^{-/-}$) mice. After 8 weeks, myc-CaP tumors were established and the mice were castrated when tumors reached 1000 mm$^3$. Tumor volume was monitored as above. P values were determined and depicted as above. D. FVB mice (n=5 each group) were inoculated with myc-CaP cells, castrated as above and were given by i.p. injection IgG2a or anti-CD20 (200 μg) every 5 days, starting 4 days before castration. Tumor volume was measured as above. Results are averages±s.e.m.

Ablation of BMDC IKKβ did not prevent leukocyte recruitment into regressing tumors (FIG. 16) but did inhibit cytokine induction (FIG. 17). To further investigate the role of lymphocytes, we used chimeric mice generated by transplantation of BM from lymphocyte-deficient Rag1$^{-/-}$ mice. Although primary tumor growth was identical in mice receiving WT or Rag1$^{-/-}$ BM (FIG. 18A), CR-CaP growth was significantly delayed in mice receiving Rag1$^{-/-}$ BM (FIG. 2A), but not in mice reconstituted with BM from Tcrβ$^{-/-}$/δ$^{-/-}$ mice (FIG. 18B), which lack only mature T lymphocytes. CR-CaP growth was delayed in mice reconstituted with BM from J$_H$$^{-/-}$ mice (FIG. 18C), which lack mature B cells, or upon B cell depletion with CD20 antibody[19] (FIG. 18D). Reconstitution of Rag1$^{-/-}$ FVB mice with splenic B cells, but not T cells of FVB mice, restored rapid CR-CaP re-growth (FIG. 2A). Primary tumors, isolated from Rag1$^{-/-}$ chimeric mice one week after castration, did not show STAT3 activation (FIG. 2B), but reconstitution with B cells, rather than T cells, restored castration-induced STAT3 phosphorylation (FIG. 2C).

Example 6

Figure 3:
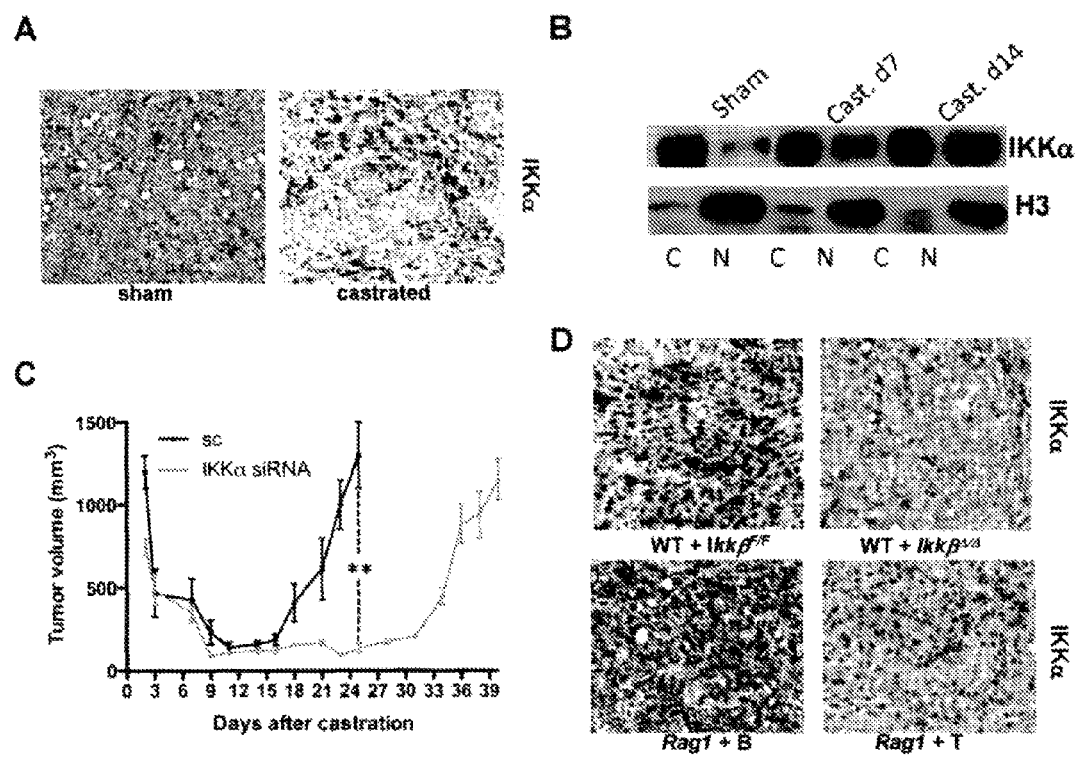
FIG. 3. Role of IKKα in emergence of CR-CaP. Tumor-bearing mice were castrated or sham operated as above. A. Tumors were analyzed one week later for nuclear IKKα by immunohistochemistry. B. Tumors removed at indicated times were divided into cytosolic (C) and nuclear (N) fractions and IKKα and histone H3 distribution was determined. C. Tumors were established using myc-CaP cells transduced with lentiviruses expressing scrambled siRNA (sc) or IKKα-specific siRNA. Mice were castrated as above and tumor volume was measured. Results are averages±s.e.m. (n=10). P values were determined and indicated as above. D. Tumors were established in lethally irradiated FVB males reconstituted with Ikkβ$^{F/F}$ or Ikkβ$^{\Delta/\Delta}$ BM or in Rag1$^{-/-}$ males reconstituted with either B or T cells. Ikkβ$^{F/F}$ and Ikkβ$^{\Delta/\Delta}$ chimeras were i.p. injected three times with poly(IC) (250 μg) prior to castration to delete IKKβ. One week after castration, tumor samples were analyzed for IKKα distribution by immunohistochemistry. Nuclear IKKα results in punctuate staining, while cytoplasmic IKKα results in diffuse staining.
Figure 19:
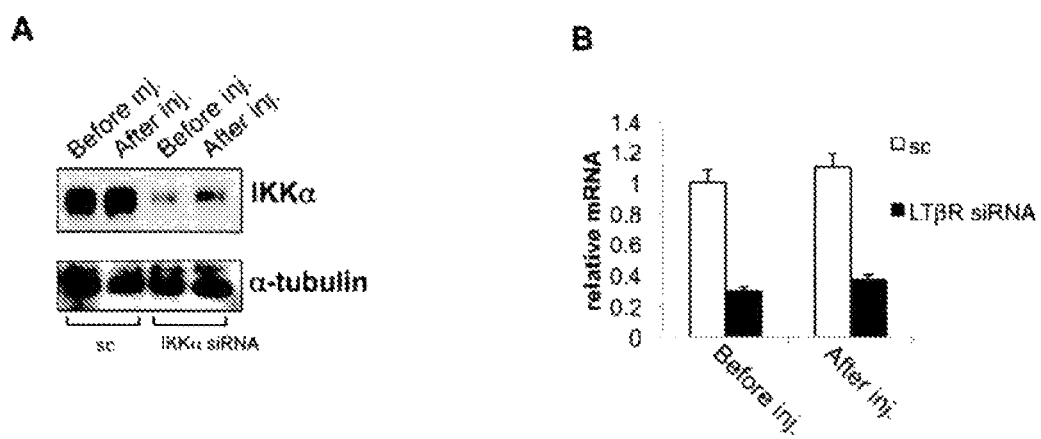
FIG. 19. siRNA-mediated IKKα and LTβR silencing. A. Myc-CaP cells infected with lentiviruses encoding scrambled (sc) or IKKα siRNA were analyzed before implantation or after generation of tumor allografts for IKKα expression. B. LTβR mRNA was analyzed by Q-PCR and normalized to cyclophilin A in myc-CaP cells infected with lentiviruses encoding scrambled (sc) or LTβR siRNA before implantation or after generation of tumor allografts.
Figure 20:
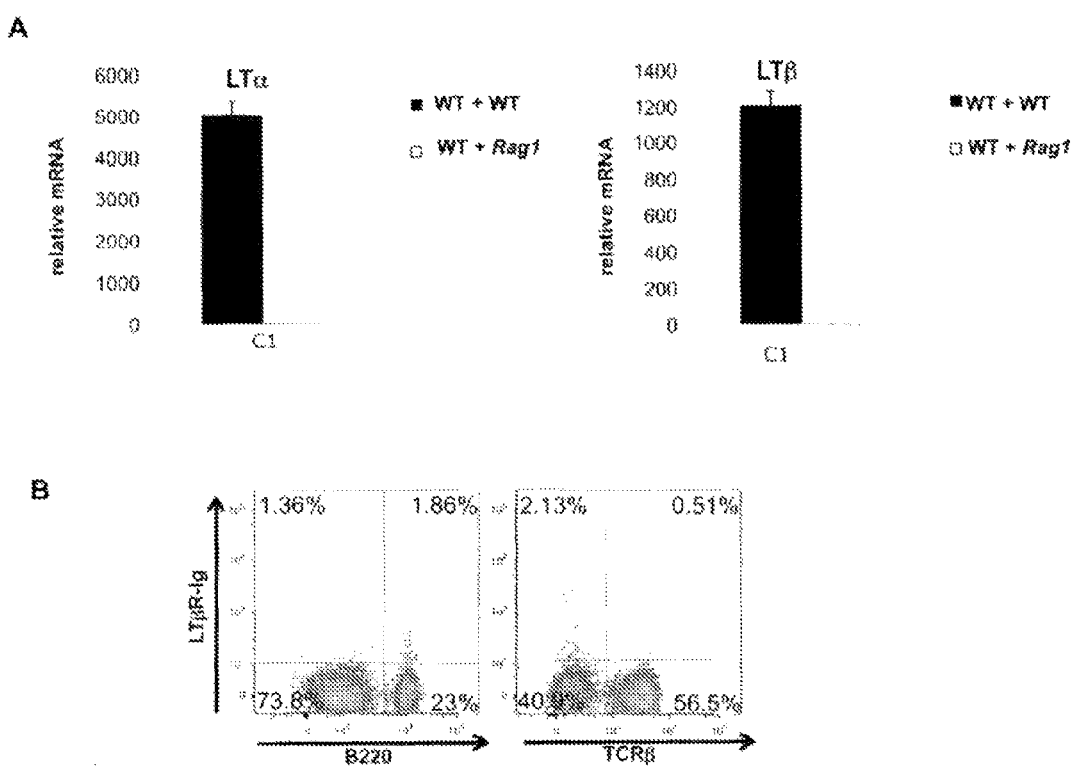
FIG. 20. LT production in tumors is significantly reduced in the absence of lymphocytes and is localized mainly to B cells. A. Lethally irradiated FVB males were reconstituted with BM from Rag1$^{-/-}$ as described above. Tumors were established, collected 1 week after castration and total RNA was isolated. Expression of LTα and LTβ mRNAs was quantitated by Q-PCR and normalized to that of cyclophilin A mRNA. Results are averages±s.d. (n=5). B. Myc-CaP tumors were established in FVB mice. One week after castration the tumors were removed, treated with collagenase and single cell suspension stained with LTβR-Ig fusion protein and either B220 or TCRβ antibodies and analyzed by flow cytometry.
Figure 21:
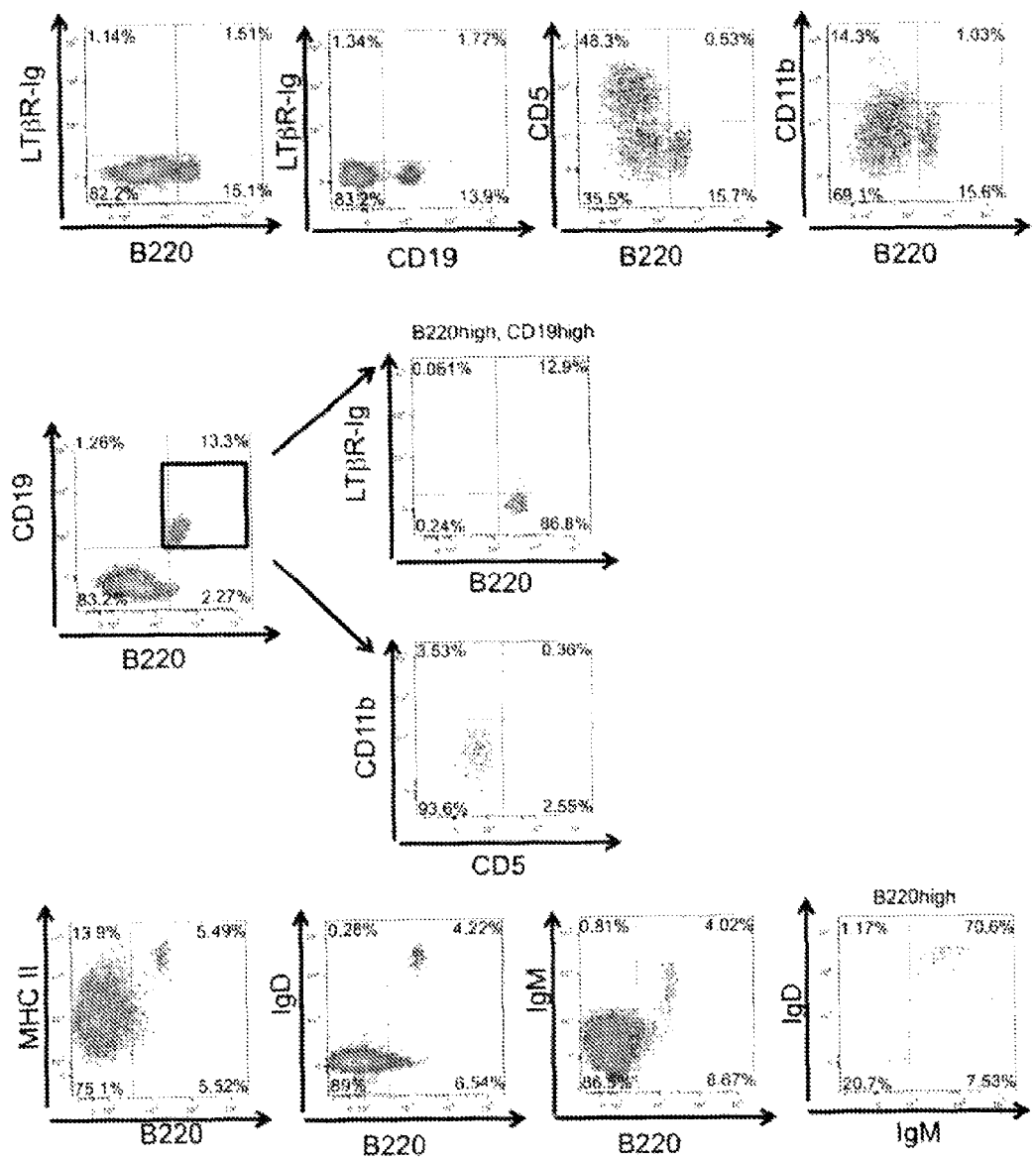
FIG. 21. Characterization of tumor infiltrating B cells. Subcutaneous myc-CaP tumors were isolated one week after castration and digested with collagenase to prepare a single cell suspension that was filtered through a cell strainer. The cells were then stained with fluorescently-labeled antibodies to CD45, B220, CD19, IgD, IgM, CD11b, MHC class II and CD5 as well as LTβR-Ig fusion protein followed by anti-human Ig-PE antibody (Jackson Immunoresearch) and Aqua LIVE/DEAD dye (Molecular Probes). The stained cells were analyzed by flow cytometry on a BD LSRII instrument. Live hematopoietic cells were gated as CD45$^+$ Aqua$^-$. Shown are representative dot plots from one typical tumor.

CaP allografts from castrated, but not sham-operated, mice exhibited IKKα nuclear translocation (FIG. 3A,B). Silencing of IKKα in myc-CaP cells using siRNA (FIG. 19A) had little effect on primary tumor growth, but delayed CR-CaP emergence (FIG. 3C). Nuclear translocation of IKKα was dependent on IKKβ in BMDC and on B cells, but not on T cells (FIG. 3D). IKKα nuclear translocation parallels progression of human and murine CaP and coincides with primary tumor infiltration with cells expressing IKKα-activating cytokines, RANK ligand (RANKL) and LTα[11]. Castration induced LTα and LTβ in regressing myc-CaP allografts, but did not alter RANKL expression (FIG. 11). LT expression in regressing tumors was absent in Rag1$^{-/-}$ mice (FIG. 20A) and flow cytometry localized it to tumor infiltrating B cells (TIBC; FIG. 20B). We characterized TIBC by 7-color flow cytometry with several markers and a LTβR-Ig fusion protein to detect LT. The typical TIBC was a conventional, mature B2 cell that expressed LT on its surface and was negative for B1 markers (FIG. 21). IKK13 deletion abolished LT expression by B cells (FIG. 4A), supporting the previously suggested[20] role of NF-κB in LTα/β induction.

Example 7

Figure 4:
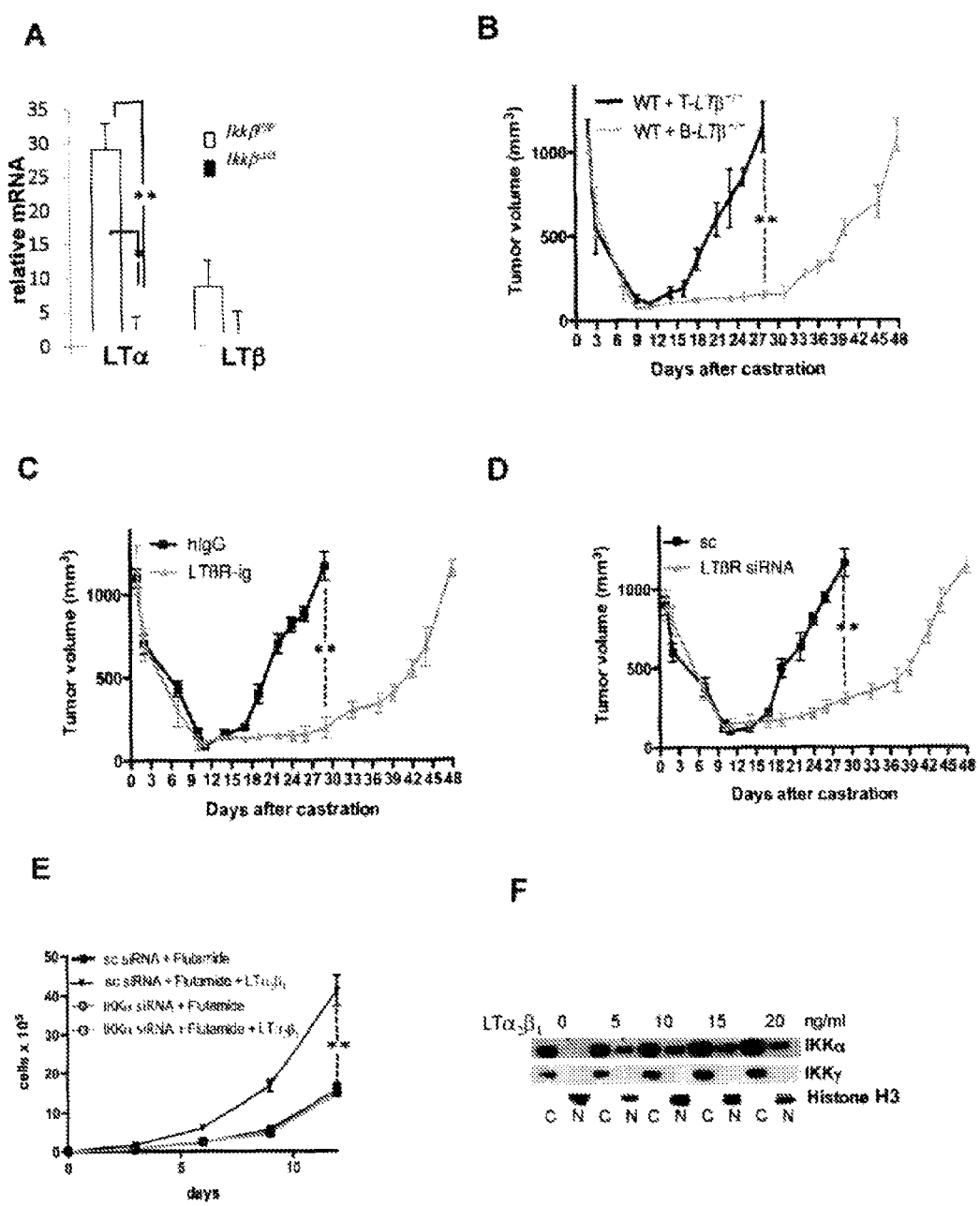
FIG. 4. IKKβ-dependent lymphotoxin production by tumor-infiltrating B cells stimulates IKKα-dependent androgen-free survival. A. RNA from splenic B cells of Ikkβ$^{F/F}$ and Ikkβ$^{\Delta/\Delta}$ mice was analyzed for LTα and LTβ expression as above. Results are averages±s.d. (n=3). B. Lethally irradiated FVB males were reconstituted with BM from B-Ltβ$^{-/-}$ or T-Ltβ$^{-/-}$ mice (n=6 per group). After 8 weeks, myc-CaP tumors were established, mice were castrated and tumor volume was measured as above. Results are averages±s.e.m. C. FVB mice (n=6 each group) bearing myc-CaP tumors were castrated and given hIgG or LTβR-Ig (100 μg) every 5 days, starting 4 days before castration. Tumor volume was measured as above. Results are averages±s.e.m. D. Tumors were established using myc-CaP cells transduced with lentiviruses expressing scrambled (sc) siRNA or LTβ-specific siRNA. Mice were castrated and tumor volume was measured. Results are averages±s.e.m. (n=10). E. Myc-CaP cells (previously infected with lentiviruses expressing scrambled or IKKα siRNAs) were plated at 40% confluency. After 6 hrs, the cells were cultured with or without flutamide (10 μM) in the absence or presence of LTα$_2$β$_1$, and cell number was determined. F. Myc-CaP cells were plated at 60% confluency. After 12 hrs, cells were stimulated for 1 hr with LTα$_2$β$_1$, collected, divided into cytosolic (C) and nuclear (N) fractions and IKKα and histone H3 distribution was determined. In A, B, C, D and E, P values were determined and are indicated as above.
Figure 22:
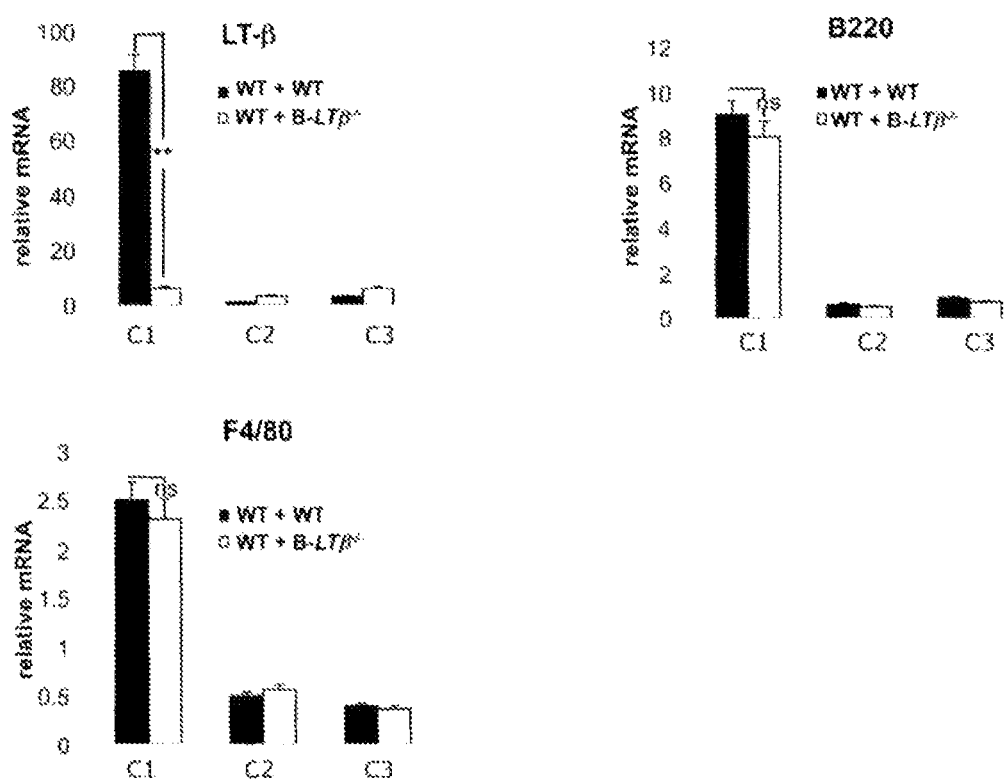
FIG. 22. B cell-specific LTβ knockout abolishes LTβ expression in tumors but has no effect on B cell and macrophage infiltration. Lethally irradiated FVB males were reconstituted with BM from B-Ltβ$^{-/-}$ mice as described above. Tumors were established and collected at the indicated times after castration. Total RNA was isolated and expression of the indicated mRNAs was quantitated by Q-PCR and normalized to that of cyclophilin A mRNA. Results are averages±s.d. (n=5). P values were determined and depicted as above.
Figure 23:
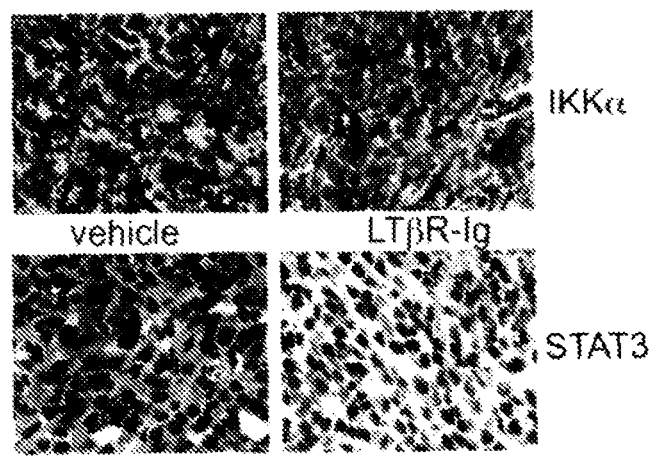
FIG. 23. LTβ is required for IKKα nuclear localization and STAT3 phosphorylation. Mice carrying Myc-CaP tumors were castrated and treated with vehicle or LTβR-Ig as described above. Paraffin-embedded sections were analyzed for IKKα nuclear localization and STAT3 phosphorylation.

To examine whether LT production by tumor-infiltrating lymphocytes stimulates CR-CaP growth, we transplanted BM from B-Ltβ$^{-/-}$ or T-Ltβ$^{-/-}$ mice, which lack LTβ in either B or T cells[21], into lethally irradiated mice. LTβ ablation in B cells, but not in T cells, delayed growth of CR-CaP (FIG. 4B) and abolished LTβ expression within tumors but did not prevent B cell or macrophage infiltration (FIG. 22). Treatment of mice with the LTβR-Ig decoy[22] was as effective as B cell-specific LTβ ablation in delaying CR-CaP growth (FIG. 4C) and prevented IKKα and STAT3 activation (FIG. 23). Silencing of LTR in Myc-CaP cells (FIG. 19B) also delayed CR-CaP growth (FIG. 4D). Exogenous LT maintained myc-CaP growth in the presence of flutamide, a clinically used AR antagonist[3], in a manner dependent on IKKα (FIG. 4E), whose nuclear translocation was LT inducible (FIG. 4F).

Example 8

Discussion of Examples 1-7

Figure 24:
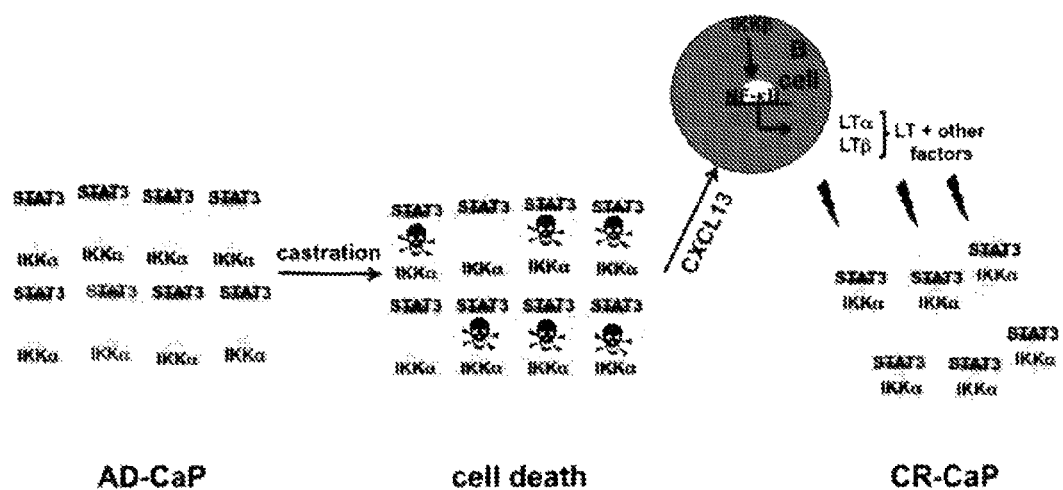
FIG. 24. A model explaining how therapy-induced inflammation promotes emergence of CR-CaP. Androgen withdrawal causes death of primary AD-CaP cells, which release inflammatory mediators that lead to chemokine induction and recruitment of inflammatory cells, including B cells, into the tumor remnant. IKKβ activation in B cells results in NF-κB-dependent production of LT and other factors that activate IKKα and STAT3 in surviving CaP cells. This results in survival and re-growth of CR-CaP.

Data herein in Examples 1-8 demonstrate that an inflammatory response triggered by death of androgen-deprived primary cancer is another important contributor to emergence of CR-CaP. In addition to dying CaP cells, critical participants in this response are tumor infiltrating B cells, which produce LTα:β heterotrimers that stimulate LTβR on CaP cells to induce IKKα nuclear translocation and STAT3 activation, thereby enhancing androgen-independent growth (FIG. 24). Interference with any component of this response results in a significant and reproducible 3-4 week delay in appearance of CR-CaP.

Extrapolation from "mouse time" to "human time" suggests that interventions that prevent LT production or signaling may delay appearance of CR-CaP in patients undergoing androgen ablation therapy by 2.3 to 3.1 years.

Importantly, our results suggest that, at least for CaP, the inflammatory response elicited by the dying primary tumor, contributes to the failure rather than the previously proposed success of anti-cancer therapy[23]. Without limiting the invention to a particular mechanism, in one embodiment, necrotic cell death releases mediators, such as HMGB1[24] and IL-1α[25], that activate IKKβ and NF-κB and stimulate production of chemokines, one of which, CXCL13, recruits B cells into the regressing tumor. Notably, TIBC were detected not only in androgen-deprived mouse CaP, but also in human CaP. Although B cells were reported to promote progression of skin carcinomas[9] and exert immunosuppressive effects through activation of inhibitory Fc receptors on myeloid cells[26], the critical tumor promoting B cell function in our experimental model is production of LT, an IKKα-activating cytokine[27], which promotes survival of androgen-deprived CaP. Another important function of TIBC is activation of STAT3, an anti-apoptotic and pro-tumorigenic transcription factor[28]. Without limiting the invention to a particular mechanism, although the STAT3-activating cytokine in this system is not identified, in one embodiment, castration induces expression of STAT3-activating IL-6 and IL-12 family members. Furthermore, CaP cells use autocrine IL-6 to stimulate their progression[29] and activated STAT3 promotes ligand-independent AR activation[29]. LT is also involved in the etiology of human CaP. An epidemiological study revealed that reduced CaP risk due to consumption of non-steroidal anti-inflammatory drugs, such as aspirin, is limited to men who express a common polymorphic LTα allele that specifies high LT production[30]. Data herein in Examples 1-7 demonstrate that individuals who are high LT producers are more likely to develop CR-CaP and thus would benefit from anti-LT therapy.

Example 9

Methods used in Examples 10-16

Mice

Mice were maintained under specific pathogen-free conditions, and experimental protocols were approved by the University of California, San Diego Animal Care Program, following National Institutes of Health (NIH) guidelines. TRAMP mice (Gingrich et al., 1996) were intercrossed with Ikkα$^{AA/AA}$ mice (Cao et al., 2001) for six generations to generate Ikkα$^{AA/AA}$/TRAMP and Ikkα$^{AA/+}$/TRAMP mice that were of the FVB background. Males were allowed to reach 12 weeks of age when they were castrated or sham operated as described (Watson et al., 2005). Tumors were harvested 12 weeks later. For myc-CaP tumor growth, 3×10$^6$ cells were s.c. injected into 6 weeks old FVB mice (Watson et al., 2005). Tumors were allowed to reach 500-1000 mm$^3$ before mice were castrated. Tumors were then harvested at the indicated times. For prostate regeneration studies, 6 weeks old FVB mice (Ikkα$^{AA/+}$, Ikkα$^{AA/AA}$, J$_H^{-/-}$ or WT) were castrated. After 7 days, the mice received 3 s.c. injections of 5 ug of testosterone propionate once every 4 days.

Human Specimens

Anonymous human prostate, benign prostatic hyperplasia and prostate cancer frozen sections accompanied by pathology reports were provided by the Cooperative Human Tissue Network.

Histological Procedures

Tumors and prostates were immersed in 10% neutral buffered formalin before sectioning and paraffin embedding. Sections were stained and processed as described (Luo et al., 2007), using haematoxylin and eosin (H&E), or antibodies for IKKα (Imgenex), BMI1 (Millipore) CD133 and p63 (Santa Cruz Biotechnologies), and ubi-H2A (Millipore) as described. The density of nuclear staining was determined using Adobe Photoshop as described (Lehr et al., 1997).

Analysis of RNA and Protein Expression

Total tissue RNA was prepared using RNAeasy (Qiagen). Quantitative PCR was performed as described (Luo et al., 2004). Cells and tissues were lysed and analysed by SDS-PAGE and immunoblotting with antibodies to BMI1 (Millipore), β-tubulin (Sigma), IKKα (Imgenex), E2F1 (Sc-251), CBP (A-22) or HA (Roche). Nuclear extracts were prepared and analyzed for DNA binding as described (Ammirante et al., 2010).

Lentiviral Transduction siRNAs to mouse IKKα and BMI1 were cloned into pLSLPw, provided by I. Verma (the Salk Institute), and lentivirus stocks were prepared as described (Luo et al., 2007). Virus-containing supernatants were added to myc-CaP cells for 2 days with polybrene, and transduced cells were selected in 5 μg ml$^{-1}$ puromycin (Invitrogen).

Statistical Analyses

Results are expressed as means±s.e.m. or s.d. Data were analyzed by Student's t-test using the GraphPad Prism statistical program. Error bars depict s.e.m. or s.d. P values >0.05 were considered insignificant, 0.01-0.05 were considered significant, 0.001-0.01 were considered very significant and <0.001 were considered highly significant.

Chromatin Immunoprecipitation

Chromatin immunoprecipitation was performed as described (Kuraishy et al., 2007). Briefly, fresh tumors were harvested, minced using razor blades, and cross-linked with 10% formaldehyde for 10 min. The reactions were then quenched using glycine and the tumors were digested with collagenase for 3 hrs. Single cell suspensions were used to prepare chromatin that was immunoprecipitated with antibodies to IKKα, BMI1, acetylated-H3, and Ubi-H2A (Millipore), and E2F1 and CBP (Santa Cruz Biotechnologies). The primers used were as follows:

```
Bmi1 promoter forward-
5' AAAGGCAGAGATCGGGAGAGA 3'

Bmi1 promoter reverse-
5' GGCCGAGCCGTATTATTCTGC 3'

Intergenic Chr. 8 forward-
5' TTGGTGGGCCAATTTCTTCTGTGG 3'

Intergenic Chr. 8 reverse-
5' TCCTCCTCAGGCTCAAATGCATGA 3'

Ink4A/Arf LOCUS #1 forward-
5' GAGTACAGCAGCGGGAGCAT 3'
```

-continued

```
Ink4A/Arf LOCUS #1 reverse-
5' GAACTTCACCAAGAAAACCCT 3'

Ink4A/Arf LOCUS #2 forward-
5' GTCCGATCCTTTAGCGCTGTT 3'

Ink4A/Arf LOCUS #2 reverse-
5' AGCCCGGACTACAGAAGAGAT 3'

Ink4A/Arf LOCUS #3 forward-
5' CCGGAGCCACCCATTAAACTA 3'

Ink4A/Arf LOCUS #3 reverse-
5' CAAGACTTCTCAAAAATAAGA 3'
```

EMSA

Nuclear extracts were prepared from tumors by incubation with Buffer A (25 mM HEPES pH 7.6, 0.1 mM EDTA, 10% glycerol, 1 mM DTT, 0.1 mM PMSF), homogenization, passing through an insulin syringe 5 times and spinning down nuclei. The resulting pellets were resuspended in Buffer B (Buffer A+450 mM KCl) for 1 hr. 293T cell proteins were immunoprecipitated 48 hrs after transfection with anti-HA (Roche) and washed 3 times in RIPA lysis buffer. Immunecomplexes were eluted using an HA-peptide (Sigma) and added to EMSA binding buffer (10 mM HEPES, 1.5 mM $MgCl_2$, 1 mM EDTA, 0.5 mM DTT, 0.5 mM PMSF, 10 mM KCl and 10% glycerol), with 1 ug poly dI:dC and 1 ug of BSA. Nuclear extracts were added to same buffer. Probes were added and the mixtures incubated for 20 min in room temperature and gel separated at 4° C. For UV crosslinking experiments, probes and proteins were co-incubated and placed in a UV Stratalinker 2400 (Stratagene) for 10 min. The complexes were then immunoprecipitated with anti-HA, separated by SDS-PAGE and visualized by autoradiography.

Example 10

Castration-Induced Inflammation Controls BMI1 Expression via IKKα

Figure 25:
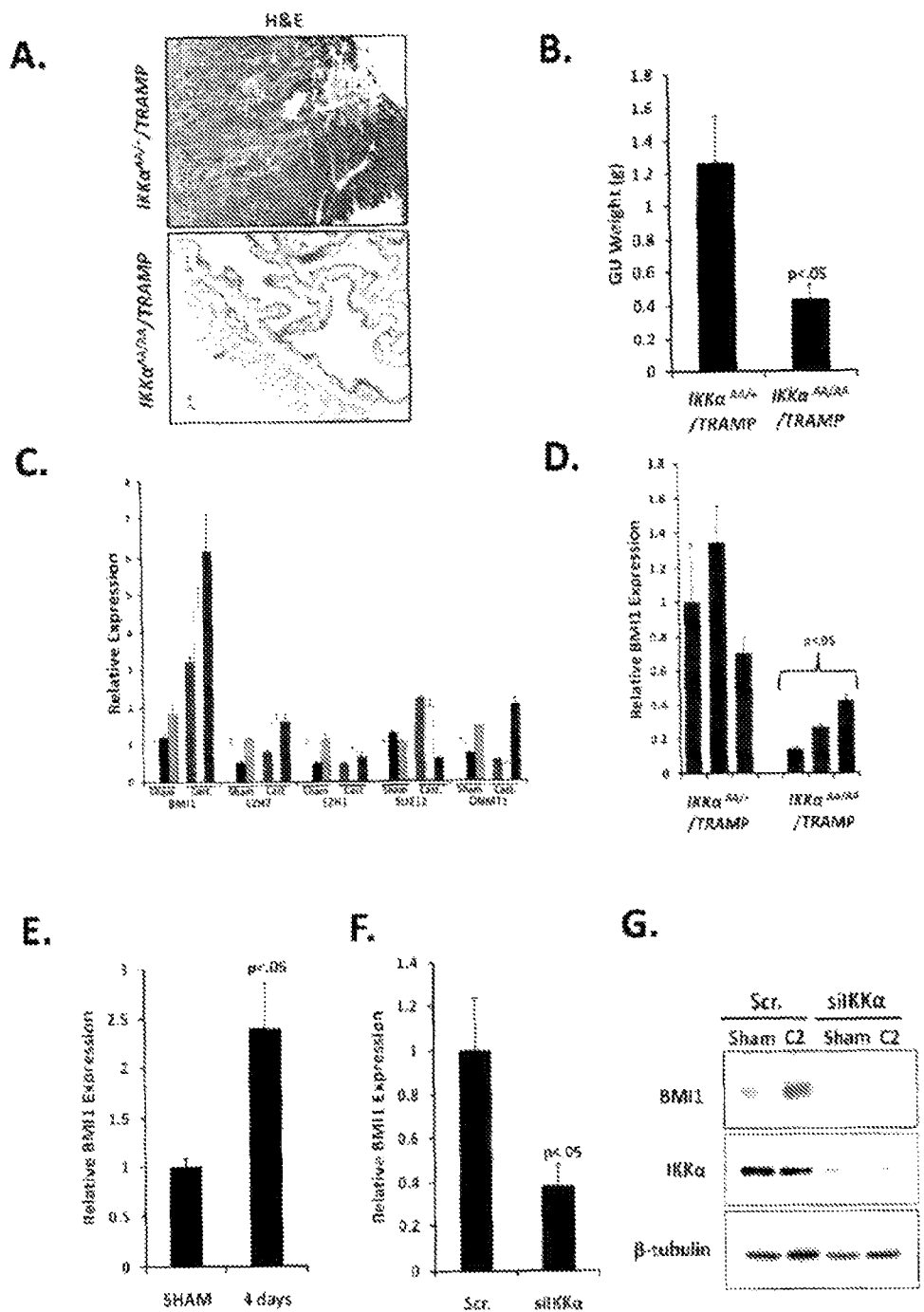
FIG. 25: IKKα is required for growth of castration-resistant tumors and BMI1 Induction. A) Histological analysis (H & E staining of paraffin-embedded sections; magnification-40×) of prostates from 24 weeks old Ikkα$^{AA/+}$/TRAMP and Ikkα$^{AA/AA}$/TRAMP mice that were castrated at 12 weeks of age. B) Impact of castration on GU weight in the mice described in A. C) Prostate RNA from 24 weeks old Ikkα$^{AA/+}$/TRAMP mice (castrated or sham operated at 12 weeks) was analyzed for expression of PcG genes and DNMT1. D) Prostate RNA from 24 weeks old mice of indicated genotypes castrated at 12 weeks of age, was analyzed for Bmi1 gene expression. E) RNA from s.c. myc-CaP tumors collected 4 days after castration or sham operation was analyzed for Bmi1 expression. F) RNA from s.c. myc-CaP tumors formed by mock (Scr.) or IKKα-silenced cells was collected 2 weeks after castration and analyzed for Bmi1 expression. G) Protein extracts from mock-(Scr) or IKKα-silenced tumors were analyzed by immunoblotting for Bmi1 expression 2 weeks after castration or sham operation. In panels B-F, the values represent means±SD (n=3).

Using subcutaneous (s.c.) allografts of the mouse androgen-dependent myc-CaP cell line (Ellwood-Yen et al., 2003), we demonstrated that RNAi-mediated IKKα silencing retards the growth of CR-PCa (Ammirante et al., 2010; FIG. 32A). However, myc-CaP tumors are extremely aggressive and we have not succeeded in delaying their regrowth by more than 3-4 weeks upon IKKα silencing, B cell ablation, CXCL13 neutralization or LT antagonism (Ammirante et al., 2010). We therefore examined whether IKKα inhibition affects growth of CR-PCa in TRAMP mice, which develop prostate adenocarcinoma within 12 weeks of age due to expression of SV40 T antigen from the prostate-specific probasin (PB) promoter (Greenberg et al., 1995). Castration of TRAMP mice leads to temporary tumor regression followed by emergence of CR-PCa that is more aggressive and more metastatic than the initial tumor (Hurwitz et al., 2001). We crossed TRAMP mice to $Ikk\alpha^{AA}$ mice, in which the activation loop serines whose phosphorylation is required for IKKα activation are replaced with alanines (Cao et al., 2001). As shown previously (Luo et al., 2007), homozygocity for the $Ikk\alpha^{AA}$ allele results in only a small retardation in primary tumor growth (FIG. 32B). At 12 weeks of age, TRAMP males that were either heterozygous or homozygous for the $Ikk\alpha^{AA}$ allele were castrated to mimic androgen withdrawal (FIG. 32C). After 12 additional weeks, prostates of these mice were subjected to histological analysis by hemotoxylin and eosin (H & E) staining which revealed striking differences between $Ikk\alpha^{AA/+}$/TRAMP and $Ikk\alpha^{AA/AA}$/TRAMP tissues, with the heterozygous glands exhibiting a much higher degree of cellularity and loss of prostatic architecture due to tumor growth compared to prostates of homozygous mice (FIG. 25A). Castrated $Ikk\alpha^{AA/AA}$/TRAMP mice also exhibited a considerable reduction in genitourital (g.u.) weight at 24 weeks of age relative to $Ikk\alpha^{AA/+}$/TRAMP mice (FIG. 25B). Castration also induced nuclear translocation of IKKα in PCa of $Ikk\alpha^{AA/+}$/TRAMP mice (FIG. 32D).

The role of IKKα in CR-PCa formation is unlikely to be exerted via NF-κB, as deletion of IKKβ, the primary NF-κB activator in prostate epithelial cells of TRAMP mice or in myc-CaP tumors, had no effect on CR-PCa (Ammirante et al., 2010). Because other studies have suggested an NF-κB-independent role for nuclear IKKα in regulating histone modifications and chromatin structure (Anest et al., 2003; Yamamoto et al., 2003), we examined whether IKKα controls expression of polycomb group (PcG) proteins during CR-PCa development. PcG proteins are histone modifying enzymes whose expression has been implicated in PCa progression, stage and clinical outcome (Berezovska et al., 2006; Varambally et al., 2002; Yu et al., 2007). While expression of the PcG genes Ezh1, Ezh2, Suz12 and the DNA methyltransferase Dnmt1 was not affected by castration of TRAMP mice, expression of Bmi1, encoding a critical component of the histone-ubiquitinating PRC1 complex (Konuma et al., 2010; Wang et al., 2004), was significantly elevated in castrated mice (FIG. 25C). This increase was not seen after castration of $Ikk\alpha^{AA/AA}$/TRAMP mice indicating a dependency on IKKα activation (FIG. 25D). An effect of castration on BMI1 expression was also observed in myc-CaP allografts, and was also IKKα dependent (FIGS. 25E-G, 32E). Because we have previously reported immune infiltration into PCa of castrated mice (Ammirante et al., 2010) and Bmi1 expression is high in some immune cell subsets (Konuma et al., 2010), we isolated epithelial cells from the tumors and confirmed that IKKα-dependent upregulation of Bmi1 mRNA took place within these cells (FIG. 32F).

Example 11

Nuclear IKKα Stimulates Bmi1 Transcription

Figure 26:
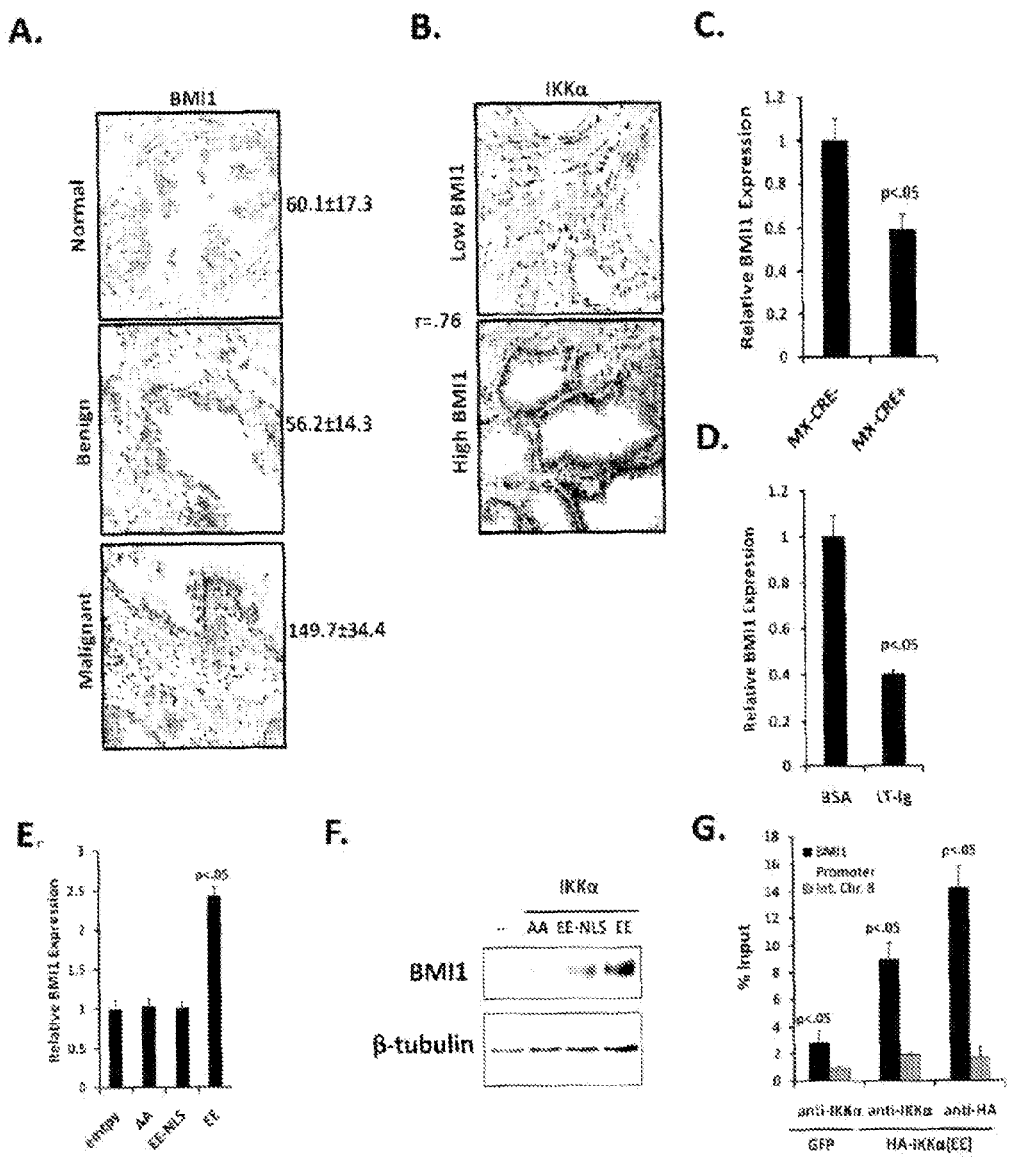
FIG. 26: IKKα controls BMI1 expression in prostate cancer. A) Paraffin-embedded prostate sections representing normal tissue (n=9), benign prostatic hyperplasia (n=8), and prostate cancer (n=13) were analyzed by immunohistochemistry for BMI1. The BMI1 staining index was quantitated by Adobe Photoshop and is indicated on the right (p-value is <0.001 for the malignant samples). B) Prostate cancer specimens from A with low and high BMI1 staining indices were evaluated for IKKα expression (n=4 for each group). The correlation coefficient is indicated on the left. C) RNA collected from myc-CaP tumors established in Ikkβ$^{F/F}$/Mx1-CRE and Ikkβ$^{F/F}$ mice 2 weeks after castration and analyzed for Bmi1 expression. To induce CRE expression, host mice were injected with polyI:C 2 days before castration. D) RNAs collected from myc-CaP tumors grown in mice that were given hIgG or LTβR-Ig (100 ug) every 5 days, starting 4 days before castration, were analyzed for Bmi1 expression 2 weeks after casliation. E) RNA samples from myc-CaP cells collected after stable infection with lentiviruses harboring different IKKα constructs (AA=inactivateable, EE-NLS=constitutively active and unable to translocate to the nucleus, EE=constitutively active) were analyzed for Bmi1 gene expression. F) Lysates of myc-CaP cells collected after stable infection with the above viruses were analyzed for BMI1 expression by immunoblotting. G) ChIP analysis of IKKα recruitment to the Broil promoter. Chromatin isolated from myc-CaP cells stably infected with lentiviruses harboring a GFP or an IKKα(EE) insert was formaldehyde crosslinked, sheared and immunoprecipitated with IKKα or HA antibodies and analyzed by qPCR with primers to the Bmi1 promoter or an intergenic region of chromosome 8. % input was calculated by determining the ratio of immunoprecipitated DNA with each antibody to a 10% input sample. In panels C-E and G, the values represent means±SD (n=3).
Figure 33:
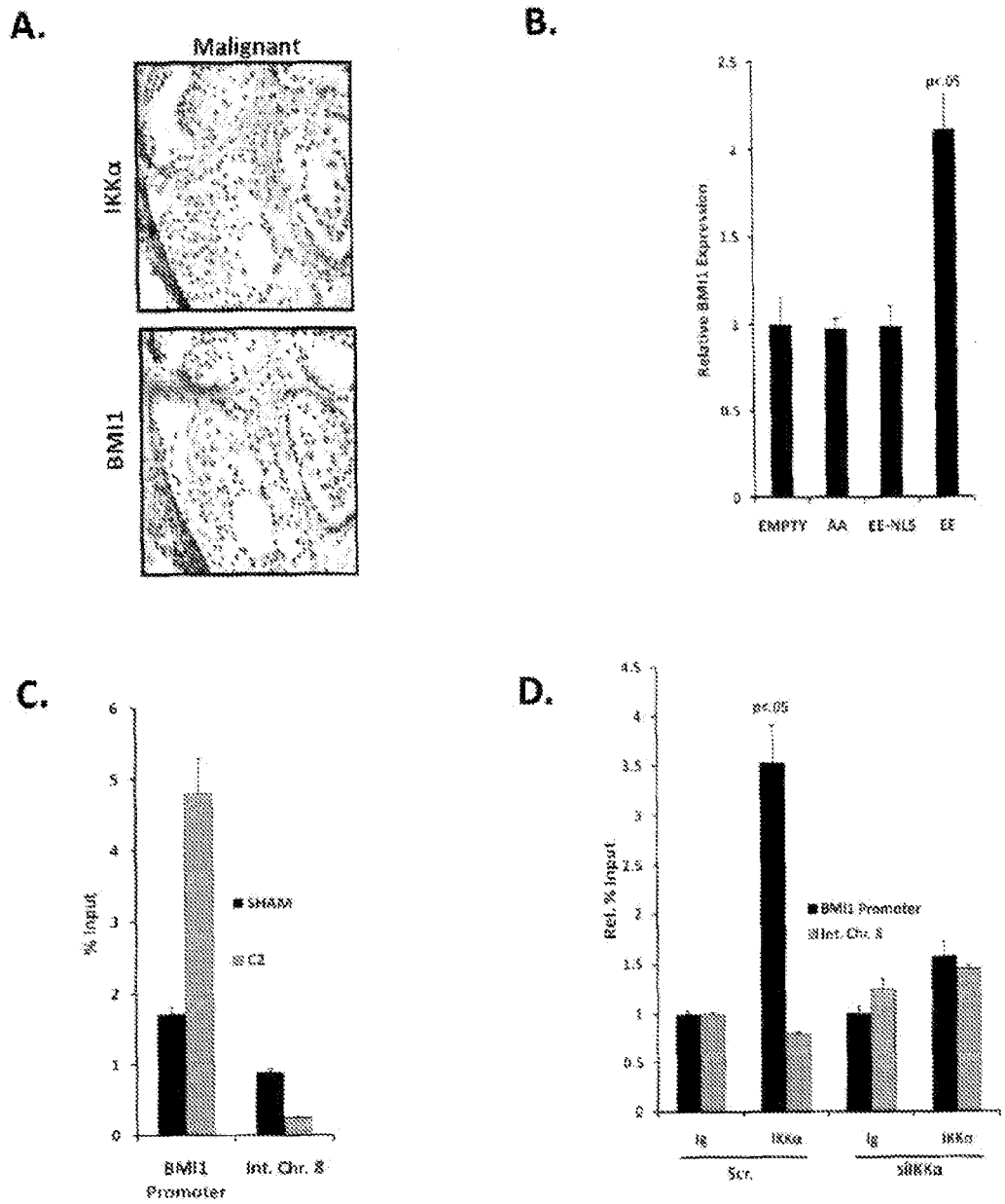
FIG. 33: Bmi1 induction requires IKKα activation and nuclear translocation A) Sequential paraffin-embedded sections of human PCa were analyzed by immunohistochemistry for IKKα and BMI1. B) DU145 human PCa cells were transduced with lentiviruses harboring different IKKα constructs. After 2 weeks in culture, RNA was collected and analyzed for Bmi1 expression. C) Myc-CaP tumors collected 2 weeks after sham operation or castration were subjected to ChIP analysis using an IKKα antibody and primers to the Bmi1 promoter or an intergenic region of Ch-8. % input was calculated by determining the ratio of immunoprecipitated DNA to a 10% Input sample. D) s.c. myc-CaP tumors generated by s.c. transplanted mock (Scr.)- or IKKα-silenced cells were collected 2 weeks after castration or sham operation and subjected to ChIP analysis using IKKα antibody or control IgG and primers to the Bmi1 promoter or an intergenic region of Ch-8. % input was calculated as above. In panels B-D, the values represent means±SD (n=3).

Adding further significance to our findings, BMI1 upregulation was seen in human PCa but not in benign prostatic hyperplasia (FIG. 26A). We also found a correlation between nuclear IKKα and high BMI1 expression in human PCa (FIG. 26B), and staining of sequential PCa sections revealed high BMI1 expression in cells with nuclear IKKα (FIG. 33A).

To examine the role of IKKα activation by inflammatory signals and Bmi1 expression, we inhibited IKKα activation in mice bearing myc-CaP tumors either by IKKβ ablation in bone marrow derived cells or by injection of a LTβR-Fc fusion protein, which inhibit CR-PCa formation and IKKα nuclear translocation (Ammirante et al., 2010). Both treatments inhibited Bmi1 mRNA expression in tumors of castrated mice (FIG. 26C,D). To examine the role of IKKα nuclear translocation in Bmi1 transcription more directly, we infected myc-CaP cells with lentiviral expression vectors encoding different isoforms of HA-tagged IKKα and examined effects on BMI1 expression. Constitutively active IKKα (IKKα(EE)), in which the activation loop serines were replaced with phosphomimetic glutamate residues (Senftleben et al., 2001), increased BMI1 mRNA and protein amounts (FIG. 26E,F). However, the inactivateable IKKα(AA) construct was ineffective and an IKKα(EE) construct with a defective nuclear localization signal (NLS) (IKKα(EE-NLS)) (Sil et al., 2004) was also a poor inducer of BMI1 expression. Ruling out the possibility that this phenomenon was murine-specific, similar results were obtained in the human PCa cell line DU145 (FIG. 33B). These data strongly suggest that active IKKα that can enter the nucleus upregulates Bmi1 transcription.

Nuclear IKKα can associate with certain genes and modulate their expression (Anest et al., 2003; Luo et al., 2007; Yamamoto et al., 2003). We therefore performed chromatin immunoprecipitation (ChIP) experiments to examine whether IKKα is recruited to the Bmi1 promoter. In HA-IKKα(EE) expressing myc-CaP cells, ChIP with either IKKα or HA antibodies revealed an association between active IKKα and the Bmi1 promoter (FIG. 26G). Furthermore, using chromatin from myc-CaP allograft tumors, an association between endogenous IKKα and the BMI1 promoter was seen 2 weeks after castration but not in sham operated mice (FIG. 33C) Indicating specificity, this association was not seen in castrated mice inoculated with myc-CaP cells whose endogenous IKKα was silenced (FIG. 33D).

Example 12

IKKα Interacts with the Bmi1 Promoter via E2F1

Figure 27:
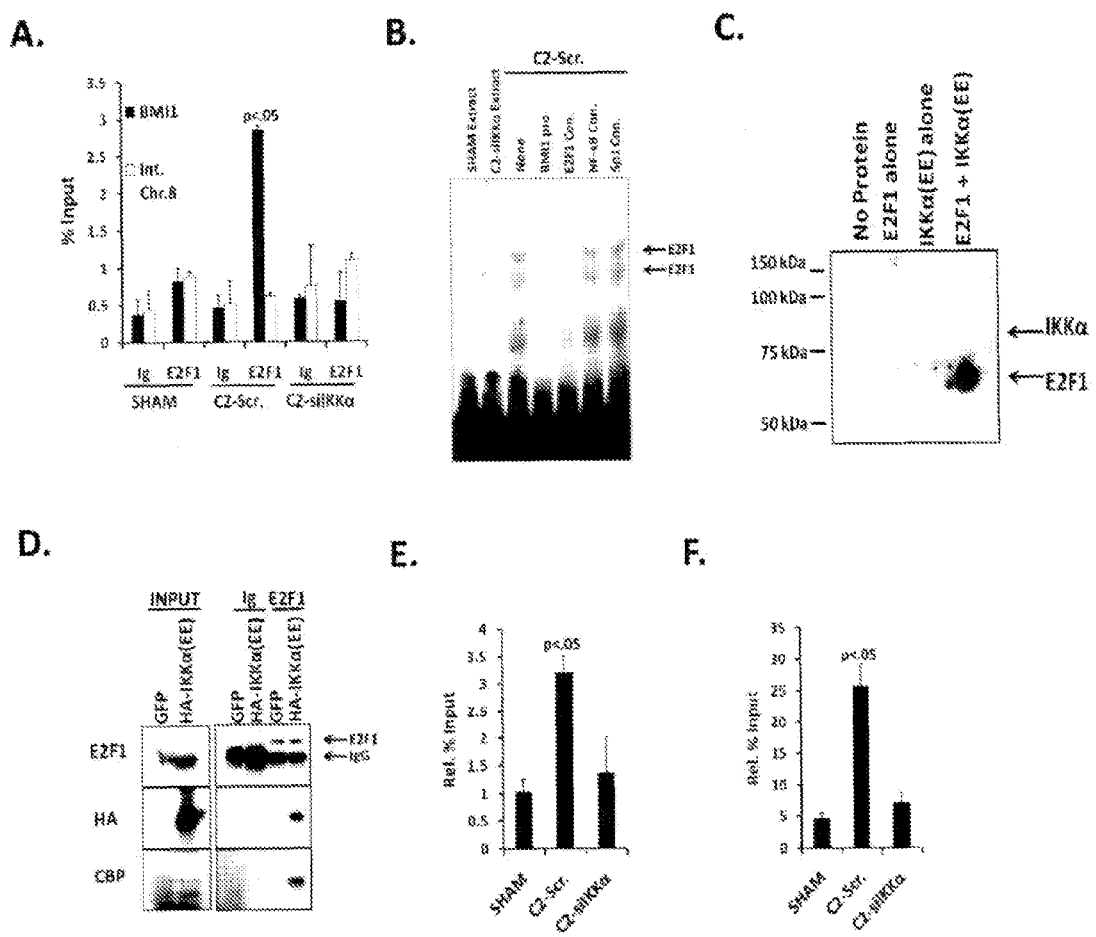
FIG. 27: IKKα interacts with E2F1 and controls its recruitment to the Bmi1 promoter. A) Chromatin was isolated from myc-CaP tumors established by mock (Scr.)- or IKKα-silenced cells 2 weeks after sham operation or castration. After crosslinking and shearing, chromatin was immunoprecipitated with antibodies to E2F1 or control IgG and the content of Bmi1 promoter DNA was determined by qPCR as in 2G. B) Nuclear extracts were prepared from the myc-CaP tumors described above and the presence of E2F DNA binding activity was analyzed by electrophoretic mobility shift assay using the putative Bmi1 E2F1 binding site as a probe. For competition experiments, 100-fold excess of non-radioactive competitor oligonucleotides representing the Bmi1 E2F1 site or consensus binding sites of the indicated transcription factors were added to the reactions 10 min. before addition of the radioactive probe. C) Binding of E2F1 and IKKα to the putative Bmi1 E2F1 binding site was analyzed by UV crosslinking. Extracts from 293T cells transfected with HA-tagged E2F1 or IKKα expression constructs were immunoprecipitated with HA antibody and incubated with the Bmi1 E2F site probe described in B. The samples were then UV-crosslinked, separated by SDS-PAGE and autoradiographed. D) IKKα mediates recruitment of CBP to E2F1. 293T cells were transfected with GFP or IKKα(EE) vectors. After 48 hrs, the cells were lysed and immunoprecipitated with an E2F1 or Ig control antibodies. Immunoblotting was then performed using the indicated antibodies. E, F) Chromatin was harvested from the myc-CaP tumors described in A and subjected to ChIP analysis as above with antibodies to CBP (E) or Ac-H3 (F). Relative % input was determined as above. In panels A, E and F, the values represent means±SD (n=3).

As IKKα has no recognizable DNA-binding domain and is unlikely to bind DNA directly, we hypothesized that IKKα is recruited to the Bmi1 promoter through an interaction with a sequence-specific transcription factor. After ruling out involvement of NF-κB in IKKα recruitment (data not shown), we examined whether IKKα interacts with E2F1, as the latter was reported to bind and activate the Bmi1 promoter (Nowak et al., 2006) and recruit IKKα to certain target genes (Tu et al., 2006). ChIP experiments with an E2F1 antibody demonstrated that like IKKα, E2F1 bound to the Bmi1 promoter only after castration and in an IKKα-dependent manner (FIG. 27A). To confirm the IKKα-dependence of E2F1 binding to the BMI1 promoter, we performed electophoretic mobility shift assays (EMSAs) with nuclear extracts from myc-CaP tumors and a 30 bp oligonucleotide representing the E2F1 binding site from the Bmi1 promoter. This experiment supported the ChIP results as it revealed E2F-specific protein-DNA complexes only in lysates of IKKα-expressing myc-CaP tumors isolated 2 weeks after castration (FIG. 27B). These differences are not due to any effects of IKKα or castration on E2F1 expression (FIG. 34A). c-Myc is another Bmi1 transcriptional activator (Guo et al., 2007), but its association with the Bmi1 promoter in myc-CaP cells was not affected by castration (FIG. 34B). To further confirm the IKKα-dependency of E2F1 binding to the Bmi1 promoter, we immunoprecipitated HA-tagged IKKα(EE) and E2F1 from transiently transfected 293T cells and performed UV-crosslinking experiments to determine which protein directly contacts the Bmi1 E2F1 binding site. This analysis revealed a radiolabeled band at approximately 60 kDa (the molecular weight of E2F1) and a very faint band around 85 kDa (the molecular weight of IKKα); both bands appeared only if E2F1 was co-expressed with activated IKKα (FIG. 27C). Neither E2F1 nor IKKα (EE) alone exhibited detectable interaction with the BMI1 E2F1 binding site.

Co-immunoprecipitation experiments in 293T cells revealed an interaction between E2F1 and activated IKKα (FIGS. 27D and 34C). We also examined whether IKKα regulates E2F1 activity via CBP, which acetylates E2F1 to increase its stability and DNA binding activity (Galbiati et al., 2005; Ianari et al., 2004; Trouche and Kouzarides, 1996; Tu et al., 2006) and can be recruited to certain promoters via IKKα (Hoberg et al., 2006; Huang et al., 2007). Co-immunoprecipitation revealed an interaction between E2F1 and CBP, but only in the presence of IKKα (FIG. 27D). ChIP experiments supported these results by revealing IKKα-dependent recruitment of CBP to the Bmi1 promoter after castration (FIG. 27E). These experiments suggest that IKKα recruits CBP to E2F1 resulting in E2F1 acetylation and stabilization. E2F1 then recruits the complex containing IKKα and CBP to the Bmi1 promoter. This model is further supported by IKKα-dependent and castration-induced H3 acetylation at the Bmi1 promoter in myc-CaP tumors (FIG. 27F). In additional experiments, we found that transient transfection of an E2F1 expression vector into myc-CaP cells led to 3-fold increase in Bmi1 mRNA expression that was IKKα-dependent (FIG. 34D). Collectively, these results suggest that IKKα stimulates Bmi1 transcription through its interaction with E2F1 (or a closely related factor) and CBP (or p300).

To determine if the functional cooperation between IKKα and E2F1 was unique to the Bmi1 gene, we examined binding of E2F1 to the Ccne (cyclin E) promoter, a well-documented E2F1 target (Ohtani et al., 1995). Similar to the Bmi1 promoter, E2F1 was recruited to the Ccne promoter only after castration and in an IKKα-dependent manner (FIG. 34E). Furthermore, castration-induced expression of cyclin E was IKKα-dependent (FIG. 34F). Thus, IKKα activation is important for the transcriptional induction of several E2F1 targets during castration.

Example 13

BMI1 is Required for Castration-Resistant Tumor Growth

Figure 28:
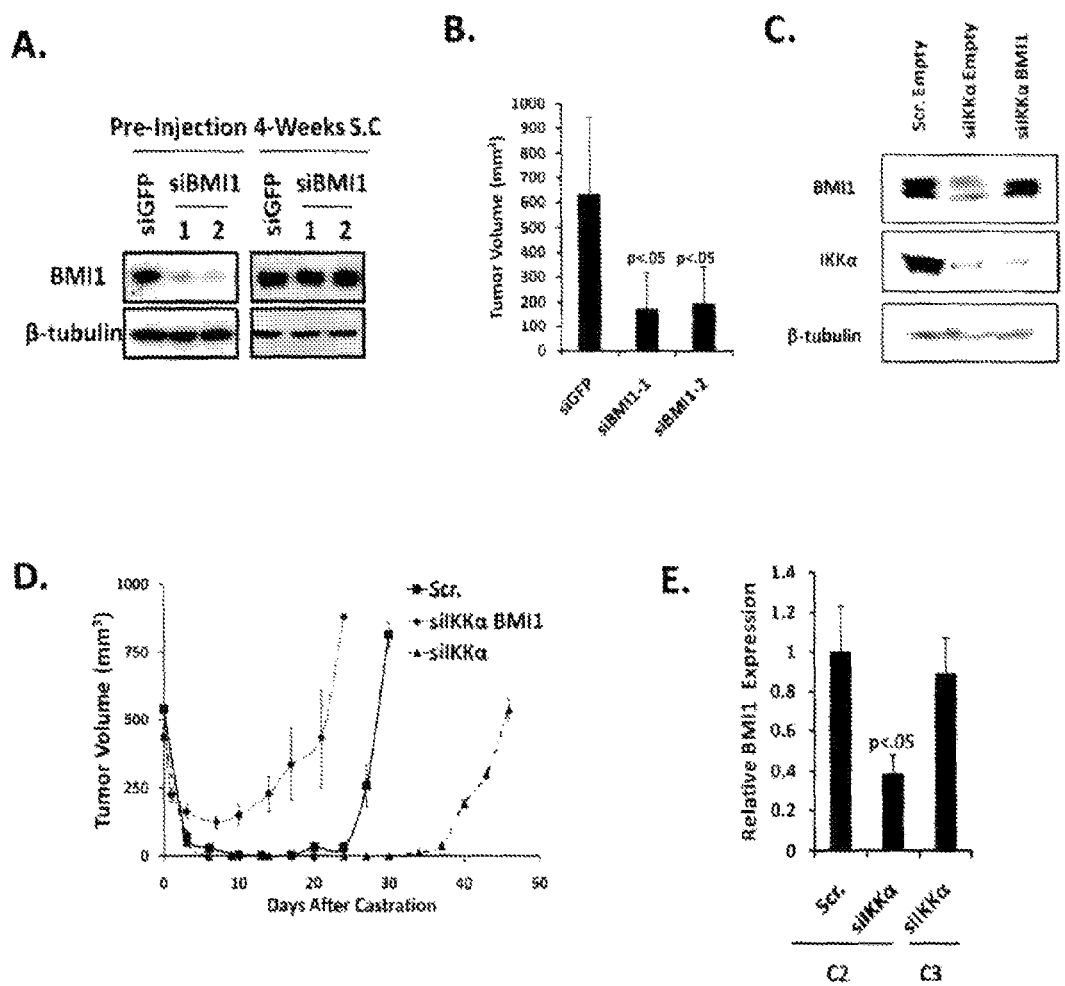
FIG. 28: BMI1 controls castration resistant tumor growth. A) Myc-CaP cells that were infected with lentiviruses expressing siRNA to GFP (siGFP) or Bmi1 (siBMI1-1 and -2) were analyzed for BMI1 expression by immunoblotting after 2 weeks in culture or 4 weeks after s.c. tumor growth. B) Sizes of tumors formed by s.c. injection of myc-CaP cells described in A, were determined 4 weeks after inoculation. C) Protein extracts from s.c. myc-CaP tumors formed by mock (Scr.), IKKα-silenced or IKKα-silenced+BMI1 lentiviral transduction were analyzed for BMI1 expression 2 weeks after castration. D) myc-CaP tumors were established in wild-type mice using cells from C. When tumors reached 500 mm$^3$, the mice were castrated. Tumor volume was then measured at the indicated time points. E) RNA from s.c. myc-CaP tumors formed by mock (Scr.) or IKKα-silenced cells was collected 2 or 3 weeks after castration and analyzed for Bmi1 expression. In panels B, D and E, the values represent means±SD (n=3).

To determine if BMI1 is needed for CR-PCa regrowth, we used RNAi to deplete BMI1 in myc-CaP cells. Using two different siRNAs, we were able to achieve a considerable reduction in BMI1 protein amounts (FIG. 28A). However, after 4 weeks of s.c. tumor growth, BMI1 expression was restored. Nonetheless, BMI1 silencing led to a significant reduction in primary tumor growth (FIG. 28B). We ectopically expressed BMI1 in myc-CaP cells whose IKKα expression was silenced with siRNA (FIG. 28C). Unlike BMI1-silenced cells, IKKα-deficient myc-CaP cells retained IKKα silencing after s.c. growth, which was IKKα-independent prior to castration (Ammirante et al., 2010). IKKα silencing delayed the regrowth of CR-PCa by about 3 weeks, but ectopic expression of BMI1 in IKKα-silenced cells strongly enhanced their regrowth in castrated mice (FIG. 28D). In fact, BMI1 transduced cells re-grew faster than the parental myc-CaP cells after castration. Curiously, 3 weeks after castration IKKα-silenced myc-CaP cells have managed to regain BMI1 expression (FIG. 28E), thus explaining the temporary nature of the delay in tumor regrowth caused by IKKα silencing in myc-CaP cells.

BMI1 was suggested to promote cell proliferation and inhibit senescence through epigenetic silencing of the $p16^{Ink4a}/p19^{Arf}$ locus (Jacobs et al., 1999). Consistent with this notion, tumors formed by IKKα-silenced myc-CaP cells exhibited elevated p16 and p19 expression, but ectopic expression of BMI1 in IKKα-silenced myc-CaP tumors reduced p16 and p19 expression to their basal levels (FIG.

Figure 29:
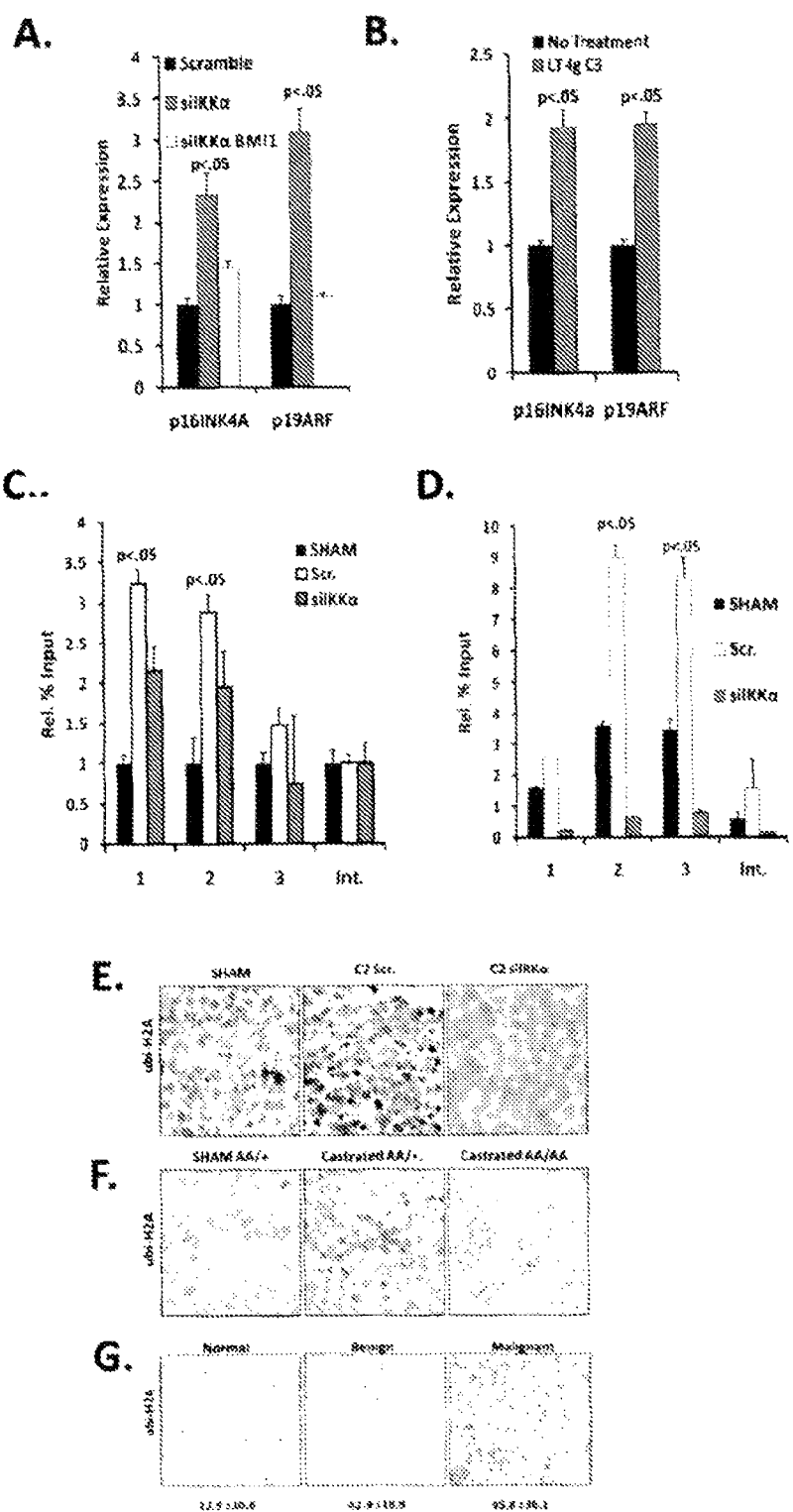
FIG. 29 BMI1 controls p16 and p19 expression in prostate cancer. A) RNAs from s.c. myc-CaP tumors formed by mock (Scr.), IKKα-silenced, or IKKα-silenced+BMI1 transduced cells were analyzed for p16 and p19 expression 2 weeks after castration. B) RNAs collected from myc-CaP tumors described in FIG. 26D were analyzed for p16 and p19 expression 2 weeks after castration. (C, D) Chromatin isolated from s.c. myc-CaP tumors formed by mock (Scr.) or IKKα-silenced cells 2 weeks after sham operation or castration was subjected to ChIP analysis using antibodies to BMI1 (C), ubi-H2A (D) or control IgG. Presence of Ink4a/Arf sequences was examined by PCR using the primer pairs depicted in FIG. 35 or the intergenic region from Ch-8. Relative % input was determined by calculating the ratio of % input of immunoprecipitation with either BMI1 or ubi-H2A antibodies relative to IgG control immunoprecipitations. E) s.c. myc-CaP tumors formed by mock (Scr.) or IKKα-silenced cells were isolated 2 weeks after sham operation or castration and analyzed by immunohistochemistry for ubi-H2A content. F) Prostates of Ikkα$^{AA/+}$/TRAMP and Ikkα$^{AA/AA}$/TRAMP mice were collected 12 weeks after sham operation or castration and analyzed by immunohistochemistry for ubi-H2A content. G) Paraffin-embedded prostate sections corresponding to normal tissue (n=9), benign prostatic hyperplasia (n=8) or prostate cancer (n=13) were analyzed by immunohistochemistry for ubi-H2A content. The ubi-H2A staining index was quantitated by Adobe Photoshop and is indicated at the bottom (p-value is <0.001 for the malignant samples). In panels A-D, the values represent means±SD (n=3).
Figure 35:
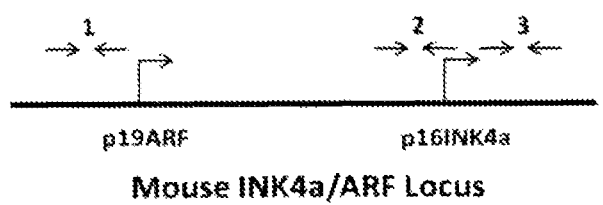
FIG. 35. Depiction of the mouse Ink4a/Arf locus. The arrows indicate the primer sets used for PCR in ChIP analysis.

29A). Interference with LT signaling also resulted in elevated p16 and p19 expression in myc-CaP tumors of castrated mice (FIG. 29B). BMI1 and other PRC1 components silence the Ink4a/Arf locus through direct binding and H2A ubiquitination (Wang et al., 2004). To examine BMI1 recruitment to the Ink4a/Arf locus in response to castration and IKKα activation, we designed three primer pairs adjacent to the p19$^{Arf}$ and p16$^{Ink4a}$ promoters (FIG. 35). ChIP experiments indicated that castration increased BMI1 recruitment to all 3 sites and that this increase was IKKα-dependent, with recruitment to sites 1 and 2 being statistically significant (FIG. 29C). Furthermore, the presence of ubi-H2A at the p16$^{Ink4}$. promoter (sites 2 and 3) was considerably increased after castration and the increase was IKKα-dependent (FIG. 29D). There was also a significant increase in total ubi-H2A within PCa cells after castration in both the myc-CaP and TRAMP models that was IKKα-dependent (FIG. 29E,F). We also found significantly increased ubi-H2A staining in human PCa specimens relative to normal prostatic tissue or benign prostatic hyperplasia (FIG. 29G), as well as a significant correlation coefficient of 0.94 between BMI1 and ubi-H2A staining of these samples.

Example 14

IKKα and BMI1 Accumulate in CD133$^+$ Cells and Control their Abundance

Figure 30:
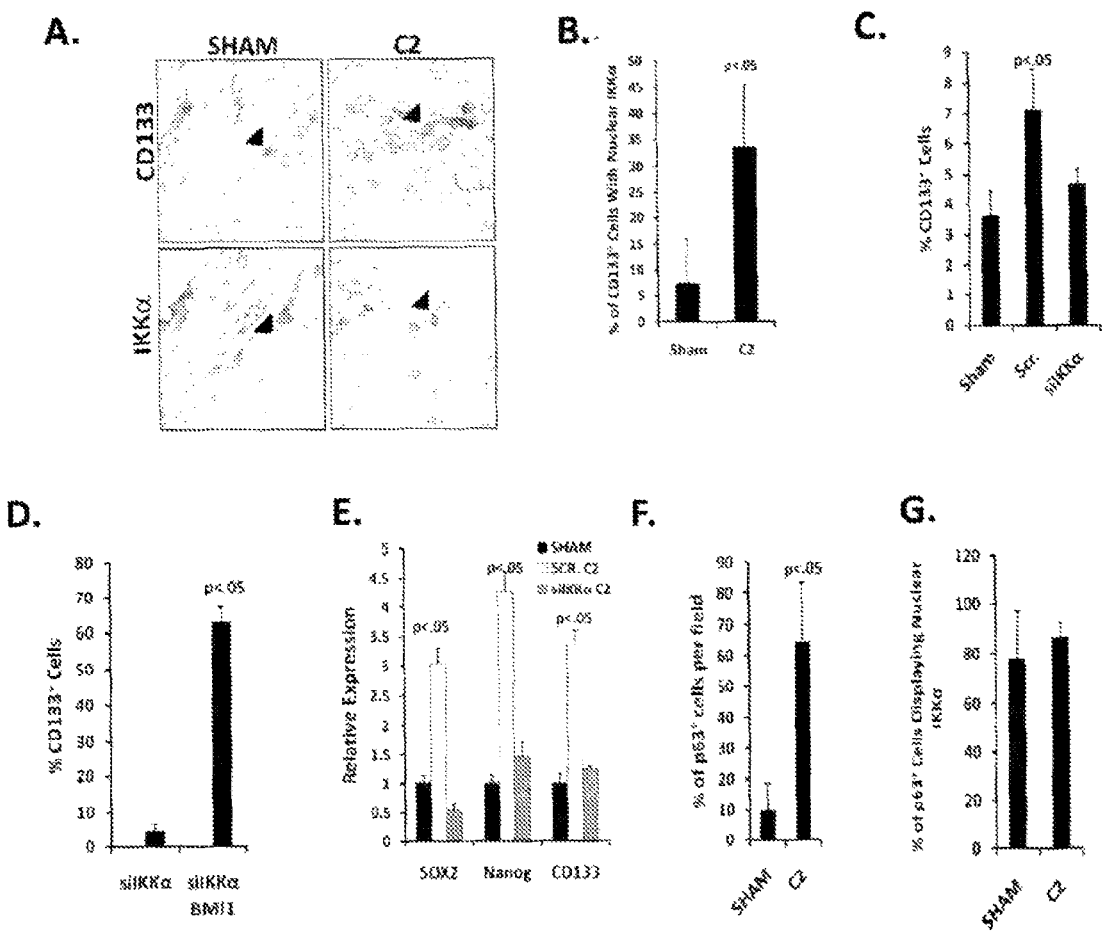
FIG. 30: Nuclear IKKα is present in cells that express markers of PCa progenitors and is required for their upregulation. A) Sequential paraffin-embedded sections from s.c. myc-CaP tumors collected 2 weeks after sham operation or castration were analyzed by immunohistochemistry for CD133 and IKKα. Arrowheads indicate CD133$^+$ cells. B) Quantification of IKKα and CD133 co-staining in 5 fields as in A per tumor, with 3 tumors analyzed for each condition. C) Single-cell suspensions from s.c. myc-CaP tumors formed by mock (Scr.) or IKKα-silenced cells that were collected 2 weeks after sham operation or castration were analyzed by flow cytometry for CD133 expression. D) Single-cell suspensions from s.c. myc-CaP tumors formed by IKKα-silenced and IKKα-silenced+BMI1 transduced cells isolated 1 week after castration were analyzed by flow cytometry for CD133 expression. E) RNA samples from s.c. myc-CaP tumors formed by mock (Scr.) or IKKα-silenced cells collected 2 weeks after sham operation or castration were analyzed for SOX2, Nanog and CD133 expression. F) Quantification of p63$^+$ cells. Three s.c. myc-CaP tumors collected 2 weeks after sham operation or castration were stained for p63 and the numbers of p63$^+$ cells were determined in 5 fields per tumor. G) Quantification of p63 and IKKα co-expression in the tumors described above. Note that even in tumors from sham operated mice, most p63$^+$ cells contain nuclear IKKα. In panels B-G, the values represent means±SD (n=3).

BMI1 acts within PCa stem cells to control their self-renewal and abundance (Lukacs et al., 2010). We examined whether IKKα accumulates within CD133$^+$ cells, a population reported to include PCa stem cells (Richardson et al., 2004). Castration augmented the abundance of CD133$^+$ cells within myc-CaP tumors and increased the fraction of CD133$^+$ cells with nuclear IKKα by 6-7-fold (FIG. 30A,B). IKKα-silencing in myc-CaP cells inhibited the castration-induced increase in the frequency of CD133$^+$ cells, but expression of ectopic BMI1 in IKKα-silenced myc-CaP cells strongly increased CD133$^+$ cell abundance (FIG. 30C, D), supporting previous reports which implicate BMI1 in self-renewal and activation of cancer stem cells/progenitors (Lobo et al., 2007). Although increased CD133 expression may reflect infiltration of CD133$^+$ hematopoietic cells into the tumors, we have not seen differences in hematopoietic cell infiltration between mock and IKKα-silenced tumors (data not shown). The effect of castration and IKKα is not unique to CD133, as expression of other prostate cancer stem cells/progenitor markers (SOX2 and Nanog) had also increased after castration, in an IKKα-dependent manner (FIG. 30E). The preponderance of another prostate cancer stem cell marker, p63, also increased after castration and correlated with nuclear IKKα (FIG. 30F,G).

Example 15

Figure 31:
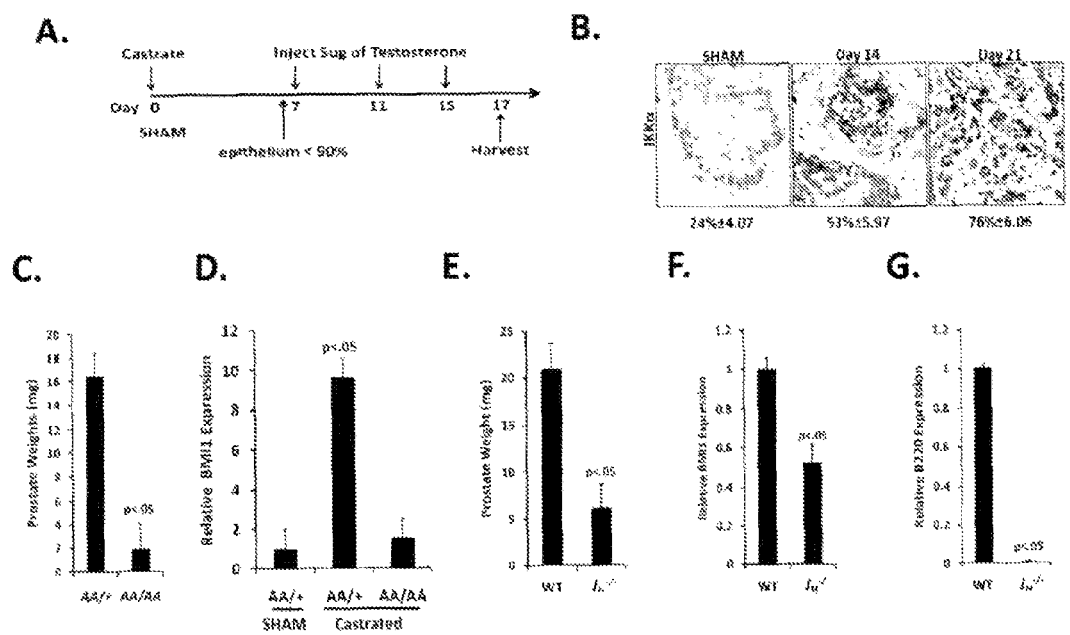
FIG. 31: IKKα controls androgen-induced regrowth of the normal prostate. A) Outline of prostate regeneration experiments. B) Prostates of Ikkα$^{AA/+}$ mice were collected at indicated times after castration and analyzed by immunohistochemistry for IKKα nuclear translocation. Percentages of cells with nuclear IKKα staining are indicated below each panel and were determined by analysis of 5 sections per prostate with a total of 3 prostates per condition. C) Prostates of Ikkα$^{AA/+}$ and Ikkα$^{AA/AA}$ mice were weighted 17 days after castration and androgen replacement. D) RNAs extracted from prostates (genotype indicated) 17 days after sham operation or castration and subsequent androgen replacement were analyzed for Bmi1 expression. E) Prostates of WT or J$_H^{-/-}$ mice were weighted 17 days after castration and androgen replacement. F,G) RNAs extracted from prostates of WT or J$_H^{-/-}$ mice 17 days after sham operation or castration and subsequent androgen replacement were analyzed for Bmi1(F) or B220 (G) expression. In panels C-G, the values represent means±SD (n=3).

Inflammatory Activation of IKKα is Required for Androgen-Induced Regrowth of the Normal Prostate The ability of prostate tumors to regenerate after androgen ablation is likely to be due to activation of prostate cancer stem cells (Maitland and Collins, 2008), a process that is BMI1-dependent (Lukacs et al., 2010). BMI1 is also involved in renewal of normal tissue stem cells (Lobo et al., 2007), including prostate stem cells (Lukacs et al., 2010). We therefore examined whether IKKα activation is required for androgen-induced growth of the involuted prostate of castrated mice, which is initiated by stem cells/progenitors (English et al., 1987; Karhadkar et al., 2004). We castrated Ikkα$^{AA/+}$ and Ikkα$^{AA/AA}$ mice and after 7 days injected them three times with testosterone to induce prostate regrowth (FIG. 31A). Immunohistochemistry revealed nuclear translocation of IKKα within 14 days after castration in Ikkα$^{AA/+}$ mice (FIG. 31B). In these mice, androgen supplementation induced prostate regrowth, but this response was abrogated in Ikkα$^{AA/AA}$ mice (FIG. 31C). In addition, castration induced Bmi1 mRNA accumulation in the normal prostate, as it did in tumors, and the increase was IKKα-dependent (FIG. 31D). We also examined whether B cells, which were found to infiltrate the prostate after castration (FIG. 36A) are required for androgen-induced prostate regrowth, similar to their role in CR-PCa (Ammirante et al., 2010). We performed a castration-regeneration experiment on B cell deficient Jh$^{-/-}$ mice (Chen et al., 1993). Indeed, the B cell deficiency severely attenuated androgen-induced prostate regrowth (FIG. 31E) and compromised Bmi1 induction (FIG. 31F). No B cells were detected in the involuted prostates of Jh$^{-/-}$ mice (FIG. 31G). Similar, but more modest, attenuation of prostate regeneration was seen in mice treated with the B cell-depleting CD20 antibody (FIG. 36A-C).

Example 16

Discussion of Examples 9-15

The results described above in Examples 9-15 demonstrate the critical role played by an inflammatory response in tissue regeneration following injury. The importance of inflammation in tissue repair and wound healing has been well appreciated (Singer and Clark, 1999), but it has been thought that the reparative functions of inflammation are largely limited to clearance of dead cells, deposition of extracellular matrix and stimulation of fibroblast proliferation (Velnar et al., 2009). Furthermore, the mechanisms by which tissue injury and tumor debulking lead to activation of signaling pathways and transcription factors that are involved in tissue regeneration and tumor recurrence, namely the Wnt and Hedgehog pathways (Beachy et al., 2004), are unknown.

Data herein in Examples 9-15 show that androgen-induced regrowth of the involuted prostate of castrated mice is highly dependent on an inflammatory response, most likely triggered by the death of androgen-deprived prostate epithelial cells, that is also responsible for rapid emergence of CR-PCa. This inflammatory response results in IKKα activation within residual prostate cells, presumably the stem cells that survive androgen ablation and drive prostate regeneration and CR-PCa emergence (Maitland and Collins, 2008). Activated IKKα is needed for upregulation of BMI1, a critical component of the histone-ubiquitinating PRC1 complex, whose role in stem cell self-renewal is well established (Lobo et al., 2007). The same inflammation-driven pathway, consisting of B cells, LT, IKKα and BMI1, that is needed for prostate regeneration, is also required for development of CR-PCa in two different mouse PCa models—the transplantable androgen-dependent myc-CaP cell line (Watson et al., 2005) and the TRAMP mouse (Gingrich et al., 1997). While androgen deprivation therapy is a frequently used treatment for PCa, it only leads to temporary tumor regression and facilitates emergence of CR-PCa, which is often incurable and lethal (Gulley et al., 2003). Although newly developed androgen receptor (AR) antagonists are likely to reduce occurrence of CR-PCa (Tran et al., 2009), there is certainly a need for new measures to counteract this major cause of cancer deaths in men (American Cancer Society, 2010). Data herein in Examples 9-15 shows that interference with the IKKα-dependent pathway of BMI1 induction in androgen-deprived PCa stem cells, represents a valid therapeutic approach to be used as an adjuvant for androgen-ablation.

IKKα, Inflammation, Stem Cell Activation and Tissue Regeneration

Tissue regeneration is likely to depend on activation of resident stem cells following injury. A key question, however, is how adult tissue stem cells sense injury and undergo activation and proliferation. Inflammation, which accompanies tissue injury, was recently implicated in stem cell activation through increased production of reactive oxygen species (Ito et al., 2004) and cytokines (Audet et al., 2001; Widera et al., 2006). However, the mechanisms by which these inflammatory manifestations trigger stem cell activation are not entirely clear. While not intending to limit the invention to a particular mechanism, in one embodiment, inflammation-responsive transcription factors, such as STAT3 and NF-κB, may be involved. It is also unclear whether the mechanisms of stem cell activation during normal tissue regeneration also account for cancer recurrence after therapy, though the latter may also be associated with inflammation (Vakkila and Lotze, 2004; Zong and Thompson, 2006). Data herein in Examples 1-15 illustrate a mechanism applicable to both normal tissue regeneration and cancer recurrence after therapy and demonstrate that contrary to prior expectations neither process is cell autonomous. In both cases, the trigger for the inflammatory response is androgen deprivation, which results in death of the normal prostate epithelium and androgen-dependent PCa cells. Cell death results in release of mediators that induce expression of chemokines that cause infiltration of immune cells into the injured tumor (Amrairante et al., 2010) or the prostate. Amongst the different cell types recruited by these chemokines, a critical role is played by B cells. As discussed above in Examples 1-8, we found that B cells accelerate development of CR-PCa by serving as a critical source of LT, a TNF family member that activates IKKα in PCa cells that survive androgen deprivation. The present results in Examples 9-15 identify B cells as critical stimulators of androgen-induced prostate regrowth, presumably by the same mechanism. While much research has been built upon the assumption that the major driver of CR-PCa is dysregulated AR activation through AR overexpression (Visakorpi et al., 1995), AR mutations (Taplin et al., 1995), or increased intratumoral androgen production (Holzbeierlein et al., 2004), our results demonstrate that this process (Examples 1-8), along with regeneration of the normal prostate (Examples 9-15), is also dependent on B lymphocytes and IKKα signaling.

While not limiting the invention to a particular mechanism, in one embodiment, IKKα stimulates proliferation of the putative stem cells/progenitors responsible for emergence of CR-PCa and androgen-induced prostate regeneration presumably through induction of BMI1. The role of BMI1 in both of these processes is previously addressed (Lobo et al., 2007; Lukacs et al., 2010). Data herein in Examples 9-15, however, show that IKKα activity, presumably via BMI1, is required for elevated expression of a number of PCa stem cell markers, including CD133, p63, Nanog, and Sox2 in androgen-deprived PCa tumors. Most importantly, data herein in Examples 9-15 provide a clear demonstration that tissue regeneration is not an entirely cell autonomous process. Furthermore, a requirement for B cells in prostate regeneration has never been reported.

IKKα Couples Inflammation to Epigenetic Chromatin Modifications

Alterations of chromatin modifications and structure are a common occurrence in cancer, consistent with the participation of epigenetic mechanisms in tumorigenesis (Jones and Baylin, 2007). Quite often, epigenetic alterations in cancer lead to silencing of tumor suppressor loci. However, the microenvironmental signals and pathways that trigger these epigenetic modifications are poorly understood. Our results in Examples 1-15 demonstrate that at least during development of CR-PCa, IKKα activation leads to H2A ubiquitination 1n1 and eventual repression of the tumor suppressor $p16^{Ink4a}/p19^{Arf}$ locus, presumably through BMI1. Notably, a correlation between nuclear accumulation of IKKα, elevated BMI1 expression and enhanced H2A ubiquitination was seen in both mouse and human PCa, suggesting that this epigenetic function of IKKα may be conserved.

While not limiting the invention to a particular mechanism, in one embodiment, the ability of IKKα to induce Bmi1 transcription is mediated through its interaction with E2F1 which results in E2F1 recruitment to the Bmi1 promoter. Based on our present results and previous studies indicating that CBP potentiates E2F1 DNA binding and activity (Trouche and Kouzarides, 1996; Tu et al., 2006), a likely mechanism may involve IKKα-mediated recruitment of CBP (or the related molecule p300) to E2F1 and enhancement of E2F1 DNA binding by CBP-mediated acetylation. IKKα may mediate this recruitment by phosphorylation of CBP, which can also modulate CBP activity (Huang et al., 2007). E2F1 activity is also subject to negative regulation through an interaction with Rb (DeGregori and Johnson, 2006). Without limiting the invention to a particular mechanism, the inventors believe that it is rather unlikely that IKKα controls E2F1 activity via Rb because IKKα-mediated Bmi1 induction is seen both in myc-CaP tumors and in TRAMP mice, but the latter express SV40 T antigen in their PCa cells which should sequester Rb away from E2F1 (DeCaprio et al., 1988).

IKKα may modulate chromatin structure and affect expression of tumor suppressors through BMI1-independent mechanisms, as it was reported to promote H3 phosphorylation (Anest et al., 2003; Yamamoto et al., 2003) and SMRT derepression (Hoberg et al., 2006). Through effects on NF-κB, IKKα may also promote expression of the histone demethylase Jmjd3 (De Santa et al., 2007).

Translational Implications

The requirement for IKKα activation in BMI1 induction and tumor and tissue regeneration was seen in three different scenarios: the myc-CaP and TRAMP models for PCa and androgen-induced regeneration of the normal prostate. Thus, this requirement is not model specific and should not be affected by the limitations of either PCa model. Furthermore, data herein in Examples 9-15 show a strong correlation between presence of nuclear (i.e. activated) IKKα and BMI1 expression and between BMI1 expression and the total content of ubi-H2A in human PCa specimens. While not limiting the invention to a particular mechanism responsible for IKKα activation/nuclear accumulation in human PCa, in one embodiment, the injury-induced mechanism of IKKα activation which depends on B lymphocytes and LT signaling is likely to be evolutionary conserved and not restricted to the mouse. Indeed, elevated expression of the B cell chemoattractant CXCL13 was observed in human PCa and found to correlate with clinical grade (Singh et al., 2009). In addition, a common genetic polymorphism that affects LT expression correlates with the effect of nonsteroidal anti-inflammatory drugs (NSAIDs) on PCa incidence (Liu et al., 2006). Data herein in Examples 9-15 suggests that B cell-depleting drugs, such as anti-CD20 (Rituximab) and inhibitors of LT signaling, such as the LTβR-Fc fusion protein, are efficacious adjuvants to standard androgen ablation therapy. Based on our mouse studies, we predict that such combinations should reduce one or both the occurrence of castration resistance and metastatic spread, the major causes of death in PCa.

REFERENCES IN EXAMPLES 2-8

1. Isaacs, J. T. The biology of hormone refractory prostate cancer. Why does it develop? *Urol Clin North Am* 26, 263-273 (1999).
2. Gulley, J., Figg, W. D. & Dahut, W. L. Treatment options for androgen-independent prostate cancer. *Clin Adv Hematol Oncol* 1, 49-57 (2003).
3. Tran, C. et al. Development of a second-generation antiandrogen for treatment of advanced prostate cancer. *Science* 324, 787-790 (2009).
4. Sin, R. J. et al. The nuclear factor-kappaB pathway controls the progression of prostate cancer to androgen-independent growth. *Cancer Res* 68, 6762-6769 (2008).
5. Karin, M., Lawrence, T. & Nizet, V. Innate immunity gone awry linking microbial infections to chronic inflammation and cancer. *Cell* 124, 823-835 (2006).
6. Karin, M. Nuclear factor-kappaB in cancer development and progression. *Nature* 441, 431-436 (2006).
7. Balkwill, F., Charles, K. A. & Mantovani, A. Smoldering and polarized inflammation in the initiation and promotion of malignant disease. *Cancer Cell* 7, 211-217 (2005).
8. Coussens, L. M. & Werb, Z. Inflammation and cancer. *Nature* 420, 860-867 (2002).
9. de Visser, K. E., Korets, L. V. & Coussens, L. M. De novo carcinogenesis promoted by chronic inflammation is B lymphocyte dependent. *Cancer Cell* 7, 411-423 (2005).
10. Mantovani, A., Allavena, P., Sica, A. & Balkwill, F. Cancer-related inflammation. *Nature* 454, 436-444 (2008).
11. Luo, J. L. et al. Nuclear cytokine activated IKKα controls prostate cancer metastasis by repressing maspin. *Nature* 446, 690-694 (2007).
12. Bai, A., Higham, E., Eisen, H. N., Wittrup, K. D. & Chen, J. Rapid tolerization of virus-activated tumor-specific CD8+ T cells in prostate tumors of TRAMP mice. *Proc Natl Acad Sci USA* 105, 13003-13008 (2008).
13. Ellwood-Yen, K. et al. Myc-driven murine prostate cancer shares molecular features with human prostate tumors. *Cancer Cell* 4, 223-238 (2003).
14. Park, B. K. et al. NF-kappaB in breast cancer cells promotes osteolytic bone metastasis by inducing osteoclastogenesis via GM-CSF. *Nat Med* 13, 62-69 (2007).
15. Wen, D. et al. A selective small molecule IkappaB Kinase beta inhibitor blocks nuclear factor kappaB-mediated inflammatory responses in human fibroblast-like synoviocytes, chondrocytes, and mast cells. *J Pharmacol Exp Ther* 317, 989-1001 (2006).
16. Legler, D. F. et al. B cell-attracting chemokine 1, a human CXC chemokine expressed in lymphoid tissues, selectively attracts B lymphocytes via BLR1/CXCR5. *J Exp Med* 187, 655-660 (1998).
17. Chen, T., Wang, L. H. & Farrar, W. L. Interleukin 6 activates androgen receptor-mediated gene expression through a signal transducer and activator of transcription 3-dependent pathway in LNCaP prostate cancer cells. *Cancer Res* 60, 2132-2135 (2000).
18. Eriksen, K. W. et al. Constitutive STAT3-activation in Sezary syndrome: tyrphostin AG490 inhibits STAT3-activation, interleukin-2 receptor expression and growth of leukemic Sezary cells. *Leukemia* 15, 787-793 (2001).
19. Hamel, K. et al. Suppression of proteoglycan-induced arthritis by anti-CD20 B Cell depletion therapy is mediated by reduction in autoantibodies and CD4+ T cell reactivity. *J Immunol* 180, 4994-5003 (2008).
20. Worm, M. M., Tsytsykova, A. & Geha, R. S. CD40 ligation and IL-4 use different mechanisms of transcriptional activation of the human lymphotoxin alpha promoter in B cells. *Eur J Immunol* 28, 901-906 (1998).
21. Tumanov, A. V. et al. Dissecting the role of lymphotoxin in lymphoid organs by conditional targeting. *Immunol Rev* 195, 106-116 (2003).
22. Lee, Y. et al. Recruitment and activation of naive T cells in the islets by lymphotoxin beta receptor-dependent tertiary lymphoid structure. *Immunity* 25, 499-509 (2006).
23. Ghiringhelli, F. et al. Activation of the NLRP3 inflammasome in dendritic cells induces IL-1beta-dependent adaptive immunity against tumors. *Nat Med,* 15, 1170-1178 (2009).
24. Scaffidi, P., Misteli, T. & Bianchi, M. E. Release of chromatin protein HMGB1 by necrotic cells triggers inflammation. *Nature* 418, 191-195 (2002).
25. Sakurai, T. et al. Hepatocyte necrosis induced by oxidative stress and IL-1 alpha release mediate carcinogen-induced compensatory proliferation and liver tumorigenesis. *Cancer Cell* 14, 156-165 (2008).
26. Nimmerjahn, F. & Ravetch, J. V. Fc-receptors as regulators of immunity. *Adv Immunol* 96, 179-204 (2007).
27. Bonizzi, G. et al. Activation of IKKα target genes depends on recognition of specific κB binding sites by RelB:p52 dimers. *Embo J* 23, 4202-4210 (2004).
28. Kortylewski, M. & Yu, H. Stat3 as a potential target for cancer immunotherapy. *J Immunother* 30, 131-139 (2007).
29. Smith, P. C., Hobisch, A., Lin, D. L., Culig, Z. & Keller, E. T. Interleukin-6 and prostate cancer progression. *Cytokine Growth Factor Rev* 12, 33-40 (2001).
30. Liu, X., Plummer, S. J., Nock, N. L., Casey, G. & Witte, J. S. Nonsteroidal antiinflammatory drugs and decreased risk of advanced prostate cancer: modification by lymphotoxin alpha. *Am J Epidemiol* 164, 984-989 (2006).

REFERENCES IN EXAMPLES 9-16

American Cancer Society, *Cancer Facts & Figures* 2007. Atlanta: American Cancer Society, 2007.
Ben-Neriah, Y., Karin, M. (2011). Inflammation meets cancer, with NF-κB as the matchmaker. Nat. Immunol. In Press.
Ammirante, M., Luo, J. L., Grivennikov, S., Nedospasov, S., and Karin, M. (2010). B-cell-derived lymphotoxin promotes castration-resistant prostate cancer. Nature 464, 302-305.
Anest, V., Hanson, J. L., Cogswell, P. C., Steinbrecher, K. A., Stahl, B. D., and Baldwin, A. S. (2003). A nucleosomal function for IkappaB kinase-alpha in NF-kappaB-dependent gene expression. Nature 423, 659-663.
Audet, J., Miller, C. L., Rose-John, S., Piret, J. M., and Eaves, C. J. (2001). Distinct role of gp130 activation in promoting self-renewal divisions by mitogenically stimulated murine hematopoietic stem cells. Proc Natl Acad Sci USA 98, 1757-1762.
Balkwill, F., and Mantovani, A. (2001). Inflammation and cancer: back to Virchow? Lancet 357, 539-545.

Beachy, P. A., Karhadkar, S. S., and Berman, D. M. (2004). Tissue repair and stem cell renewal in carcinogenesis. Nature 432, 324-331.

Berezovska, O. P., Glinskii, A. B., Yang, Z., Li, X. M., Hoffman, R. M., and Glinsky, G. V. (2006). Essential role for activation of the Polycomb group (PcG) protein chromatin silencing pathway in metastatic prostate cancer. Cell Cycle 5, 1886-1901.

Cao, Y., Bonizzi, G., Seagroves, T. N., Greten, F. R., Johnson, R., Schmidt, E. V., and Karin, M. (2001). IKKalpha provides an essential link between RANK signaling and cyclin D1 expression during mammary gland development. Cell 107, 763-775.

Chen, J., Trounstine, M., Alt, F. W., Young, F., Kurahara, C., Loring, J. F., and Huszar, D. (1993). Immunoglobulin gene rearrangement in B cell deficient mice generated by targeted deletion of the JH locus. Int Immunol 5, 647-656.

De Santa, F., Totaro, M. G., Prosperini, E., Notarbartolo, S., Testa, G., and Natoli, G. (2007). The histone H3 lysine-27 demethylase Jmjd3 links inflammation to inhibition of polycomb-mediated gene silencing. Cell 130, 1083-1094.

DeCaprio, J. A., Ludlow, J. W., Figge, J., Shew, J. Y., Huang, C. M., Lee, W. H., Marsilio, E., Paucha, E., and Livingston, D. M. (1988). SV40 large tumor antigen forms a specific complex with the product of the retinoblastoma susceptibility gene. Cell 54, 275-283.

DeGregori, J., and Johnson, D. G. (2006). Distinct and Overlapping Roles for E2F Family Members in Transcription, Proliferation and Apoptosis. Curr Mol Med 6, 739-748.

Descargues, P., Sil, A, K., Sano, Y., Korchynskyi, O., Han, G., Owens, P., Wang, X. J., and Karin, M. (2008). IKKalpha is a critical coregulator of a Smad4-independent TGFbeta-Smad2/3 signaling pathway that controls keratinocyte differentiation. Proc Natl Acad Sci USA 105, 2487-2492.

Dvorak, H. F. (1986). Tumors: wounds that do not heal. Similarities between tumor stroma generation and wound healing. N Engl J Med 315, 1650-1659.

Ellwood-Yen, K., Graeber, T. G., Wongvipat, J., Iruela-Arispe, M. L., Zhang, J., Matusik, R., Thomas, G. V., and Sawyers, C. L. (2003). Myc-driven murine prostate cancer shares molecular features with human prostate tumors. Cancer Cell 4, 223-238.

English, H. F., Santen, R. J., and Isaacs, J. T. (1987). Response of glandular versus basal rat ventral prostatic epithelial cells to androgen withdrawal and replacement. Prostate 11, 229-242.

Galbiati, L., Mendoza-Maldonado, R., Gutierrez, M. I., and Giacca, M. (2005). Regulation of E2F-1 after DNA damage by p300-mediated acetylation and ubiquitination. Cell Cycle 4, 930-939.

Gingrich, J. R., Barrios, R. J., Kattan, M. W., Nahm, H. S., Finegold, M. J., and Greenberg, N. M. (1997). Androgen-independent prostate cancer progression in the TRAMP model, Cancer Res 57, 4687-4691.

Gingrich, J. R., Barrios, R. J., Morton, R. A., Boyce, B. F., DeMayo, F. J., Finegold, M. J., Angelopoulou, R., Rosen, J. M., and Greenberg, N. M. (1996). Metastatic prostate cancer in a transgenic mouse. Cancer Res 56, 4096-4102.

Greenberg, N. M., DeMayo, F., Finegold, M. J., Medina, D., Tilley, W. D., Aspinall, J. O., Cunha, G. R., Donjacour, A. A., Matusik, R. J., and Rosen, J. M. (1995). Prostate cancer in a transgenic mouse. Proc Natl Acad Sci USA 92, 3439-3443.

Grivennikov, S. I., Graten, F. R., and Karin, M. (2011) Immunity, inflammation, and cancer. Cell 140, 883-899.

Gulley, J., Figg, W. D., and Dahut, W. L. (2003). Treatment options for androgen-independent prostate cancer. Clin Adv Hematol Oncol 1, 49-57.

Guo, W. J., Datta, S., Band, V., and Dimri, G. P. (2007). Mel-18, a polycomb group protein, regulates cell proliferation and senescence via transcriptional repression of Bmi-1 and c-Myc oncoproteins. Mol Biol Cell 18, 536-546.

Hoberg, J. E., Popko, A. E., Ramsey, C. S., and Mayo, M. W. (2006). IkappaB kinase alpha-mediated derepression of SMRT potentiates acetylation of RelA/p65 by p300. Mol Cell Biol 26, 457-471.

Holzbeierlein, J., Lal, P., LaTulippe, E., Smith, A., Satagopan, J., Zhang, L., Ryan, C., Smith, S., Scher, H., Scardino, P., et al. (2004). Gene expression analysis of human prostate carcinoma during hormonal therapy identifies androgen-responsive genes and mechanisms of therapy resistance. Am J Pathol 164, 217-227.

Hu, Y., Baud, V., Delhase, M., Zhang, P., Deerinck, T., Ellisman, M., Johnson, R., and Karin, M. (1999). Abnormal morphogenesis but intact IKK activation in mice lacking the IKKalpha subunit of IkappaB kinase. Science 284, 316-320.

Hu, Y., Baud, V., Oga, T., Kim, K. I., Yoshida, K., and Karin, M. (2001). IKKalpha controls formation of the epidermis independently of NF-kappaB. Nature 410, 710-714.

Huang, W. C., Ju, T. K., Hung, M. C., and Chen, C. C. (2007). Phosphorylation of CBP by IKKalpha promotes cell growth by switching the binding preference of CBP from p53 to NF-kappaB. Mol Cell 26, 75-87.

Hurwitz, A. A., Foster, B. A., Allison, J. P., Greenberg, N. M., and Kwon, E. D. (2001). The TRAMP mouse as a model for prostate cancer. Curr Protoc Immunol Chapter 20, Unit 20 25.

Hussain, S. P., and Harris, C. C. (2007). Inflammation and cancer: an ancient link with novel potentials. Int J Cancer 121, 2373-2380.

Ianari, A., Gallo, R., Palma, M., Alesse, E., and Gulino, A. (2004). Specific role for p300/CREB-binding protein-associated factor activity in E2F1 stabilization in response to DNA damage. J Biol Chem 279, 30830-30835.

Ito, K., Hirao, A., Arai, F., Matsuoka, S., Takubo, K., Hamaguchi, I., Nomiyama, K., Hosokawa, K., Sakurada, K., Nakagata, N., et al. (2004). Regulation of oxidative stress by ATM is required for self-renewal of haematopoietic stem cells. Nature 431, 997-1002.

Jacobs, J. J., Scheijen, B., Voncken, J. W., Kieboom, K., Berns, A., and van Lohuizen, M. (1999). Bmi-1 collaborates with c-Myc in tumorigenesis by inhibiting c-Myc-induced apoptosis via INK4a/ARF. Genes Dev 13, 2678-2690.

Jones, P. A., and Baylin, S. B. (2007). The epigenomics of cancer. Cell 128, 683-692.

Karhadkar, S. S., Bova, G. S., Abdallah, N., Dhara, S., Gardner, D., Maitra, A., Isaacs, J. T., Berman, D. M., and Beachy, P. A. (2004). Hedgehog signalling in prostate regeneration, neoplasia and metastasis. Nature 431, 707-712.

Karin, M. (2005). Inflammation and cancer: the long reach of Ras. Nat. Med 11, 20-21.

Karin, M. (2009). NF-kappaB as a critical link between inflammation and cancer. Cold Spring Harb Perspect Biol 1, a000141.

Konuma, T., Oguro, H., and Iwama, A. (2010). Role of the polycomb group proteins in hematopoietic stem cells. Dev Growth Differ 52, 505-516.

Kuraishy, A. I., French, S. W., Sherman, M., Herling, M., Jones, D., Wall, R., and Teitell, M. A. (2007). TORC2 regulates germinal center repression of the TCL1 oncoprotein to promote B cell development and inhibit transformation. Proc Natl Acad Sci USA 104, 10175-10180.

Lehr, H. A., Mankoff, D. A., Corwin, D., Santeusanio, G., and Gown, A. M. (1997). Application of photoshop-based image analysis to quantification of hormone receptor expression in breast cancer. J Histochem Cytochem 45, 1559-1565.

Liu, X., Plummer, S. J., Nock, N. L., Casey, G., and Witte, J. S. (2006). Nonsteroidal antiinflammatory drugs and decreased risk of advanced prostate cancer: modification by lymphotoxin alpha. Am J Epidemiol 164, 984-989.

Lobo, N. A., Shimono, Y., Qian, D., and Clarke, M. F. (2007). The biology of cancer stem cells. Annu Rev Cell Dev Biol 23, 675-699.

Lukacs, R. U., Memarzadeh, S., Wu, H., and Witte, O. N. (2010). Bmi-1 is a crucial regulator of prostate stem cell self-renewal and malignant transformation. Cell Stem Cell 7, 682-693.

Luo, J. L., Maeda, S., Hsu, L. C., Yagita, H., and Karin, M. (2004) Inhibition of NF-kappaB in cancer cells converts inflammation-induced tumor growth mediated by TNFalpha to TRAIL-mediated tumor regression. Cancer Cell 6, 297-305.

Luo, J. L., Tan, W., Ricono, J. M., Korchynskyi, O., Zhang, M., Gonias, S. L., Cheresh, D. A., and Karin, M. (2007). Nuclear cytokine-activated IKKalpha controls prostate cancer metastasis by repressing Maspin. Nature 446, 690-694.

Maitland, N. J., and Collins, A. T. (2008). Prostate cancer stem cells: a new target for therapy. J Clin Oncol 26, 2862-2870.

Marinari, B., Moretti, F., Botti, E., Giustizieri, M. L., Descargues, P., Giunta, A., Stolfi, C., Ballaro, C., Papoutsaki, M., Alema, S., et al. (2008). The tumor suppressor activity of IKKalpha in stratified epithelia is exerted in part via the TGF-beta antiproliferative pathway. Proc Natl Acad Sci USA 105, 17091-17096.

Nowak, K., Kerl, K., Fehr, D., Kramps, C., Gessner, C., Killmer, K., Samans, B., Berwanger, B., Christiansen, H., and Lutz, W. (2006). BMI1 is a target gene of E2F-1 and is strongly expressed in primary neuroblastomas. Nucleic Acids Res 34, 1745-1754.

Ohtani, K., DeGregori, J., and Nevins, J. R. (1995). Regulation of the cyclin E gene by transcription factor E2F1. Proc Natl Acad Sci USA 92, 12146-12150.

Richardson, G. D., Robson, C. N., Lang, S. H., Neal, D. E., Maitland, N. J., and Collins, A. T. (2004). CD133, a novel marker for human prostatic epithelial stem cells. J Cell Sci 117, 3539-3545.

Senftleben, U., Cao, Y., Xiao, G., Greten, F. R., Krahn, G., Bonizzi, G., Chen, Y., Hu, Y., Fong, A., Sun, S. C., and Karin, M. (2001). Activation by IKKalpha of a second, evolutionary conserved, NF-kappa B signaling pathway. Science 293, 1495-1499.

Sil, A. K., Maeda, S., Sano, Y., Roop, D. R., and Karin, M. (2004). IkappaB kinase-alpha acts in the epidermis to control skeletal and craniofacial morphogenesis. Nature 428, 660-664.

Singer, A. J., and Clark, R. A. (1999). Cutaneous wound healing. N Engl J Med 341, 738-746.

Singh, S., Singh, R., Sharma, P. K., Singh, U. P., Rai, S, N., Chung, L. W., Cooper, C. R., Novakovic, K. R., Grizzle, W. E., and Lillard, J. W., Jr. (2009). Serum CXCL13 positively correlates with prostatic disease, prostate-specific antigen and mediates prostate cancer cell invasion, integrin clustering and cell adhesion. Cancer Lett 283, 29-35.

Taplin, M. E., Bubley, G. J., Shuster, T. D., Frantz, M. E., Spooner, A. E., Ogata, G. K., Keer, H. N., and Balk, S. P. (1995). Mutation of the androgen-receptor gene in metastatic androgen-independent prostate cancer. N Engl J Med 332, 1393-1398.

Tran, C., Ouk, S., Clegg, N. J., Chen, Y., Watson, P. A., Arora, V., Wongvipat, J., Smith-Jones, P. M., Yoo, D., Kwon, A., et al. (2009). Development of a second-generation antiandrogen for treatment of advanced prostate cancer. Science 324, 787-790.

Trouche, D., and Kouzarides, T. (1996). E2F1 and E1A(12S) have a homologous activation domain regulated by RB and CBP. Proc Natl Acad Sci USA 93, 1439-1442.

Tu, Z., Prajapati, S., Park, K. J., Kelly, N. J., Yamamoto, Y., and Gaynor, R. B. (2006). IKK alpha regulates estrogen-induced cell cycle progression by modulating E2F1 expression. J Biol Chem 281, 6699-6706.

Vakkila, J., and Lotze, M. T. (2004). Inflammation and necrosis promote tumour growth. Nat Rev Immunol 4, 641-648.

Varambally, S., Dhanasekaran, S. M., Zhou, M., Barrette, T. R., Kumar-Sinha, C., Sanda, M. G., Ghosh, D., Pienta, K. J., Sewall, R. G., Otte, A. P., et al. (2002). The polycomb group protein EZH2 is involved in progression of prostate cancer. Nature 419, 624-629.

Velnar, T., Bailey, T., and Smrkolj, V. (2009). The wound healing process: an overview of the cellular and molecular mechanisms. J Int Med Res 37, 1528-1542.

Visakorpi, T., Hyytinen, E., Koivisto, P., Tanner, M., Keinanen, R., Palmberg, C., Palotie, A., Tammela, T., Isola, J., and Kallioniemi, O. P. (1995). In vivo amplification of the androgen receptor gene and progression of human prostate cancer. Nat Genet. 9, 401-406.

Wang, H., Wang, L., Erdjument-Bromage, H., Vidal, M., Tempst, P., Jones, R. S., and Zhang, Y. (2004). Role of histone H2A ubiquitination in Polycomb silencing. Nature 431, 873-878.

Watson, P. A., Ellwood-Yen, K., King, J. C., Wongvipat, J., Lebeau, M. M., and Sawyers, C. L. (2005). Context-dependent hormone-refractory progression revealed through characterization of a novel murine prostate cancer cell line. Cancer Res 65, 11565-11571.

Widera, D., Mikenberg, I., Elvers, M., Kaltschmidt, C., and Kaltschmidt, B. (2006). Tumor necrosis factor alpha triggers proliferation of adult neural stem cells via IKK/NF-kappaB signaling. BMC Neurosci 7, 64.

Yamamoto, Y., Verma, U. N., Prajapati, S., Kwak, Y. T., and Gaynor, R. B. (2003). Histone H3 phosphorylation by IKK-alpha is critical for cytokine-induced gene expression. Nature 423, 655-659.

Yu, J., Rhodes, D. R., Tomlins, S. A., Cao, X., Chen, G., Mehra, R., Wang, X., Ghosh, D., Shah, R. B., Varambally, S., et al. (2007). A polycomb repression signature in metastatic prostate cancer predicts cancer outcome. Cancer Res 67, 10657-10663.

Zong, W. X., and Thompson, C. B. (2006). Necrotic death as a cell fate. Genes Dev 20, 1-15.

We claim:

1. A method for reducing one or more of (a) growth of castration resistant prostate cancer (CaP) cells in a tissue and (b) metastasis of castration resistant prostate cancer (CaP) cells in a tissue, in a mammalian subject in need thereof, comprising administering to said subject a therapeutically effective amount of a compound that reduces one or more of (i) the number of B cells in said tissue, and
(ii) the function of B cells in said tissue,
wherein said compound reduces the number of B cells in said tissue, and wherein said compound comprises LTβR-Ig.

2. A method for reducing one or more of (a) growth of castration resistant prostate cancer (CaP) cells in a tissue and (b) metastasis of castration resistant prostate cancer (CaP) cells in a tissue, in a mammalian subject in need thereof, comprising administering to said subject a therapeutically effective amount of a compound that reduces one or more of
(i) the number of B cells in said tissue, and
(ii) the function of B cells in said tissue,
wherein said compound reduces the number of B cells in said tissue and reduces the level of expression of lymphotoxin-β, and wherein said compound comprises ML120B.

3. A method for reducing one or more of (a) growth of castration resistant prostate cancer (CaP) cells in a tissue and (b) metastasis of castration resistant prostate cancer (CaP) cells in a tissue, in a mammalian subject in need thereof, comprising administering to said subject a therapeutically effective amount of a compound that reduces one or more of
(i) the number of B cells in said tissue, and
(ii) the function of B cells in said tissue,
wherein said compound reduces one or more function of B cells and comprises an IKKβ inhibitor, and wherein said IKKβ inhibitor is selected from the group consisting of ML120B, PS-1145 dihydrochloride, BMS-345541 and LC-1.

* * * * *